United States Patent
Gossage et al.

(10) Patent No.: US 8,961,965 B2
(45) Date of Patent: Feb. 24, 2015

(54) METHODS OF DIAGNOSING AND TREATING PULMONARY DISEASES OR DISORDERS

(75) Inventors: David L Gossage, Gaithersburg, MD (US); Deepak B. Khatry, Gaithersburg, MD (US); Gregory P. Geba, Sparta, NJ (US); Nestor Molfino, San Francisco, CA (US); Joseph M. Parker, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 13/474,459

(22) Filed: May 17, 2012

(65) Prior Publication Data

US 2012/0328606 A1 Dec. 27, 2012

Related U.S. Application Data

(60) Provisional application No. 61/487,506, filed on May 18, 2011.

(51) Int. Cl.
*A61K 39/395* (2006.01)
*G01N 33/569* (2006.01)
*G06F 19/00* (2011.01)

(52) U.S. Cl.
CPC ........ *G01N 33/56972* (2013.01); *G06F 19/345* (2013.01); *G06F 19/3456* (2013.01); *G01N 2800/12* (2013.01); *G01N 2800/52* (2013.01); *G01N 2800/60* (2013.01)
USPC .................. 424/130.1; 424/133.1; 424/143.1; 530/350; 530/388.1

(58) Field of Classification Search
None
See application file for complete search history.

(56) References Cited

U.S. PATENT DOCUMENTS

2009/0197808 A1 8/2009 Pilon
2010/0291073 A1 11/2010 Koike et al.

FOREIGN PATENT DOCUMENTS

WO  WO 2008/143878  * 11/2008
WO  WO 2008/144850  * 12/2008

OTHER PUBLICATIONS

International Search Report corresponding to PCT/US2012/038412 dated Oct. 5, 2012.
Kolbeck, Roland et al., 2010, "MEDI-563, a humanized anti-IL-5 receptor α mAB with enhanced antibody-dependent cell-mediated cytotoxicity function", J. Allergy Clin Immunol, 125: 1344-53.
Sarraf, Khaled M. et al., 2009, "Neutrophil/lymphocyte ratio and its association with survival after complete resection in non-small cell lung cancer", The Journal of Thoracic and Cardiovascular Surgery, 137(2):425, abstract.
USAN "Statement on a Nonproprietary Name Adopted by the USAN Council" (online); downloaded from http://www.ama-assn.org/resources/doc/usan/benralizumab.pdf on Sep. 21, 2012.

* cited by examiner

*Primary Examiner* — Dong Jiang

(57) ABSTRACT

The present disclosure provides methods of diagnosing a subject as having a pulmonary disease or disorder, e.g., an eosinophilic disease or disorder based on the determination of white blood cell ratios. The disclosure also provides white blood cell ratio-based methods of treating, prognosing, or monitoring a pulmonary disease or disorder, as well as methods of methods of predicting a dosage regimen, identifying a candidate therapeutic agent, identifying a patient as a candidate for a therapeutic agent, and methods of designing a personalized therapy.

3 Claims, 14 Drawing Sheets

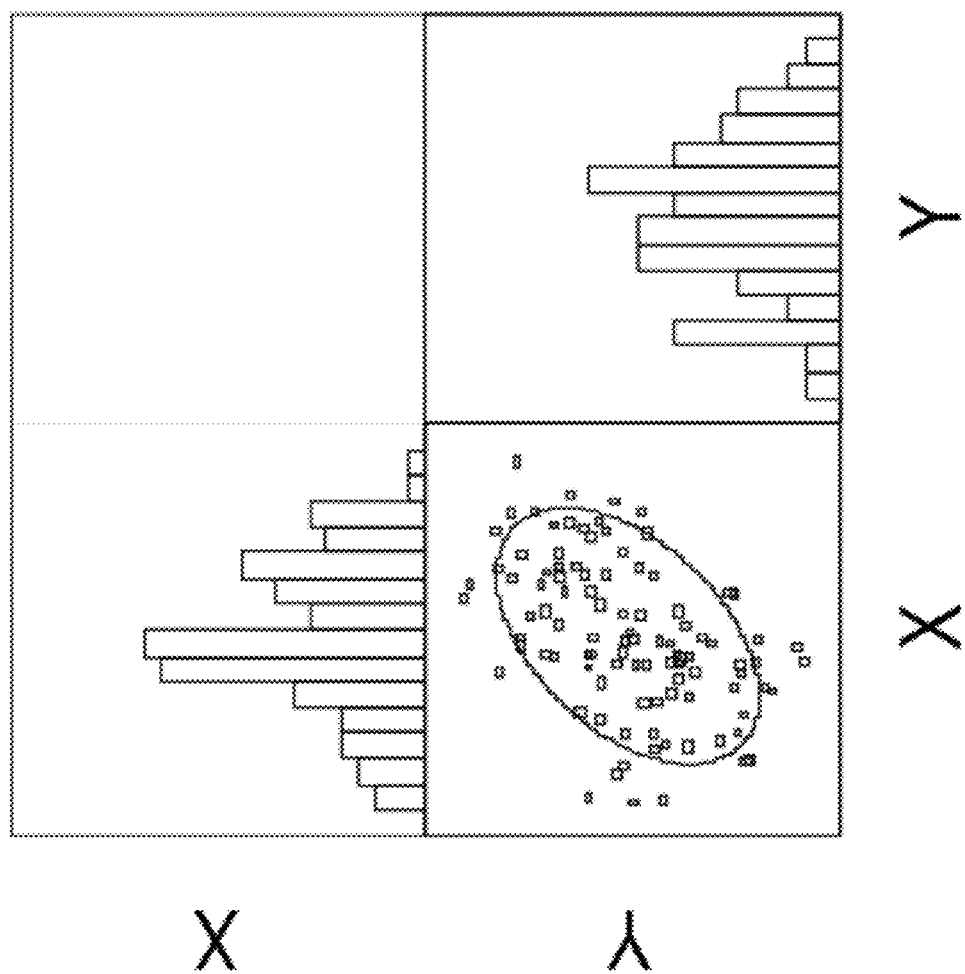

Generic Model

Score for Sputum EOS % < 2.0:
a + [b x Blood EOS/Blood Lymphocyte] − [c x natural log (Blood EOS/Blood Neutrophil)]

Score for Sputum EOS % ≥ 2.0:
d + [e x Blood EOS/Blood Lymphocyte] − [f x natural log (Blood EOS/Blood Neutrophil)]

95% CI of Model Coefficients

| Coefficient | Current Model | Mean | Median | 95% CI (Lower) | 95% CI (Upper) |
|---|---|---|---|---|---|
| a | -9.5243233 | -23.5236407 | -11.8804453 | -74.4665880 | -6.6279326 |
| b | 70.0974823 | 135.0464151 | 103.2067268 | 45.2753179 | 412.8504520 |
| c | -3.7789926 | -11.3740664 | -4.3005131 | -38.5398678 | -2.2608717 |
| d | -14.5853365 | -30.2162098 | -19.9893169 | -95.2441210 | -10.2884127 |
| e | 101.2197561 | 176.1840771 | 143.9563797 | 65.2729494 | 473.1979015 |
| f | -3.9567050 | -11.6614464 | -4.7160122 | -39.5223095 | -2.3358682 |

FIG. 7

METHODS OF DIAGNOSING AND TREATING PULMONARY DISEASES OR DISORDERS

This application claims benefit under 35 U.S.C. §119(e) of the U.S. Provisional Application No. 61/487,506 filed May 18, 2011. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name "IL5R400US_sequencelisting.txt"; Size: 8,256 bytes; and Date of Creation: May 17, 2012) filed with the application is incorporated herein by reference in its entirety.

FIELD OF THE DISCLOSURE

The present disclosure provides methods and systems for the treatment of pulmonary diseases or disorders based on the calculation of white blood cell ratios as a simple, low-cost alternative to induced sputum.

BACKGROUND

Accurate diagnostic of pulmonary diseases such as asthma or COPD is crucial to determine the appropriate treatment. Asthma and COPD are often misdiagnosed, and persons with COPD are treated instead for asthma and vice versa (ATS, 1995). In fact, primary care physicians revealed frequently prescribe similar medications for COPD and asthma even though the appropriate treatments differ (Kesten et al., 1993).

Severe asthma patients have frequent exacerbations and hospitalizations and account for over half of the cost of the disease and most of its mortality (Gaga et al., 2009). Inflammation, an important feature in severe asthma, exhibits different phenotypes that can be characterized by persistence of varying degrees of eosinophilic and neutrophilic infiltration (Balzar et al., 2002). The presence of eosinophils in asthma has been well documented via airway biopsy studies. The clinical importance of eosinophils in asthma has been demonstrated by the observation of frequent asthma exacerbations in patients who have sputum eosinophil counts >3%. Moreover, clinical trials designed to adjust inhaled anti-inflammatory therapy to maintain sputum eosinophil counts to <3% have resulted in fewer asthma exacerbations (Green et al., 2002). Symptomatic asthmatics with recalcitrant sputum eosinophilia on standard therapy have also improved after monoclonal antibody therapy (mepolizumab) that depletes airway eosinophils (Nair et al., 2009; Haldar et al., 2009).

To date the only accurate and reliable method to identify eosinophilic asthmatics has been limited to procurement of induced sputum samples from patients (Molfino, 2012). The sputum induction procedure is a tedious and complex process that requires skilled technicians and equipment that are not readily available in clinical practice. Even with these shortcomings, induced sputum remains the gold standard for assessing the cellular inflammatory processes that occur in asthma (Lieberman, 2007). A panel convened from the National Institutes of Health and federal agencies to propose biomarkers to assess disease progression and response to treatment has recommended 2% eosinophils in sputum as the cut-off for classifying patients as sputum eosinophilic asthmatics (Szefler et al., 2012).

Other less invasive and simpler tests such as exhaled nitric oxide (eNO), also referred to as Fraction of Exhaled Nitric Oxide ($FE_{NO}$), and peripheral blood eosinophils counts among others have been studied in an attempt to find an alternative predictive markers for sputum eosinophil counts (Turner, 2007; Lieberman, 2007). None of these potential predictive markers alone have been found to have a strong enough diagnostic value to be useful in the clinical setting (Stick, 2009).

In 2011, the American Thoracic Society (ATS) has issued issues guidelines on the use of fractional exhaled nitric oxide ($FE_{NO}$) to identify eosinophilic asthmatics. According to the ATS official guidelines, $FE_{NO}$>50 parts per billion (ppb) (>35 ppb in children) indicates eosinophilic inflammation and, in symptomatic patients, responsiveness to corticosteroids are likely (Dweik et al., 2011). However, a recent systematic review and meta-analysis about the tailoring of asthma treatment based on eosinophilic markers (exhaled nitric oxide or sputum eosinophils), concluded that tailoring of asthma treatment based on $FE_{NO}$ levels was not effective in improving asthma outcomes in children and adults (Petsky et al., 2012). The same study also concluded that it was not practical to use either sputum analysis (due to technical expertise required) or $FE_{NO}$ in everyday clinical practice (Petsky et al., 2012).

Accordingly, there is an unmet need for validated methods and tools that can be used to screen eosinophilic asthmatics for enrollment in clinical trials and in clinical diagnosis for prescribing appropriate medications. In addition, there is an unmet need for methods and tools to adequately classify patients suffering from pulmonary diseases in order to identify the appropriate therapies.

BRIEF SUMMARY OF THE DISCLOSURE

The present disclosure provides methods and systems for diagnosing and treating a subject having a pulmonary disease or disorder comprising using classifications methods comprising at least one predictor for class prediction; wherein at least one predictor comprises a ratio of two cellular components from a complete blood cell count (CBC) with differential and wherein the classification method does not use induced sputum eosinophil count as a predictor. The application of the classification methods of the present disclosure comprises calculating a set of intermediate scores (e.g., Score 1 and Score 2) from a pair of equations, each of which can comprise at least one predictor comprising a white blood cell ratio. In turn, the intermediate scores are used to determine or calculate a diagnostic score.

For example:

$$\text{Intermediate Score 1} = \text{Predictor } A \ldots \text{Predictor } Z \quad \text{(Equation 1)}$$

$$\text{Intermediate Score 2} = \text{Predictor } 1 \ldots \text{Predictor } N \quad \text{(Equation 2)}$$

wherein the diagnostic score is, e.g., (Intermediate Score 2−Intermediate Score 1) or a decision rule such as "If Intermediate Score 2<Intermediate Score 1 then . . . [e.g., apply a certain treatment]."

The disclosure provides a method of treating a patient having a pulmonary disease or disorder comprising (a) measuring a white blood cell count in a sample taken from a patient having a pulmonary disease or disorder to calculate a white blood cell ratio; (b) calculating a diagnostic score from the white blood cell ratio, wherein the diagnostic score indicates whether the patient will benefit from administration of a therapy; and, (c) administering the therapy to the patient if the diagnostic score indicates that the patient will benefit from administration of the therapy. Also provided is a method of treating a patient having a pulmonary disease or disorder comprising (a) calculating a diagnostic score from a white blood cell ratio measured from a white blood cell count obtained from a sample taken from a patient having a pulmonary disease or disorder; (b) determining from the diagnostic score whether the patient will benefit from administration of a therapy; and, (c) administering the therapy to the patient if the diagnostic score indicates that the patient will benefit from administration of the therapy.

The disclosure also provides a method of treating a patient having a pulmonary disease or disorder comprising (a) measuring a white blood cell count in a sample taken from a patient having a pulmonary disease or disorder to calculate a white blood cell ratio; (b) calculating a diagnostic score from the white blood cell ratio, wherein the diagnostic score indicates whether the patient will benefit from administration of a therapy; and, (c) instructing a healthcare provide to administer the therapy to the patient if the diagnostic score indicates that the patient will benefit from administration of the therapy. Also provided is a method of treating a patient having a pulmonary disease or disorder comprising (a) calculating a diagnostic score from a white blood cell ratio measured from a white blood cell count obtained from a sample taken from a patient having a pulmonary disease or disorder; (b) determining from the diagnostic score whether the patient will benefit from administration of a therapy; and, (c) instructing a healthcare provider to administer the therapy to the patient if the diagnostic score indicates that the patient will benefit from administration of the therapy.

Also provided in the present disclosure is a method of treating a patient having a pulmonary disease or disorder comprising (a) determining from a diagnostic score calculated from a white blood cell ratio measured from a white blood cell count obtained from a sample taken from a patient having a pulmonary disease or disorder whether the patient will benefit from administration of a therapy; and, (b) administering the therapy to the patient if the diagnostic score indicates that the patient will benefit from administration of the therapy. The disclosure also provides a method of treating a patient having a pulmonary disease or disorder comprising (a) submitting a sample taken from a patient having a pulmonary disease or disorder for measurement of a white blood cell count, calculation of a white blood cell ratio from said cell count, determination of a diagnostic score, or combination thereof, wherein the diagnostic score is calculated from the white blood cell count or the white blood cell ratio; and, (b) administering the therapy to the patient if the diagnostic score indicates that the patient will benefit from administration of the therapy.

The disclosure provides a method of treating a patient having a pulmonary disease or disorder comprising (a) submitting a sample taken from a patient having a pulmonary disease or disorder for measurement of a white blood cell count, calculation of a white blood cell ratio from said white blood cell count, determination of a diagnostic score, or combination thereof, wherein the diagnostic score is calculated from the white blood cell count or the white blood cell ratio; and, (b) instructing a healthcare provide to administer the therapy to the patient if the diagnostic score indicates that the patient will benefit from administration of the therapy.

The disclosure also provides diagnostic methods. In this respect, the disclosure provides a method of diagnosing whether a patient is in need of therapy to treat a pulmonary disease or disorder, comprising (a) measuring a white blood cell count in a sample taken from the patient to calculate a white blood cell ratio; (b) calculating a diagnostic score from the white blood cell ratio, wherein the diagnostic score indicates whether the patient has a pulmonary disease or disorder; and (c) instructing a healthcare provider to provide therapy to treat a pulmonary disease or disorder if the patient is in need thereof. Also provided is a method of diagnosing whether a patient is in need of therapy to treat a pulmonary disease or disorder, comprising (a) calculating a diagnostic score from a white blood cell ratio measured from a white blood cell count obtained from a sample taken from the patient; (b) determining from the diagnostic score whether the patient has a pulmonary disease or disorder; and, (c) providing therapy to treat a pulmonary disease or disorder if the patient is in need thereof.

Also provided is a method of diagnosing whether a patient is in need of therapy to treat a pulmonary disease or disorder comprising (a) determining whether the patient has a pulmonary disease or disorder from a diagnostic score calculated from a white blood cell ratio measured from a white blood cell count obtained from a sample taken from the patient; and, (b) providing therapy or instructing a healthcare provider to provide therapy to treat a pulmonary disease or disorder if the patient is in need thereof. The disclosure also provides a method of diagnosing whether a patient is in need of therapy to treat a pulmonary disease or disorder comprising (a) submitting a sample taken from the patient for measurement of a white blood cell count, calculation of a white blood cell ratio from said cell count, determination of a diagnostic score, or combination thereof, wherein the diagnostic score is calculated from the white blood cell count or the white blood cell ratio; and wherein the diagnostic score indicates whether the patient has a pulmonary disease or disorder; and, (b) providing therapy or instructing a healthcare provider to provide therapy to treatment a pulmonary disease or disorder if the patient is in need thereof.

The present disclosure also provides methods for monitoring the efficacy of a therapy. In this respect, the disclosure provides a method of monitoring the efficacy of a therapy administered to a patient having a pulmonary disease or disorder comprising (a) calculating a first diagnostic score from a first white blood cell ratio measured from a white blood cell count obtained from a first sample taken from a patient having a pulmonary disease or disorder; (b) administering a therapy to the patient to treat the pulmonary disease or disorder; (c) calculating a second diagnostic score from a second white blood cell ratio measured white blood cell count obtained from a second sample taken from the patient; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score. Also provided is a method of monitoring the efficacy of a therapy administered to a patient having a pulmonary disease or disorder comprising (a) submitting a first sample taken from a patient having a pulmonary disease or disorder for measurement of a white blood cell count, calculation of a white blood cell ratio from said white blood cell count, determination of a first diagnostic score, or combination thereof, wherein the first diagnostic score is calculated from the white blood cell count or the white blood cell ratio; (b) administering a therapy to the patient to treat the pulmonary disease or disorder; (c) submitting a second sample taken from a patient having a pulmonary disease or disorder for measurement of a white blood cell count, calculation of a white blood cell ratio from said white blood cell count, determination of a second diagnostic score, or combination thereof, wherein the second diagnostic score is calculated from the white blood cell count or the white blood cell ratio; (d) comparing the first diagnostic score and the second diagnostic score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

Also provided is a method of monitoring the efficacy of a therapy administered to a patient having a pulmonary disease or disorder comprising (a) calculating a first diagnostic score from a first white blood cell ratio measured from a white blood cell count obtained from a first sample taken from a patient having a pulmonary disease or disorder; (b) administering a therapy to the patient to treat the pulmonary disease or disorder; (c) submitting a second sample taken from a patient having a pulmonary disease or disorder for measurement of a white blood cell count, calculation of a white blood cell ratio from said white blood cell count, determination of a second diagnostic score, or combination thereof, wherein the second diagnostic score is calculated from the white blood cell count or the white blood cell ratio; (d) comparing the first diagnostic score and the second diagnostic score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score. Also provided is a method of monitoring the efficacy of a therapy administered to a patient having a pulmonary disease or disorder comprising (a) submitting a first sample taken from a patient having a pulmonary disease or disorder for measurement of a white blood cell count, calculation of a white blood cell ratio from said white blood cell count, determination of a first diagnostic score, or combination thereof, wherein the first diagnostic score is calculated from the white blood cell count or the white blood cell ratio; (b) administering a therapy to the patient to treat the pulmonary disease or disorder; (c) calculating a second diagnostic score from a second white blood cell ratio measured from a white blood cell count obtained from a second sample taken from a patient having a pulmonary disease or disorder; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

Also provided is a method of monitoring the efficacy of a therapy administered to a patient having a pulmonary disease or disorder comprising (a) calculating a first diagnostic score from a first white blood cell ratio measured from a white blood cell count obtained from a first sample taken from a patient having a pulmonary disease or disorder; (b) instructing a healthcare provider to administer a therapy to the patient to treat the pulmonary disease or disorder; (c) calculating a second diagnostic score from a second white blood cell ratio measured from a white blood cell count obtained from a second sample taken from the patient; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

The present disclosure also provides a computer-readable medium containing instructions for identifying a patient as a candidate for a therapy to treat a pulmonary disease or disorder, wherein execution of the program instructions by one or more processors of a computer system causes the one or more processors to carry out the steps of (a) processing inputted data obtained from a white blood cell count obtained from a sample obtained from the patient; and (b) calculating a diagnostic score from a white blood cell ratio obtained from the processed inputted data; wherein the diagnostic score identifies the patient as a candidate for a therapy to treat the pulmonary disease or disorder. Also provided is a computer-readable medium containing instructions for identifying a candidate therapy to treat a pulmonary disease or disorder, wherein execution of the program instructions by one or more processors of a computer system causes the one or more processors to carry out the steps of (a) processing inputted data obtained from a white blood cell count obtained from a sample obtained from the patient; and (b) calculating a diagnostic score from a white blood cell ratio obtained from the processed inputted data; wherein the diagnostic score identifies the candidate therapy to treat the pulmonary disease or disorder.

Also provided is a computer-readable medium containing instructions for diagnosing a pulmonary disease or disorder in a patient to provide a therapy to said patient, wherein execution of the program instructions by one or more processors of a computer system causes the one or more processors to carry out the steps of (a) processing inputted data obtained from a white blood cell count obtained from a sample obtained from the patient; and (b) calculating a diagnostic score from a white blood cell ratio obtained from the processed inputted data; wherein the diagnostic score diagnoses the pulmonary disease or disorder in the patient. Also provided is a computer-readable medium containing instructions for managing the administration of a therapy to treat a pulmonary disease or disorder by a healthcare provider, wherein execution of the program instructions by one or more processors of a computer system causes the one or more processors to carry out the steps of (a) processing inputted data obtained from a white blood cell count obtained from a sample obtained from the patient; (b) calculating a diagnostic score from a white blood cell ratio obtained from the processed inputted data; wherein the diagnostic score is used by the healthcare provider for managing the treatment of the pulmonary disease or disorder.

Also provided is a computer-readable medium containing instructions for managing the administration of a therapy of a pulmonary disease or disorder by a healthcare benefits provider, wherein execution of the program instructions by one or more processors of a computer system causes the one or more processors to carry out the steps of (a) processing inputted data obtained from a white blood cell count obtained from a sample obtained from the patient; and (b) calculating a diagnostic score from a white blood cell ratio obtained from the processed inputted data; wherein the diagnostic score is used by the healthcare benefits provider for managing the treatment of the pulmonary disease or disorder.

In some aspects, the pulmonary disease in the disclosed methods or computer-readable media is a chronic pulmonary disease. In some aspects, the pulmonary disease in the disclosed methods or computer-readable media is selected from the group consisting of asthma and chronic pulmonary disease (COPD). In other aspects, the pulmonary disease in the disclosed methods or computer-readable media is a pulmonary eosinophilic disease. In other aspects, the pulmonary eosinophilic disease in the disclosed methods or computer-readable media is eosinophilic asthma.

In some aspects, the therapy in the disclosed methods or computer-readable media comprises the administration of a therapeutic agent. In other aspects, the therapeutic agent in the disclosed methods or computer-readable media is a biologic agent. In some aspects, the therapeutic agent in the disclosed methods or computer-readable media is a small molecule drug. In other aspects, the biologic agent in the disclosed methods or computer-readable media is an antibody or an antigen-binding fragment thereof. In some aspects, the antibody or antigen-binding fragment thereof in the disclosed methods or computer-readable media is an anti-IgE antibody. In other aspects, the antibody or antigen-binding fragment thereof in the disclosed methods or computer-readable media is an anti-cytokine antibody. In some aspects, the antibody or antigen-binding fragment thereof in the disclosed methods or computer-readable media is an anti-cytokine receptor antibody. In other aspects, the anti-cytokine antibody in the disclosed methods or computer-readable media is an anti-interleukin antibody. In other aspects, the anti-cytokine receptor antibody in the disclosed methods or computer-readable media is an anti-interleukin receptor antibody. In some aspects, the anti-interleukin antibody in the disclosed methods or computer-readable media is an anti-IL5 antibody. In some aspects, the anti-interleukin receptor antibody in the disclosed methods or computer-readable media is an anti-IL-5R antibody. In specific aspects, the anti-IL5 antibody in the disclosed methods or computer-readable media is selected from the group consisting of reslizumab, mepolizumab, omalizumab, and any combination thereof. In specific aspects, the anti-IL-5R antibody in the disclosed methods or computer-readable media is benralizumab. In other specific aspects, the anti-IL5R antibody in the disclosed methods or computer-readable media is not benralizumab. In some aspects, the anti-IL5R antibody in the disclosed methods or computer-readable media binds the same epitope as benralizumab.

In some aspects, the small molecule drug in the disclosed methods or computer-readable media is a corticosteroid. In other aspects, the small molecule drug in the disclosed methods or computer-readable media is not a corticosteroid. In some aspects, the patient in the disclosed methods or computer-readable media has an eosinophil sputum count of at least about 2%. In other aspects, the patient in the disclosed methods or computer-readable media has an eosinophil sputum count of at least about 8%. In other aspects, the patient in the disclosed methods or computer-readable media has a $FE_{NO}$ of at least about 50 ppb.

In some aspects, the sample in the disclosed methods or computer-readable media is a blood, serum, or plasma sample. In other aspects, the white blood cell count in the disclosed methods or computer-readable media is a complete blood count (CBC) with differentials. In some aspects, the white blood cell count in the disclosed methods or computer-readable media comprises an eosinophil count, a neutrophil count, a lymphocyte count, an eosinophil precursor count, a basophil precursor count, or any combination thereof. In other aspects, the white blood cell ratio in the disclosed methods or computer-readable media is a ratio between an eosinophil count and a second white blood cell type count.

In some aspects, the white blood cell ratio in the disclosed methods or computer-readable media is an eosinophil count to lymphocyte count ratio (blood eosinophil/blood lymphocyte ratio). In other aspects, the white blood cell ratio in the disclosed methods or computer-readable media is an eosinophil count to a neutrophil count ratio (blood eosinophil/blood neutrophil ratio). In some aspects, the diagnostic score in the disclosed methods or computer-readable media is the variance between two intermediate scores (Score 1 and Score 2), wherein the calculation of Score 1 and Score 2 comprises at least one predictor comprising a white blood cell ratio.

In other aspects, the calculation of Score 1 and Score 2 in the disclosed methods or computer-readable media comprises a predictor not comprising a white blood cell ratio or a function thereof. In some aspects, at least one predictor in the disclosed methods or computer-readable media comprises a function of a white blood cell ratio. In some aspects, the function is a natural logarithm. In other aspects, at least one predictor in the disclosed methods or computer-readable media comprises a sum, difference, ratio or product of a coefficient to a while blood cell ratio or a function thereof. In some aspects, the calculation of Score 1 and the calculation of Score 2 in the disclosed methods or computer-readable media comprises the same number of predictors, for example one predictor, two predictors or at least three predictors.

In other aspects, each predictor in the disclosed methods or computer-readable media comprises a white blood cell ratio. In some aspects, each predictor in the disclosed methods or computer-readable media comprises the same white blood cell ratio. In other aspects, each predictor in the disclosed methods or computer-readable media comprises a different white blood cell ratio. In some aspects, one predictor in the disclosed methods or computer-readable media comprises a blood eosinophil/blood lymphocyte ratio. In other aspects, one predictor in the disclosed methods or computer-readable media comprises a blood eosinophil/blood neutrophil ratio. In some aspects, one predictor in the disclosed methods or computer-readable media comprises a blood eosinophil/white blood cell ratio. In other aspects, one predictor in the disclosed methods or computer-readable media comprises a blood eosinophil/blood neutrophil ratio and one blood eosinophil/blood lymphocyte ratio.

In some aspects, Score 1 in the disclosed methods or computer-readable media is calculated according to the formula $$\text{Score }1=a+[b\times\text{blood eosinophil/blood lymphocyte}]-[c\times\text{natural log(blood eosinophil/blood neutrophil)}]$$

and Score 2 is calculated according to the formula:

$$\text{Score }2=d+[e\times\text{blood eosinophil/blood lymphocyte}]-[f\times\text{natural log(blood eosinophil/blood neutrophil)}],$$

wherein:
(a) a is between about −74 and about −6;
(b) b is between about 45 and about 412;
(c) c is between about −38 and about −2;
(d) d is between about −95 and about −10;
(e) e is between about 65 and about 473; and,
(f) f is between about −39 and about −2,
wherein a Score 1≤Score 2 indicates that the patient has an eosinophilic disease or disorder. In some aspects, the coefficients in the disclosed method are: a is about −10, b is about 70, c is about 4, d is about −15, e is about 101, and f is about 4. In some aspects, the coefficients in the disclosed method are: a is −9.5243233, b is 70.0974823, c is 3.7789926, d is −14.5853365, e is 101.2197561, and f is 3.9567050, In other aspects, at least one predictor in the disclosed methods or computer-readable media comprises a $FE_{NO}$ measurement, a BMI measurement, or an analyte measurement. In some aspects, the analyte in the disclosed methods or computer-readable media is periostin. In other aspects, the at least one predictor in the disclosed methods or computer-readable media comprises a $FE_{NO}$ measurement. In some aspects, the calculation of Score 1 and the calculation of Score 2 in the disclosed methods or computer-readable media comprises the same number of predictors. In other aspects, the calculation of Score 1 and the calculation of Score 2 in the disclosed methods or computer-readable media each comprises two predictors. In some aspects, one of the two predictors in the disclosed methods or computer-readable media comprises a white blood cell ratio and the other predictor comprises a $FE_{NO}$ measurement. In some aspects, the collection of the sample to measure the white blood cell ratio and the $FE_{NO}$ measurement in the disclosed methods or computer-readable media are performed on the same day. In other aspects, the white blood count and $FE_{NO}$ measurement in the disclosed methods or computer-readable media are performed on the same day. In some aspects, the white blood cell ratio in the disclosed methods or computer-readable media is a blood eosinophil/blood lymphocyte ratio.

In some aspects, Score 1 in the disclosed methods or computer-readable media is calculated according to the formula $$\text{Score } 1 = a' + (b' \times FE_{NO} \text{ ppb}) - [c' \times \text{natural log(blood eosinophil/blood lymphocyte)}]$$

and Score 2 is calculated according to the formula:

$$\text{Score } 2 = d' + (e' \times FE_{NO} \text{ ppb}) - [f' \times \text{natural logarithm (blood eosinophil/blood lymphocyte)}]$$

wherein:
(a) a' is between about −14 and about −4;
(b) b' is between about 0.01 and about 0.16;
(c) c' is between about −10 and about −2.2;
(d) d' is between about −10 and about −3.2;
(e) e' is between about 0.035 and about 0.17; and,
(f) f' is between about −8 and about −1.5,
wherein a Score 1≤Score 2 indicates that the patient has an eosinophilic disease or disorder. In some aspects, the coefficients in the disclosed method are: a' is about −5, b' is about 0.03, c' is about 2.5, d' is about −3.5, e' is about 0.05, and f' is about 2. In some aspects, the coefficients in the disclosed method are: a' is −4.6368456, b' is 0.0300382, c' is 2.5409793, d' is −3.6017103, e' is 0.0559650, and f' is 1.7349461, In other aspects, the disclosed methods or computer-readable media further comprise determining that the patient has a $FE_{NO}$ measurement of at least 50 ppb.

In some aspects, the steps in the method are repeated or the instructions for execution in the computer-readable medium are executed iteratively using measurements from samples collected at least one week apart. In other aspects, the steps in the method are repeated or the instructions for execution in the computer-readable medium are executed iteratively using measurements from samples collected at least two weeks apart. In some aspects, the white blood cell count in the disclosed methods or computer-readable media comprises the averaged values of at least two white blood cell counts obtained from samples collected at least one week apart. In other aspects, the white blood cell count in the disclosed methods or computer-readable media comprises the averaged values of at least two white blood cell counts obtained from samples collected at least one week apart.

In some aspects, the patient in the disclosed methods or computer-readable media has received constant inhaled medication for at least 6 weeks prior to sample collection. In other aspects, the patient in the disclosed methods or computer-readable media has received constant oral medication for at least 6 weeks prior to sample collection. In some aspects, the samples in the disclosed methods or computer-readable media are analyzed within 4 to 10 hours from collection.

BRIEF DESCRIPTION OF THE DRAWINGS

FIG. 2 shows the moderate correlation between two variables arbitrarily designated as "variable X" and "variable Y" (oval arrangement) in a simulated data set (Pearson's r=0.47).

FIG. 7 shows the generic ELEN Index equations and 95% CI of model coefficients. The 95% CI of model coefficients is based upon 10,000 bootstrap re-sampling.

DETAILED DESCRIPTION

Figure 1A:
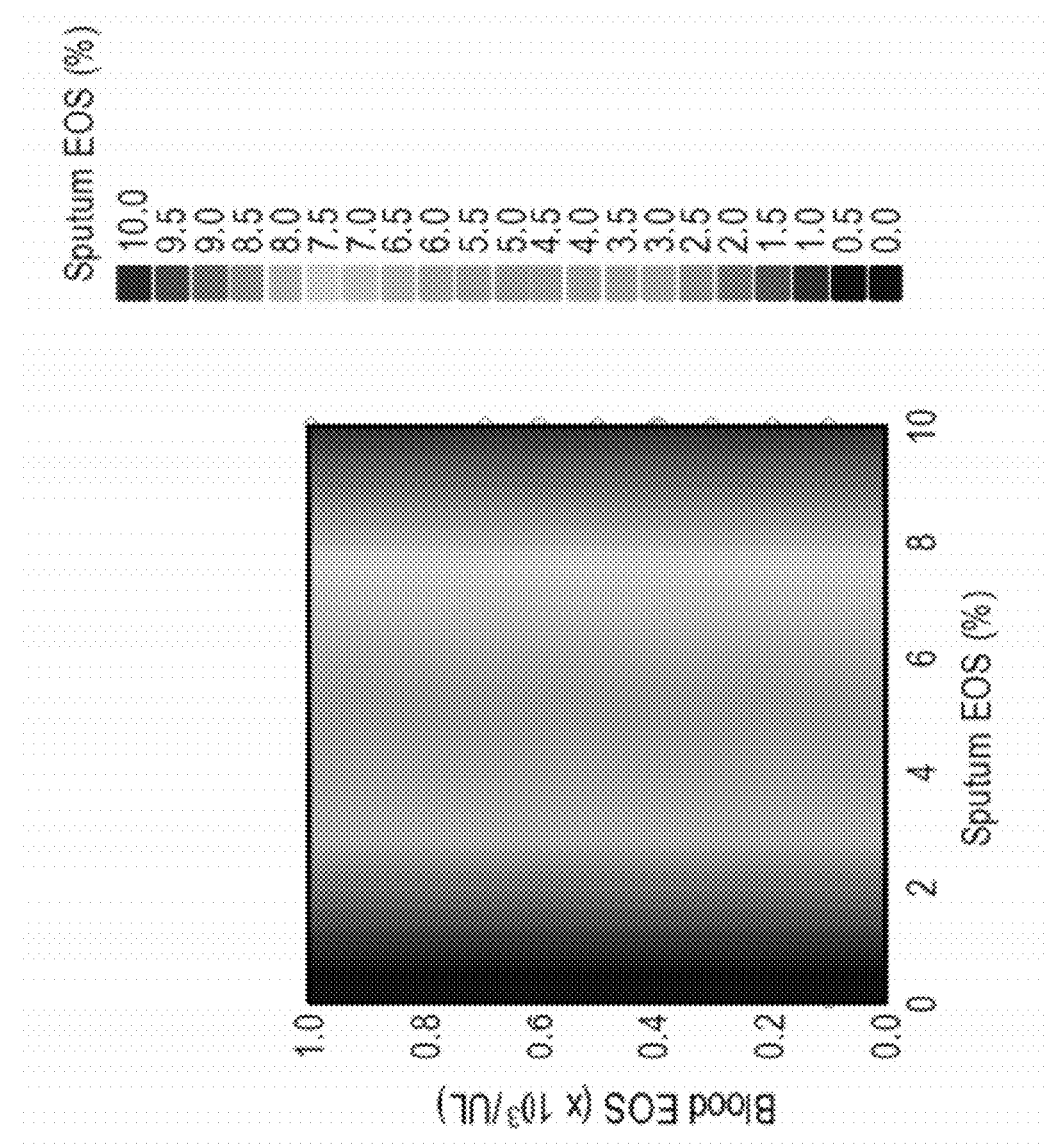
FIG. 1A shows a heatmap correlating Sputum EOS % with blood eosinophil counts.

The present disclosure provides methods and systems for diagnosing and treating a subject as having a pulmonary disease or disorder comprising using an objective, probabilistic, multivariate statistical model with at least one predictor for class prediction; wherein at least one predictor comprises a ratio of two cellular components from a complete blood cell count (CBC) with differential and wherein the model does not use induced sputum eosinophil count as a predictor. In certain embodiments, the model is based on Fisher's Linear Discriminant Analysis.

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

As used herein, the term "pulmonary disease or disorder" refers to any pathology affecting at least in part the lungs or respiratory system. The term encompasses obstructive and non-obstructive pulmonary diseases or disorders, for instance, asthma, emphysema, chronic obstructive pulmonary disease, pneumonia, tuberculosis, mixed connective tissue disease, and fibrosis in all its forms. The term applies particularly to pulmonary eosinophilic diseases or disorders, e.g., eosinophilic asthma.

The term "pulmonary eosinophilic disease or disorder" is used herein refers to a pulmonary disease or disorder characterized by elevated levels or eosinophil counts in the lung. Elevated levels of eosinophils in the lung can be diagnosed by determining the eosinophil counts in induced sputum (e.g., Sputum EOS %). Typically, the normal range is ≤2.0% as determined by Belda et al. (2000). In one embodiment, a pulmonary eosinophilic disease or disorder can be a pulmonary disease or disorder characterized by a sputum eosinophil count of, ≥2%, ≥3%, ≥4%, ≥5%, ≥6%, ≥7%, ≥8%, ≥9%, or ≥10%. In a specific embodiment, a pulmonary eosinophilic disease or disorder is a disease or disorder characterized by a sputum eosinophil count of ≥2%.

As used herein the terms "treat," "treatment," or "treatment of" (e.g., in the phrase "treating a patient having a pulmonary disease or disorder") refers to reducing the potential for a pulmonary disease or disorder, reducing the occurrence of the pulmonary disease or disorder, and/or a reduction in the severity of the pulmonary disease or disorder, preferably, to an extent that the subject no longer suffers discomfort and/or altered function due to it. For example, treating can refer to the ability of a therapy when administered to a subject, to prevent a pulmonary disease or disorder from occurring and/or to cure or to alleviate pulmonary disease symptoms, signs, or causes (for example, a relative reduction in asthma exacerbations when compared to untreated patients). Treating also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

The present disclosure provides methods and systems providing therapeutic benefit in the treatment of a pulmonary disease or disorder. A therapeutic benefit is not necessarily a cure for a particular pulmonary disease or disorder, but rather encompasses a result which most typically includes alleviation of the pulmonary disease or disorder or increased survival, elimination of the pulmonary disease or disorder, reduction of a symptom associate with the pulmonary disease or disorder, prevention or alleviation of a secondary disease, disorder or condition resulting from the occurrence of a primary pulmonary disease or disorder, and/or prevention of the pulmonary disease or disorder.

The terms "subject" or "patient" as used herein refer to any subject, particularly a mammalian subject, for whom diagnosis, prognosis, or therapy of a pulmonary disease or disorder is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having pulmonary disease or disorder" includes subjects, such as mammalian subjects, that would benefit from the administration of a therapy, imaging or other diagnostic procedure, and/or preventive treatment for that pulmonary disease or disorder.

In some aspects of the present disclosure, a subject is a naëve subject. A naëve subject is a subject that has not been administered a therapy, for example a therapeutic agent. In some aspects, a naëve subject has not been treated with a therapeutic agent prior to being diagnosed as having a pulmonary disease or disorder, for example, an eosinophilic disease or disorder. In some aspects, a naëve subject has not been treated with a therapeutic agent capable to modulate the level or activity of eosinophil granulocytes prior to being diagnosed as having a pulmonary eosinophilic disease or disorder. In another aspect, a subject has received therapy and/or one or more doses of a therapeutic agent (e.g., a therapeutic agent capable of modulating the level or activity of eosinophil granulocytes) prior to being diagnosed as having a pulmonary disease or disorder (e.g., an eosinophilic disease or disorder). In some aspects, a subject has received at least one therapeutically effective dose of corticosteroids. In other aspects, a subject has received at least one therapeutically effective dose of an antibody (e.g., anti-IL-5 antibody and anti-IL-5R antibody) capable of modulating the level or activity of eosinophil granulocytes.

The term "therapy" as used herein includes any means for curing, mitigating, or preventing a pulmonary disease or disorder, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of a pulmonary disease or disorder, for example, an eosinophilic disease or disorder. In some aspects, the term "therapy" refers to administering a therapeutically effective amount of a therapeutic agent that is capable of reducing tissue eosinophil numbers or tissue eosinophil activity in a patient in need thereof.

The term "therapeutic agent" as used herein refers to any therapeutically active substance that is administered to a subject having a pulmonary disease or disorder to produce a desired, usually beneficial, effect. The term therapeutic agent includes, e.g., classical low molecular weight therapeutic agents commonly referred to as small molecule drugs and biologics including but not limited to: peptides, lipids, protein drugs, protein conjugate drugs, enzymes, oligonucleotides, ribozymes, genetic material, prions, virus, bacteria, and eukaryotic cells. A therapeutic agent can also be a pro-drug, which metabolizes into the desired therapeutically active substance when administered to a subject. In addition, a therapeutic agent can be pharmaceutically formulated. A therapeutic agent can also be a radioactive isotope or agent activated by some other form of energy such as light or ultrasonic energy, or by other circulating molecules that can be systemically administered. In some aspects, the term "therapeutic agent" refers to therapeutically active substance that is capable of reducing tissue eosinophil numbers or tissue eosinophil activity in a patient in need thereof.

A "therapeutically effective" amount as used herein is an amount of therapeutic agent that provides some improvement or benefit to a subject having a pulmonary disease or disorder. Thus, a "therapeutically effective" amount is an amount that provides some alleviation, mitigation, and/or decrease in at least one clinical symptom of the pulmonary disease or disorder. Clinical symptoms associated with the pulmonary diseases and disorders that can be treated by the methods and systems of the disclosure are well-known to those skilled in the art. Further, those skilled in the art will appreciate that the therapeutic effects need not be complete or curative, as long as some benefit is provided to the subject. In some aspects, the term "therapeutically effective" refers to an amount of a therapeutic agent therapeutic agent that is capable of reducing tissue eosinophil numbers or tissue eosinophil activity in a patient in need thereof.

As used herein, a "sufficient amount" or "an amount sufficient to" achieve a particular result in a patient having a pulmonary disease or disorder refers to an amount of a therapeutic agent (e.g., an antibody) that is effective to produce a desired effect, which is optionally a therapeutic effect (i.e., by administration of a therapeutically effective amount). In some aspects, such particular result is a reduction in tissue eosinophil numbers or tissue eosinophil activity in a patient in need thereof.

The term "sample" as used herein includes any biological fluid or issue, such as whole blood, serum, muscle, saliva obtained from a subject. Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. In some specific aspects, that sample is blood or a fraction thereof, muscle, skin, or a combination thereof. Samples can be obtained by any means known in the art.

In order to apply the methods and systems of the disclosure, samples from a patient can be obtained before or after the administration of a therapy to treat a pulmonary disease or disorder. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions which directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.MedImmune As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat a pulmonary disease or disorder. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., a therapeutic agent that treats a pulmonary disease or disorder such a eosinophilic asthma), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, The above enumerated actions can be performed by a healthcare provider, healthcare benefits provider, or patient automatically using a computer-implemented method (e.g., via a web service or stand-alone computer system).

The term "CBC with differential" as used herein refers to complete blood cell count (CBC) with white blood cell (WBC) differentials. The term "white blood cell" includes, e.g., neutrophils, lymphocytes, monocytes, eosinophils, and basophils. The terms "eosinophil" and "eosinophils" can be abbreviated as "EOS" herein.

The term "$FE_{NO}$" Fraction of Exhaled Nitric Oxide ($FE_{NO}$) can also be referred to as exhaled nitric oxide (eNO).

The term "COPD" as used herein refers to chronic obstructive pulmonary disease. The term "COPD" includes two main conditions: emphysema and chronic obstructive bronchitis.

The terms vital capacity (VC), forced vital capacity (FVC), forced expiratory volume (FEV), forced expiratory flow (FEF), maximal voluntary ventilation (MVV), positive predictive value (PPV), and negative predictive value (NPV) are used herein.

As used herein, the term "tube" refers to any container or support suitable for collecting a sample, for example, a blood sample. Thus, the term "tube" encompasses, for example, a collection tube, a vial, another suitable vessel, a bottle, a bag, an absorbent or non-absorbent collection surface (e.g., a glass slide), or a chip. The term also encompasses a plurality of containers or supports.

The terms "ELEN Index" and "ELEN Index method" as used herein refer to the predictive model disclosed infra in which two white blood cell ratios (Eosinophil/Lymphocyte and Eosinophil/Neutrophil) are used to classify a patient having a pulmonary disease or disorder.

The term "EL-$FE_{NO}$ Index" and "EL-$FE_{NO}$ Index method" as used herein refer to the predictive model disclosed infra in which one white blood cell ratios (Eosinophil/Lymphocyte) and a $FE_{NO}$ measurement are used to classify a patient having a pulmonary disease or disorder.

The term "Intermediate Score" as used herein refers to a score (e.g., a Score 1 or a Score 2) calculated from at least one predictor, which in turn is used to calculate a Diagnostic Score. As used in the claims, the terms "Score 1" and "Score 2" refer in general to any Intermediate Score, and are not limited to the scores derived from the application of the ELEN Index method or any other classification method disclosed herein (e.g., the EL-$FE_{NO}$ method).

The term "Diagnostic Score" as used herein refers to the relationship between Intermediate Scores (e.g., Score 1 and Score 2) used to classify a patient as having a certain pulmonary disease or disorder. A Diagnostic Score can be expressed as a decision rule (e.g., "if Score 1≤Score 2 then . . . " or "if Score 1>Score 2 then . . . "), as a qualifier (e.g., if Score 1≤Score 2 then the Diagnostic Score would be "positive" or "+," and if Score 1>Score 2 then the Diagnostic Score would be "negative" or "−"), or as a numeric value (e.g., calculated by subtracting Score 1 from Score 2).

Introduction

To address the critical need for a robust and easily applicable test to identify subjects having a pulmonary disease or disorder (e.g., patients having a pulmonary eosinophilic disease or disorder), the present disclosure provides a statistical approach using predictive discriminant analysis. The classification methods disclosed herein utilize ratios calculated from several cellular components obtained from a white blood cell count (for example, a routine CBC with differential).

These classification methods were developed using a data sample of asthmatics with measurements of both sputum eosinophil counts and CBC with differential. Of the various cellular components studied in peripheral blood, a statistical predictive model (the ELEN Index method) comprised of three white blood cell populations (eosinophils, neutrophils, and lymphocytes) provided good discrimination between sputum eosinophilic and non-eosinophilic asthma.

In addition, in certain aspects to improve the sensitivity of the method, a two-pass classification method was developed which used a white blood cell ratio-based method (the ELEN Index method) in conjunction with a subject's Fraction of Exhaled Nitric Oxide ($FE_{NO}$) measurement.

Also, a third classification method was developed that incorporated $FE_{NO}$ measurements and white blood cell ratios in a single statistical predictive model (the EL-$FE_{NO}$ method). These classification methods provide as a simple, easily obtained and reasonable alternative to induced sputum for classifying patients having a pulmonary disease or disorder, for example, identifying eosinophilic asthmatics for screening and diagnostic purposes.

A cut-off approach based on absolute values, e.g., sputum EOS % cutoff, is used as the gold standard for prediction and classification in pulmonary diseases and disorders such as eosinophilic asthma. In one aspect, the EOS % cutoff point to classify a patient as eosinophilic is 2% or greater sputum eosinophils. EOS % cutoff points of 1%, 2%, 2.5%, and 3% sputum eosinophils have been reported as discriminating between eosinophilic and non-eosinophilic patients. See, e.g., Green et al., 2002 and Jayaram et al., 2006. Belda et al., 2000 showed that the mean+2 standard deviations for sputum EOS % in healthy subjects is 2.2%. To date, attempts to predict and classify eosinophilic asthma have investigated the correlations of individual measures (such as blood eosinophil counts and $FE_{NO}$ with sputum EOS %.

The classification methods provided herein permit a complex pathology such as eosinophilic asthma to be diagnosed accurately by using broadly applicable multifactorial predictive models versus relying on univariate cutoffs, which often vary depending upon differences observed in individual studies. The predicting variables in the disclosed classification methods are biologically meaningful measures that are relatively easy to obtain while having high diagnostic value in clinical applications. For example, using multiple white blood cell populations from CBC with differential as predicting variable subsets is more biologically meaningful than using counts of single cell types, e.g., blood eosinophils or neutrophils. Furthermore, we have found it is more important to look at relative changes in cell populations in a white blood cell count (i.e., ratios between different cell populations in the white blood cell count) in order to identify predictors for classifying patients suffering from pulmonary diseases or disorders, e.g., eosinophilic asthma.

Thus, by using ratios comprised of dynamic cell populations, whose kinetics can be driven by various underlying biological and clinical conditions, as predictors in multivariate models, these classification methods have substantially increased the prediction accuracy in classifying eosinophilic and non-eosinophilic asthmatics. The use of ratios in multivariate statistical models is a novel approach because previous attempts to date used single measures one at a time, such as using blood eosinophil cutoffs at various levels (e.g., 300 cells/mm$^3$, cited in Lieberman, 2007; 250 cells/mm$^3$, Nadif et al., 2009); $FE_{NO}$ cutoffs (e.g., 45 ppb, cited in Barnes et al., 2010; see also, Taylor et al., 2006; Travers et al., 2007; and Pavord and Martin, 2009); or serially, for example, blood EOS cutoff followed by similarly subjectively chosen $FE_{NO}$ cutoffs (e.g., 47 ppb, Smith et al., 2005).

Classification of Pulmonary Diseases or Disorders Using White Blood Cell Ratio-Based Methods The present disclosure encompasses classification methods (e.g., the ELEN Index method, the ELEN Index plus $FE_{NO}$ cutoff method, and the EL-$FE_{NO}$ Index method) to classify a patient as having a certain pulmonary disease or disorder, e.g., eosinophilic asthma, which are based on the application of one or more predictors comprising a white blood cell ratio.

In some aspects, the classification methods disclosed herein can be used, for example, to treat a patient, to diagnose a patient, to monitor therapeutic efficacy in a patient, to monitor disease progression in a patient, to determine whether to administer a certain therapy to a patient. In some aspects, the classification methods disclosed herein can be applied to a subject having a pulmonary disease or disorder, for example, an eosinophilic disease or disorder such as eosinophilic asthma. In certain aspects, the disclosure is directed to classification methods using statistical models in which two peripheral blood cell ratios are used to predict two sputum eosinophil classes: less than 2% eosinophil cells in induced sputum (non-eosinophilic) vs. 2% or more eosinophil cells (eosinophilic).

In some aspects, the application of the classification methods of the present disclosure comprises calculating a set of intermediate scores (e.g., Score 1 and Score 2) from a pair of equations, each of which can comprise at least one predictor comprising a white blood cell ratio. In turn, the intermediate scores are used to determine or calculate a diagnostic score. For example:

$$\text{Intermediate Score 1} = \text{Predictor } A \ldots \text{Predictor } Z \quad \text{(Equation 1)}$$

$$\text{Intermediate Score 2} = \text{Predictor } 1 \ldots \text{Predictor } N \quad \text{(Equation 2)}$$

wherein the diagnostic score is, e.g., (Intermediate Score 2−Intermediate Score 1) or a decision rule such as "If Intermediate Score 2<Intermediate Score 1 then . . . [e.g., apply a certain treatment]."

In some aspects, predictors used by the classification methods described herein can comprise parameters as numeric representations of a blood analyte, physiological marker, lung function, patient reported outcome, medical history or a function (e.g., logarithm) thereof, wherein at least one parameter is a white blood cell ratio. A predictor used in a classification method of the disclosure can comprise a sum, difference, ratio or product of any two parameters, wherein at least one parameter is a white blood cell ratio. A predictor used in a classification method of the disclosure can also comprise a function (e.g., logarithm, square root) of a single parameter or the sum, difference, ratio or product of any two parameters.

In some aspects, the calculation of the intermediate scores comprises the same number of predictors in each equation (e.g., in the ELEN Index, ELEN plus $FE_{NO}$ cutoff, and EL-$FE_{NO}$ methods). In other aspects, the calculation of the intermediate scores comprises a different number of predictors in each equation.

In some aspects, the classification method comprises more than one predictor. In another aspect, the classification method comprises at least 2, at least 3, at least 4, at least 5, at least 6, at least 7, at least 8, at least 9 or at least 10 predictors. In a further aspect, the classification method of the disclosure uses 1, 2, 3, 4, 5, 6, 7, 8, 9 or 10 predictors. In a specific aspect, a classification method of the disclosure uses 2 predictors. In a further specific aspect, a classification method of the disclosure uses 3 predictors.

In one aspect, each predictor in the classification method comprises a white blood cell ratio. In another aspect, each predictor comprises the same white blood cell ratio. In another aspect, each predictor comprises a different white blood cell ratio.

In one aspect, the classification method does not use a predictor comprising induced sputum eosinophil count. In another aspect, the classification method comprises one predictor comprising a blood eosinophil/blood lymphocyte ratio. In another aspect, the classification method comprises one predictor comprising a blood eosinophil/blood neutrophil ratio. In another aspect, the classification method comprises one predictor comprising a blood eosinophil/white blood cell ratio. In one aspect, the classification method comprises a blood eosinophil/blood neutrophil ratio and one blood eosinophil/blood lymphocyte ratio. In another aspect, at least one predictor in the classification method comprises a $FE_{NO}$ measurement, a BMI measurement, or an analyte measurement. In one aspect, the classification method comprises at least one predictor comprising a $FE_{NO}$ measurement.

In one aspect, the classification method uses at least a first and second predictor wherein the first predictor comprises the blood eosinophil/blood lymphocyte ratio and the second predictor comprises the natural logarithm of the blood eosinophil/blood neutrophil ratio. In one aspect, the classification method uses a first and second predictor wherein the first predictor comprises the blood eosinophil/blood lymphocyte ratio and the second predictor comprises the natural logarithm of the blood eosinophil/blood neutrophil ratio. In one aspect, the classification method uses at least a first, second and third predictor wherein the first predictor comprises the blood eosinophil/blood lymphocyte ratio, the second predictor comprises the natural logarithm of the blood eosinophil/blood neutrophil ratio and the third predictor comprises the blood eosinophil/blood leukocyte ratio.

In one aspect, the classification method uses a first, second and third predictor wherein the first predictor comprises the blood eosinophil/blood lymphocyte ratio, the second predictor comprises the natural logarithm of the blood eosinophil/blood neutrophil ratio and the third predictor comprises the blood eosinophil/blood leukocyte ratio. In one aspect, the classification method uses at least a first and second predictor wherein the first predictor comprises a $FE_{NO}$ measurement and the second predictor comprises the natural logarithm of the blood eosinophil/blood lymphocyte ratio. In one aspect, the classification method uses a first and second predictor wherein the first predictor comprises a $FE_{NO}$ measurement and the second predictor comprises the natural logarithm of the blood eosinophil/blood lymphocyte ratio.

In one aspect, the classification method has a specificity of at least 65%, at least 70%, at least 75%, at least 80%, at least 85%, at least 90%, at least 95%, at least 96%, at least 97%, at least 98% or at least 99%. In a specific aspect, the classification method has an at least 80% specificity. In another aspect, the classification method has a sensitivity of at least 65%, at least 70%, at least 75%, at least 80%, at least 85%, at least 90%, at least 95%, at least 96%, at least 97%, at least 98% or at least 99%. In a specific aspect, the classification method has an at least 60% sensitivity. In a specific aspect, the classification method has an at least 70% sensitivity. In a further aspect, the classification method has an overall accuracy of at least 65%, at least 70%, at least 75%, at least 80%, at least 85%, at least 90%, at least 95%, at least 96%, at least 97%, at least 98% or at least 99%.

In a specific aspect, the classification method has an at least 80% overall accuracy. In a specific aspect, the classification method has an at least 70% overall accuracy. In another aspect, the classification method has a negative predictive value (NPV) of at least 65%, at least 70%, at least 75%, at least 80%, at least 85%, at least 90%, at least 95%, at least 96%, at least 97%, at least 98% or at least 99%. In a specific aspect, the classification method has an at least 80% NPV. In a specific aspect, the classification method has an at least 50% NPV. In a further aspect, the classification method has a positive predictive value of at least 65%, at least 70%, at least 75%, at least 80%, at least 85%, at least 90%, at least 95%, at least 96%, at least 97%, at least 98% or at least 99%. In a specific aspect, the classification method has an at least 80% PPV. In a specific aspect, the classification method has an at least 90% PPV.

ELEN Index Method

In some aspects, patient classification is performed using a classification method comprising a set of equations comprising two predictors, wherein the predictors are based respectively on Eosinophil/Lymphocyte and Eosinophil/Neutrophil ratios. The terms used to describe this family of classification methods through the instant disclosure are "ELEN Index" or "ELEN Index method." In the ELEN Index method, the intermediate scores (namely, Score 1 and Score 2) used to calculate a diagnostic score are obtained by applying the following set of equations:

Score 1=$a$+[$b$×blood eosinophil/blood lymphocyte]−[$c$×natural log(blood eosinophil/blood neutrophil)]

Score 2=$d$+[$e$×blood eosinophil/blood lymphocyte]−[$f$×natural log(blood eosinophil/blood neutrophil)]

wherein a is between about −74 and about −6; b is between about 45 and about 412; c is between about −38 and about −2; d is between about −95 and about −10; e is between about 65 and about 473; and, f is between about −39 and about −2. A diagnostic score wherein Score 1≤Score 2 indicates that the patient has an eosinophilic disease or disorder. In some aspects, a is about −10, b is about 70, c is about 4, d is about −15, e is about 101, and f is about 4. In some specific aspects, a is −9.5243233, b is 70.0974823, c is 3.7789926, d is −14.5853365, e is 101.2197561, and f is 3.9567050.

Thus, in a specific aspect, a patient is classified as having an eosinophilic disease or disorder if the patient comprises a diagnostic score wherein Score 1≤Score 2, wherein:

Score 1=−9.5243233+[70.0974823×blood eosinophil/blood lymphocyte]−[3.7789926×natural log (blood eosinophil/blood neutrophil)]; and Score 2=−14.5853365+[101.2197561×blood eosinophil/blood lymphocyte]−[3.9567050×natural log(blood eosinophil/blood neutrophil)].

In a further specific aspect which extends the ELEN Index method to include a third white blood cell ratio-based predictor, a patient is classified as having an eosinophilic disease or disorder if the patient comprises a diagnostic score wherein Score 1≤Score 2, wherein:

Score 1=$a$−($b$×log [blood eosinophil/blood neutrophil])−($c$×blood eosinophil/blood lymphocyte)+($d$×blood eosinophil/total white blood cell count); and Score 2=$e$−($f$×log [blood eosinophil/blood neutrophil])−($g$×blood eosinophil/blood lymphocyte)+($h$×blood eosinophil/total white blood cell count), and wherein a is about −200, b is about 100, c is about 300, d is about 3000, e is about −200, f is about 100, g is about 300, and h is about 3000. In some specific aspects, a is −189, b is 104.34, c is 310.23, d is 3016.6, e is −173.59, f is 99.63, g is 286.31, and h is 2895.13.

Thus, in a specific aspect, a patient is classified as having an eosinophilic disease or disorder if the patient comprises a diagnostic score wherein Score 1≤Score 2, wherein:

Score 1=−189−(104.34×log [blood eosinophil/blood neutrophil])−(310.23×blood eosinophil/blood lymphocyte)+(3016.8×blood eosinophil/total white blood cell count); and Score 2=−173.59−(99.63×log [blood eosinophil/blood neutrophil])−(286.31×blood eosinophil/blood lymphocyte)+(2895.13×blood eosinophil/total white blood cell count).

ELEN Index plus $FE_{NO}$ Cutoff Method

In some aspects, a white blood cell ratio-based classification method of the present disclosure can be combined in a two-step method with a subject's $FE_{NO}$ measurement to classify patients having a pulmonary disease or disorder, wherein the $FE_{NO}$ measurement is used as a cut-off. For example, to improve the sensitivity of the ELEN Index method, a subject's $FE_{NO}$ can also be measured wherein a $FE_{NO}$ greater than or equal to 50 ppb indicates the subject is an eosinophilic asthmatic. In order to be classified as an eosinophilic asthmatic, either the ELEN Index or $FE_{NO}$ test can be positive (i.e., Score 1≤Score 2 or $FE_{NO}$ of at least 50 ppb).

In some aspects, the classification of the subject as having a pulmonary disease or disorder is determined by the ELEN Index in combination with $FE_{NO}$ wherein either a positive ELEN Index result or a $FE_{NO}$ of at least 50 ppb indicate that the subject has a pulmonary disease or disorder. In one aspect, the specificity, sensitivity, accuracy NPV, and/or PPV of the method is increased by using the ELEN Index in combination with $FE_{NO}$ (i.e., either a positive ELEN Index result or a positive $FE_{NO}$ of at least 50 ppb) compared to the ELEN Index alone.

In a further aspect, the classification method can detect when the ELEN Index is positive (i.e., Score 1≤Score 2) and $FE_{NO}$ is greater than or equal to 50 ppb. This double positive classification method is able to identify a higher proportion of subjects with >8% sputum eosinophils which correlates with an even higher risk for future asthma attacks than a single positive classification (double positive=50%, ELEN+ve=42% and ≥FENO 50 ppb=42%).

In some specific aspects, a subject's $FE_{NO}$ measurement is tested and combined as a cut-off with a subject's ELEN Index for selection of patients for treatment with an anti-IL5 or anti-IL-5R antibody.

In certain aspects, $FE_{NO}$ can be combined with the ELEN Index when $FE_{NO}$ is greater than or equal to 35 parts per billion (ppb). In one aspect, $FE_{NO}$ can be combined with the ELEN Index when $FE_{NO}$ is greater than or equal to 40 ppb. In one embodiment, $FE_{NO}$ can be combined with the ELEN Index when $FE_{NO}$ is greater than or equal to 45 ppb. In another aspect, $FE_{NO}$ can be combined with the ELEN Index when $FE_{NO}$ is greater than or equal to 50 ppb. In another aspect, $FE_{NO}$ can be combined with the ELEN Index when $FE_{NO}$ is at least 35 ppb, 36 ppb, 37 ppb, 38 ppb, 39 ppb, 40 ppb, 41 ppb, 42 ppb, 43 ppb, 44 ppb, 45 ppb, 46 ppb, 47 ppb, 48 ppb, 49 ppb, 50 ppb, 51 ppb, 52 ppb, 53 ppb, 54 ppb, 55 ppb, 56 ppb, 57 ppb, 58 ppb, 59 ppb or 60 ppb. In certain aspects, $FE_{NO}$ is at least 50 ppb.

EL-$FE_{NO}$ Index Method

In some aspects, patient classification is performed using a classification method comprising a set of equations comprising two predictors, wherein the predictors are based respectively on the Eosinophil/Lymphocyte ratio and $FE_{NO}$ measurements. The terms used to describe this family of classification methods through the instant disclosure are "EL-$FE_{NO}$ Index" or "EL-$FE_{NO}$ Index method." In the EL-$FE_{NO}$ Index method, the intermediate scores (namely, Score 1 and Score 2) used to calculate a diagnostic score are obtained by applying the following equations:

$$\text{Score 1} = a' + (b' \times FE_{NO} \text{ ppb}) - [c' \times \text{natural log(blood eosinophil/blood lymphocyte)}]$$

$$\text{Score 2} = d' + (e' \times FE_{NO} \text{ ppb}) - [f' \times \text{natural logarithm (blood eosinophil/blood lymphocyte)}]$$

wherein a' is between about −14 and about −4; b' is between about 0.01 and about 0.16; c' is between about −10 and about −2.2; d' is between about −10 and about −3.2; e' is between about 0.035 and about 0.17; and, f' is between about −8 and about −1.5. A diagnostic score wherein Score 1≤Score 2 indicates that the patient has an eosinophilic disease or disorder. In some aspects, a' is about −5, b' is about 0.03, c' is about 2.5, d' is about −3.5, e' is about 0.05, and f is about 2. In some specific aspects, a' is −4.6368456, b' is 0.0300382, c' is 2.5409793, d' is −3.6017103, e' is 0.0559650, and f' is 1.7349461.

Thus, in a specific aspect, a patient is classified as having an eosinophilic disease or disorder if the patient comprises a diagnostic score wherein Score 1≤Score 2, wherein:

$$\text{Score 1} = -4.6368456 + (0.0300382 \times FE_{NO} \text{ ppb}) - [2.5409793 \times \text{natural log(blood eosinophil/blood lymphocyte)}], \text{ and}$$

$$\text{Score 2} = 3.6017103 + (0.0559650 \times FE_{NO} \text{ ppb}) - [1.7349461 \times \text{natural logarithm(blood eosinophil/blood lymphocyte)}].$$

Methods of Treatment, Diagnosis and Monitoring

The present disclosure provides methods for treatment, diagnosis, and monitoring of pulmonary diseases and disorders which apply the classification methods disclosed herein.

In some aspects, the present disclosure provides a method of treating a patient having a pulmonary disease comprising (a) measuring a white blood cell count in a sample taken from a patient having a pulmonary disease or disorder (e.g., eosinophilic asthma) to calculate a white blood cell ratio; (b) calculating a diagnostic score from the white blood cell ratio (e.g., using the ELEN Index, ELEN Index plus $FE_{NO}$ cut-off, or EL-$FE_{NO}$ Index classification methods disclosed herein), wherein the diagnostic score indicates whether the patient will benefit from administration of a therapy; and, (c) administering the therapy to the patient if the diagnostic score indicates that the patient will benefit from administration of the therapy. The present disclose also provides method of treating a patient having a pulmonary disease or disorder (e.g., eosinophilic asthma) comprising (a) calculating a diagnostic score from a white blood cell ratio measured from a white blood cell count obtained from a sample taken from a patient having a pulmonary disease or disorder (e.g., using the ELEN Index, ELEN Index plus $FE_{NO}$ cut-off, or EL-$FE_{NO}$ Index classification methods disclosed herein); (b) determining from the diagnostic score whether the patient will benefit from administration of a therapy; and, (c) administering the therapy to the patient if the diagnostic score indicates that the patient will benefit from administration of the therapy.

Also provided is a method of treating a patient having a pulmonary disease or disorder (e.g., eosinophilic asthma) comprising (a) measuring a white blood cell count in a sample taken from a patient having a pulmonary disease or disorder to calculate a white blood cell ratio; (b) calculating a diagnostic score from the white blood cell ratio (e.g., using the ELEN Index, ELEN Index plus $FE_{NO}$ cut-off, or EL-$FE_{NO}$ Index classification methods disclosed herein), wherein the diagnostic score indicates whether the patient will benefit from administration of a therapy; and, (c) instructing a healthcare provide to administer the therapy to the patient if the diagnostic score indicates that the patient will benefit from administration of the therapy.

The present disclosure also provides a method of treating a patient having a pulmonary disease or disorder (e.g., eosinophilic asthma) comprising (a) calculating a diagnostic score from a white blood cell ratio measured from a white blood cell count obtained from a sample taken from a patient having a pulmonary disease or disorder (e.g., using the ELEN Index, ELEN Index plus $FE_{NO}$ cut-off, or EL-$FE_{NO}$ Index classification methods disclosed herein); (b) determining from the diagnostic score whether the patient will benefit from administration of a therapy; and, (c) instructing a healthcare provider to administer the therapy to the patient if the diagnostic score indicates that the patient will benefit from administration of the therapy.

Also provides is a method of treating a patient having a pulmonary disease or disorder (e.g., eosinophilic asthma) comprising (a) determining from a diagnostic score calculated from a white blood cell ratio measured from a white blood cell count obtained from a sample taken from a patient having a pulmonary disease or disorder whether the patient will benefit from administration of a therapy (e.g., using the ELEN Index, ELEN Index plus $FE_{NO}$ cut-off, or EL-$FE_{NO}$ Index classification methods disclosed herein); and, (b) administering the therapy to the patient if the diagnostic score indicates that the patient will benefit from administration of the therapy.

Also provides is method of treating a patient having a pulmonary disease or disorder (e.g., eosinophilic asthma) comprising (a) submitting a sample taken from a patient having a pulmonary disease or disorder for measurement of a white blood cell count, calculation of a white blood cell ratio from said cell count, determination of a diagnostic score, or combination thereof, wherein the diagnostic score is calculated from the white blood cell count or the white blood cell ratio (e.g., using the ELEN Index, ELEN Index plus $FE_{NO}$ cut-off, or EL-$FE_{NO}$ Index classification methods disclosed herein); and, (b) administering the therapy to the patient if the diagnostic score indicates that the patient will benefit from administration of the therapy.

The present disclosure also provides a method of treating a patient having a pulmonary disease or disorder (e.g., eosinophilic asthma) comprising (a) submitting a sample taken from a patient having a pulmonary disease or disorder for measurement of a white blood cell count, calculation of a white blood cell ratio from said white blood cell count, determination of a diagnostic score, or combination thereof, wherein the diagnostic score is calculated from the white blood cell count or the white blood cell ratio (e.g., using the ELEN Index, ELEN Index plus $FE_{NO}$ cut-off, or EL-$FE_{NO}$ Index classification methods disclosed herein); and, (b) instructing a healthcare provide to administer the therapy to the patient if the diagnostic score indicates that the patient will benefit from administration of the therapy.

The instant disclosure also provides diagnostic methods. In this respect, the disclosure provides a method of diagnosing whether a patient is in need of therapy to treat a pulmonary disease or disorder (e.g., eosinophilic asthma), comprising (a) measuring a white blood cell count in a sample taken from the patient to calculate a white blood cell ratio; (b) calculating a diagnostic score from the white blood cell ratio (e.g., using the ELEN Index, ELEN Index plus $FE_{NO}$ cut-off, or EL-$FE_{NO}$ Index classification methods disclosed herein), wherein the diagnostic score indicates whether the patient has a pulmonary disease or disorder; and (c) instructing a healthcare provider to provide therapy to treat a pulmonary disease or disorder if the patient is in need thereof. Also provided is a method of diagnosing whether a patient is in need of therapy to treat a pulmonary disease or disorder (e.g., eosinophilic asthma), comprising (a) calculating a diagnostic score from a white blood cell ratio measured from a white blood cell count obtained from a sample taken from the patient (e.g., using the ELEN Index, ELEN Index plus $FE_{NO}$ cut-off, or EL-$FE_{NO}$ Index classification methods disclosed herein); (b) determining from the diagnostic score whether the patient has a pulmonary disease or disorder; and, (c) providing therapy to treat a pulmonary disease or disorder if the patient is in need thereof.

Also provided is a method of diagnosing whether a patient is in need of therapy to treat a pulmonary disease or disorder (e.g., eosinophilic asthma) comprising (a) determining whether the patient has a pulmonary disease or disorder from a diagnostic score calculated from a white blood cell ratio measured from a white blood cell count obtained from a sample taken from the patient (e.g., using the ELEN Index, ELEN Index plus $FE_{NO}$ cut-off, or EL-$FE_{NO}$ Index classification methods disclosed herein); and, (b) providing therapy or instructing a healthcare provider to provide therapy to treat a pulmonary disease or disorder if the patient is in need thereof. Furthermore, the present disclosure provides a method of diagnosing whether a patient is in need of therapy to treat a pulmonary disease or disorder (e.g., eosinophilic asthma) comprising (a) submitting a sample taken from the patient for measurement of a white blood cell count, calculation of a white blood cell ratio from said cell count, determination of a diagnostic score, or combination thereof, wherein the diagnostic score is calculated from the white blood cell count or the white blood cell ratio; and wherein the diagnostic score indicates whether the patient has a pulmonary disease or disorder; and, (b) providing therapy or instructing a healthcare provider to provide therapy to treatment a pulmonary disease or disorder if the patient is in need thereof.

The present disclosure also provides methods of monitoring the efficacy of a therapy, or the progression of a pulmonary disease or disorder. These methods comprise the comparison of at least two diagnostic scores which can be obtained, for example, using the ELEN Index, ELEN Index plus $FE_{NO}$ cut-off, or EL-$FE_{NO}$ Index classification methods disclosed herein. In this respect, the present disclosure provides is a method of monitoring the efficacy of a therapy administered to a patient having a pulmonary disease or disorder (e.g., eosinophilic asthma) comprising (a) calculating a first diagnostic score from a first white blood cell ratio measured from a white blood cell count obtained from a first sample taken from a patient having a pulmonary disease or disorder; (b) administering a therapy to the patient to treat the pulmonary disease or disorder; (c) calculating a second diagnostic score from a second white blood cell ratio measured white blood cell count obtained from a second sample taken from the patient; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

Also provided is a method of monitoring the efficacy of a therapy administered to a patient having a pulmonary disease or disorder (e.g., eosinophilic asthma) comprising (a) submitting a first sample taken from a patient having a pulmonary disease or disorder for measurement of a white blood cell count, calculation of a white blood cell ratio from said white blood cell count, determination of a first diagnostic score, or combination thereof, wherein the first diagnostic score is calculated from the white blood cell count or the white blood cell ratio; (b) administering a therapy to the patient to treat the pulmonary disease or disorder; (c) submitting a second sample taken from a patient having a pulmonary disease or disorder for measurement of a white blood cell count, calculation of a white blood cell ratio from said white blood cell count, determination of a second diagnostic score, or combination thereof, wherein the second diagnostic score is calculated from the white blood cell count or the white blood cell ratio; (d) comparing the first diagnostic score and the second diagnostic score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

In addition, the present disclosure provides a method of monitoring the efficacy of a therapy administered to a patient having a pulmonary disease or disorder (e.g., eosinophilic asthma) comprising (a) calculating a first diagnostic score from a first white blood cell ratio measured from a white blood cell count obtained from a first sample taken from a patient having a pulmonary disease or disorder; (b) administering a therapy to the patient to treat the pulmonary disease or disorder; (c) submitting a second sample taken from a patient having a pulmonary disease or disorder for measurement of a white blood cell count, calculation of a white blood cell ratio from said white blood cell count, determination of a second diagnostic score, or combination thereof, wherein the second diagnostic score is calculated from the white blood cell count or the white blood cell ratio; (d) comparing the first diagnostic score and the second diagnostic score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

Also provided is a method of monitoring the efficacy of a therapy administered to a patient having a pulmonary disease or disorder (e.g., eosinophilic asthma) comprising (a) submitting a first sample taken from a patient having a pulmonary disease or disorder for measurement of a white blood cell count, calculation of a white blood cell ratio from said white blood cell count, determination of a first diagnostic score, or combination thereof, wherein the first diagnostic score is calculated from the white blood cell count or the white blood cell ratio; (b) administering a therapy to the patient to treat the pulmonary disease or disorder; (c) calculating a second diagnostic score from a second white blood cell ratio measured from a white blood cell count obtained from a second sample taken from a patient having a pulmonary disease or disorder; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score. The present disclosure also provides a method of monitoring the efficacy of a therapy administered to a patient having a pulmonary disease or disorder (e.g., eosinophilic asthma) comprising (a) calculating a first diagnostic score from a first white blood cell ratio measured from a white blood cell count obtained from a first sample taken from a patient having a pulmonary disease or disorder; (b) instructing a healthcare provider to administer a therapy to the patient to treat the pulmonary disease or disorder; (c) calculating a second diagnostic score from a second white blood cell ratio measured from a white blood cell count obtained from a second sample taken from the patient; (d) comparing the first diagnostic score and the diagnostic second score, wherein a first diagnostic score greater than the second diagnostic score indicates efficacy; and, (e) altering or instructing a healthcare provider or healthcare benefits provider to alter the therapy if the second diagnostic score is equal or higher than the first diagnostic score.

In some aspects, the methods of treatment, diagnosing, and monitoring described above comprise calculating a set of intermediate scores (e.g., Score 1 and Score 2) from a pair of equations (corresponding, e.g., to the ELEN Index, ELEN Index plus $FE_{NO}$ cut-off, or $EL-FE_{NO}$ Index classification methods), each of which can comprise at least one predictor comprising a white blood cell ratio. In turn, the intermediate scores are used to determine or calculate a diagnostic score. For example:

Intermediate Score 1=Predictor $A$ ... Predictor $Z$ (Equation 1)

Intermediate Score 2=Predictor 1 ... Predictor $N$ (Equation 2)

wherein the diagnostic score is, e.g., (Intermediate Score 2−Intermediate Score 1) or a decision rule such as "If Intermediate Score 2<Intermediate Score 1 then ... [e.g., apply a certain treatment]."

In some aspects, the pulmonary disease in the disclosed methods of treating, diagnosing, and monitoring is a chronic pulmonary disease. In some aspects, the pulmonary disease is selected from the group consisting of asthma and chronic pulmonary disease (COPD). In other aspects, the pulmonary disease is a pulmonary eosinophilic disease, e.g., eosinophilic asthma.

In some aspects, the therapy in the disclosed methods of treating, diagnosing, and monitoring comprises the administration of a therapeutic agent. The therapeutic agent can be a biologic agent. In some aspects, the therapeutic agent can be a small molecule drug. In other aspects, the biologic agent can be an antibody or an antigen-binding fragment thereof, e.g., an anti-IgE antibody. In other aspects, the antibody or antigen-binding fragment thereof can be an anti-cytokine antibody or an anti-cytokine receptor antibody. In some aspects, the anti-cytokine antibody can be an anti-interleukin antibody, e.g., an anti-IL5 antibody. In other aspects, the anti-cytokine receptor antibody can be an anti-interleukin receptor antibody, e.g., an anti-IL-5R antibody. In specific aspects, the anti-IL5 antibody is selected from the group consisting of reslizumab, mepolizumab, omalizumab, and any combination thereof. In specific aspects, the anti-IL-5R antibody is benralizumab. In other specific aspects, the anti-IL5R antibody is not benralizumab. In some aspects, the anti-IL5R antibody binds the same epitope as benralizumab.

In some aspects, the small molecule drug in the disclosed methods of treating, diagnosing, and monitoring is a corticosteroid. In other aspects, the small molecule drug is not a corticosteroid. In some aspects, the patient has an eosinophil sputum count of at least about 2%. In other aspects, the patient has an eosinophil sputum count of at least about 8%. In other aspects, the patient has a $FE_{NO}$ of at least about 50 ppb. In some aspects, the sample is a blood, serum, or plasma sample. In other aspects, the white blood cell count is a complete blood count (CBC) with differentials. In some aspects, the white blood cell count comprises an eosinophil count, a neutrophil count, a lymphocyte count, an eosinophil precursor count, a basophil precursor count, or any combination thereof. In other aspects, the white blood cell ratio is a ratio between an eosinophil count and a second white blood cell type count.

In some aspects, the white blood cell ratio in the disclosed methods of treating, diagnosing, and monitoring is an eosinophil count to lymphocyte count ratio (blood eosinophil/blood lymphocyte ratio). In other aspects, the white blood cell ratio is an eosinophil count to a neutrophil count ratio (blood eosinophil/blood neutrophil ratio). In some aspects, the diagnostic score is the variance between two intermediate scores (Score 1 and Score 2), wherein the calculation of Score 1 and Score 2 comprises at least one predictor comprising a white blood cell ratio. In other aspects, the calculation of Score 1 and Score 2 comprises a predictor not comprising a white blood cell ratio or a function thereof. In some aspects, at least one predictor comprises a function of a white blood cell ratio. In some aspects, the function is a natural logarithm. In other aspects, at least one predictor comprises a sum, difference, ratio or product of a coefficient to a while blood cell ratio or a function thereof. In some aspects, the calculation of Score 1 and the calculation of Score 2 comprises the same number of predictors, for example one predictor, two predictors or at least three predictors.

In other aspects, each predictor in the disclosed methods of treating, diagnosing, and monitoring comprises a white blood cell ratio. In some aspects, each predictor comprises the same white blood cell ratio. In other aspects, each predictor comprises a different white blood cell ratio. In some aspects, one predictor comprises a blood eosinophil/blood lymphocyte ratio. In other aspects, one predictor comprises a blood eosinophil/blood neutrophil ratio. In some aspects, one predictor comprises a blood eosinophil/white blood cell ratio. In other aspects, one predictor comprises a blood eosinophil/blood neutrophil ratio and one blood eosinophil/blood lymphocyte ratio.

In some aspects, Score 1 in the disclosed methods of treating, diagnosing, and monitoring is calculated according to the formula Score 1=a+[b×blood eosinophil/blood lymphocyte]−[c×natural log(blood eosinophil/blood neutrophil)]

and Score 2 is calculated according to the formula:

Score 2=d+[e×blood eosinophil/blood lymphocyte]−[f×natural log(blood eosinophil/blood neutrophil)], wherein:
(a) a is between about −74 and about −6;
(b) b is between about 45 and about 412;
(c) c is between about −38 and about −2;
(d) d is between about −95 and about −10;
(e) e is between about 65 and about 473; and,
(f) f is between about −39 and about −2,
wherein a Score 1≤Score 2 indicates that the patient has an eosinophilic disease or disorder. In some aspects, the coefficients in the disclosed method are: a is about −10, b is about 70, c is about 4, d is about −15, e is about 101, and f is about 4. In some aspects, the coefficients in the disclosed method are: a is −9.5243233, b is 70.0974823, c is 3.7789926, d is −14.5853365, e is 101.2197561, and f is 3.9567050, In other aspects, at least one predictor in the disclosed methods of treating, diagnosing, and monitoring comprises a $FE_{NO}$ measurement, a BMI measurement, or an analyte measurement. In some aspects, the analyte is periostin. In some aspects, the at least one predictor comprises a $FE_{NO}$ measurement. In some aspects, the calculation of Score 1 and the calculation of Score 2 comprises the same number of predictors. In other aspects, the calculation of Score 1 and the calculation of Score 2 comprises two predictors. In some aspects, one of the two predictors comprises a white blood cell ratio and the other predictor comprises a $FE_{NO}$ measurement. In some aspects, the collection of the sample to measure the white blood cell ratio and the $FE_{NO}$ measurement are performed on the same day. In other aspects, the white blood count and $FE_{NO}$ measurement are performed on the same day. In some aspects, the white blood cell ratio is a blood eosinophil/blood lymphocyte ratio.

In some aspects, Score 1 in the disclosed methods of treating, diagnosing, and monitoring is calculated according to the formula Score 1=a'+(b'×$FE_{NO}$ ppb)−[c'×natural log(blood eosinophil/blood lymphocyte)]

and Score 2 is calculated according to the formula:

Score 2=d'+(e'×$FE_{NO}$ ppb)−[f'×natural logarithm (blood eosinophil/blood lymphocyte)]

wherein:
(a) a' is between about −14 and about −4;
(b) b' is between about 0.01 and about 0.16;
(c) c' is between about −10 and about −2.2;
(d) d' is between about −10 and about −3.2;
(e) e' is between about 0.035 and about 0.17; and,
(f) f' is between about −8 and about −1.5,
wherein a Score 1≤Score 2 indicates that the patient has an eosinophilic disease or disorder. In some aspects, the coefficients in the disclosed method are: a' is about −5, b' is about 0.03, c' is about 2.5, d' is about −3.5, e' is about 0.05, and f' is about 2. In some aspects, the coefficients in the disclosed method are: a' is −4.6368456, b' is 0.0300382, c' is 2.5409793, d' is −3.6017103, e' is 0.0559650, and f' is 1.7349461, Pulmonary Diseases and Disorders The methods and systems in the present disclosure can be applied to any pulmonary diseases or disorders. In one aspect, the subject has, e.g., asthma, COPD, eosinophilic asthma, combined eosinophilic and neutrophilic asthma, aspirin sensitive asthma, allergic bronchopulmonary aspergillosis, acute and chronic eosinophilic bronchitis, acute and chronic eosinophilic pneumonia, Churg-Strauss syndrome, hypereosinophilic syndrome, drug, irritant and radiation-induced pulmonary eosinophilia, infection-induced pulmonary eosinophilia (fungi, tuberculosis, parasites), autoimmune-related pulmonary eosinophilia, eosinophilic esophagitis, and Crohn's disease. In one aspect, the subject has a pulmonary eosinophilic disease or disorder. In another aspect, the pulmonary disease or disorder is asthma. In another aspect, the pulmonary disease or disorder is eosinophilic asthma.

Asthma is considered a common inflammatory disease of the airways characterized, e.g., by variable and recurring symptoms, reversible airflow obstruction, and bronchospasm. Asthma symptoms can include wheezing, coughing, chest tightness, and shortness of breath. Symptoms can be triggered by exposure to allergens or irritants. Asthma can be classified as atopic (extrinsic) or non-atopic (intrinsic), based on whether symptoms are precipitated by allergens (atopic) or not (non-atopic). An acute asthma exacerbation is commonly referred to as an asthma attack. Further signs which can occur during an asthma attack include the use of accessory muscles of respiration (sternocleidomastoid and scalene muscles of the neck), there may be a paradoxical pulse (a pulse that is weaker during inhalation and stronger during exhalation), and over-inflation of the chest. A blue color of the skin and nails may occur from lack of oxygen.

Agents currently used to treat asthma are divided into two general classes: quick-relief medications used to treat acute symptoms; and long-term control medications used to prevent further exacerbation. Fast acting treatments include, e.g., short-acting beta-2 adrenoceptor agonist (SABA) (e.g., salbutamol); anticholinerginic medications (e.g., ipratropium bromide), and adrenergic agonists (e.g., epinephrine). Long term control treatments include, e.g., glucocorticoids (e.g., budesonide or fluticasone propionate); long-acting beta-2 adrenoceptor agonist (LABA); leukotriene antagonists (e.g., zafirlukast); and mast cell stabilizers (e.g., cromolyn sodium). Fast acting and long term control treatments are often administered by inhalation. In certain aspects, the methods and systems of the invention are used to identify subjects who might benefit from administration of an agent for treatment of asthma.

In another aspect, the pulmonary disease or disorder is chronic obstructive pulmonary disease (COPD). COPD is one of the most common lung diseases most frequently associated with smoking. COPD makes it difficult to breathe. There are two main forms of COPD: Chronic bronchitis, defined by a long-term cough with mucus; and emphysema, defined by destruction of the alveoli of the lungs over time. Most people with COPD have a combination of both conditions. Smoking is the leading cause of COPD. The more a person smokes, the more likely that person will develop COPD although some people smoke for years and never develop COPD. It has also been reported that nonsmokers who lack a protein called alpha-1 antitrypsin can develop emphysema. Other risk factors for COPD include, e.g., exposure to certain gases or fumes in the workplace, exposure to heavy amounts of secondhand smoke and pollution, frequent use of cooking gas without proper ventilation. Symptoms associated with COPD include, e.g., cough with mucus, shortness of breath (dyspnea) that often gets worse with mild activity, fatigue, frequent respiratory infections, and wheezing. Examples of current treatments for COPD symptoms include, e.g., inhalers (bronchodilators) to open the airways, such as, e.g., ipratropium (Atrovent), tiotropium (Spiriva), salmeterol (Serevent), or formoterol (Foradil); inhaled steroids to reduce lung inflammation; antibiotics because infections can make COPD worse; and oxygen therapy. In certain aspects, the methods and systems of the present disclosure are used to identify subjects who might benefit from administration of an agent for treatment of COPD.

White Blood Cell Count

As described herein, the methods and systems of the present disclosure can be used with any suitable source of blood, serum, or plasma sample.

The term "white blood cell count" as used herein refers to a count of white blood cells from any sample, for example, a complete blood count (CBC) with white blood cell (WBC) differentials (CBC with differential). Obtaining a CBC with differential can be achieved using any suitable techniques available in the art, e.g., by automated hematology analyzer or hematology coulter counters (e.g., flow cytometry) or by manually counting cells (e.g., using a microscope).

A CBC with differential is one of the most widely ordered clinical laboratory tests in the world. There are two major steps are involved in this process, specimen collection (i.e., sample collection) and specimen analysis. In some aspects, samples are collected from venous blood employing standard phlebotomy procedures. In some aspects, a tourniquet is placed on the arm of the subject. In some aspects, the area for venipuncture can be cleaned using aseptic technique.

In some aspects, blood for measurement of a CBC with differential can be collected into a tube. In some aspects, such tube contains and anticoagulant. In some aspects, the anticoagulant is ethylenediaminetetraacetic acid (EDTA). In other cases, the anticoagulant is not EDTA.

In some aspects, the specimen can be collected in a tube containing K3-EDTA, a liquid form of EDTA. In some aspects, the sample can be diluted with, for example, K3-EDTA by 1-2%. In other aspects, the specimen can be collected in a tube containing K2-EDTA. In some aspects, K2-EDTA can be sprayed onto the walls of the tube and does not dilute the blood sample. In some aspects, after collection of the blood sample the tube should be inverted one or more times (e.g., 8-10 times) to mix the contents thoroughly.

While EDTA tubes prevent blood from clotting, the cells in the blood sample are fragile and began to senesce as time progresses. At room temperature the average change in lymphocyte and neutrophil percentages within 24 hours of blood draw is −4% and +2% respectively, while absolute eosinophil counts decrease approximately 13% (Hill, 2009). Thus, in some aspects, samples (e.g., samples for measurement of a CBC with differential) are analyzed within 4 hours of collection. In some aspects, samples are analyzed less than about 1 hour, less than about 2 hours, less than about 3 hours, less than about 4 hours, less than about 5 hours, less than about 6 hours, less than about 7 hours, less than about 8 hours, less than about 9 hours, or less than about 10 hours from collection.

In some aspects, to maximize the accuracy of the methods of systems of the instant disclosure, in particular their application to pulmonary eosinophilic diseases or disorders, at least two CBC with differential samples can be collected 1-2 weeks apart. In same aspects, the cell count values can be averaged (e.g., average white blood cell count values for different white blood cell types such as eosinophils) and used as input for ratio and score calculations.

There can be variation in cell counts (and other analytes) throughout the day, particularly with eosinophils. Therefore, in some aspects, multiple CBC with differential samples (or other analyte samples) can be obtained at same time of day to minimize potential variation.

In some aspects, an alternative blood collection method to standard phlebotomy can be used to obtain samples for measurement of CBC with differential or other analytes in samples. In some aspects, the alternative blood collection method is the finger stick method. In general, when the finger stick method is applied, a finger is warmed to increase blood flow and cleaned aseptically, using a finger-designed lancet the skin is pricked, the first drop of blood is wiped away, and blood can be collected in Becton Dickinson Microtainer MAP Microtube or equivalent tubes. Generally, the sample is inverted 8 times to thoroughly mix the sample. In some aspects, about 250-500 µl samples are obtained using the finger stick method.

In some aspects, whole blood is collected for delayed analysis. In some aspects, blood samples can be collected in tubes containing cell stabilizers/preservatives (e.g., Streck and TransFix tubes). In some aspects, blood samples can be collected in tubes containing, EDTA, lithium heparin. In some cases, delayed analysis is performed up 1 one day, up to 2 days, up to 3 days, up to 4 days, or up to 5 days after collection. In specific aspects, delayed analysis is performed less than 3 days after collection. In some aspects, delayed analysis is performed via flow cytometry.

In some aspects, samples are collected according to at least one of the following conditions:

(1) Asthma inhaled and oral medications particularly corticosteroids are constant for a minimum of 4 weeks, but ideally for at least 6 weeks prior to testing;

(2) Subjects who have experienced an upper or lower respiratory infections or other infections requiring antibiotics or antivirals have blood drawn at least 4 weeks after completion of the drug therapy, but ideally at least 6 weeks after the completion of drug therapy;

(3) Subjects who experience a febrile illness wait at least 4 weeks after the fever is resolved, but ideally at least 6 weeks after the fever is resolved before having blood drawn;

(4) Subjects taking non-asthma concomitant medications that can alter blood cells counts are on a constant dose of these medications for at least 4 weeks, but ideally for at least 6 weeks prior to blood draw;

(5) Repeat samples are drawn at the same time of day to minimize potential variations;

(6) Collected samples remain at room temperature until analyzed, generally within 4 hours of blood draw up to a maximum of 10 hours;

(7) EDTA tubes are filled to the proper level; since underfilling or overfilling the tube can adversely affect the study result;

(8) Immediately after collection the EDTA tubes are inverted 8-10 times to thoroughly mix the sample and prevent clotting of the sample.

In some aspects, samples can analyzed using automated hematology analyzers, for example, Siemens Advia 120;

Abbott Cell Dyn 3500; Beckman Coulter LH750; Sysmex X series; Horiba ABX, etc. In some aspects, to maximize the accuracy of the disclosed methods, readouts from automated hematology analyzers report absolute eosinophil counts to at least 2 digits (e.g., 150, 220, 340 cells/µL), and at least 3 digits for lymphocytes and neutrophils (e.g., 1,530, 2,340, 3,410 cells/µL). In some aspects, prior to analyzing the blood sample, the tube should be inverted several times, e.g., 2, 3, 4, 5, 6, 7, 8, 9, 10 or more than 10 times, or according to manufacturer's instructions. In some aspects, samples can be analyzed manually.

In some aspects, samples are analyzed only if the subject is not acutely ill or has another significant underlying medical condition that could affect the results of the test. Thus, in some aspects, if the CBC report gives a white blood cell count that is abnormal (<5% or >95% percentile), this would alert the healthcare provider or healthcare benefits provider that the subject may have a subclinical infection or disease that may alter the differential and thus adversely affect the accuracy of the disclosed methods. Likewise, if there are other significant abnormalities in the CBC such as hemoglobin, hematocrit, mean cell volume, red blood cell count, etc., this would alert the healthcare provider or healthcare benefits provider that the subject has some conditions that can adversely affect the accuracy of the disclosed methods.

$FE_{NO}$ Measurements

In some aspects, indirect measurement of airway inflammation can be performed using a standardized single-breath $FE_{NO}$ test (ATS, 2005). As used herein, $FE_{NO}$ can be determined by any method known in the art. In one aspect, NIOX MINO® or similar device for measuring $FE_{NO}$ is used (see, e.g., Tsuburai et al., 2010). A non-limiting list of devices that can be used to measure $FE_{NO}$ includes: NIOX/N10×FLEX® and NIOX MINO® (Aerocrine, Sweden); CLD88 Series (Eco Medics, Germany); Sievers Nitric Oxide analyzer 280i (General Electric, USA); Logan LR 2000 and NObreath (Bedfont Scientific Ltd, UK). The $FE_{NO}$ signal can be capture, for example, using chemiluminescence, electrochemical sensing, or laser spectroscopy.

In some aspects, $FE_{NO}$ can be measured using "on-line" systems in which exhaled breath is directly blown into the machine detector and reported immediately, or "off-line" systems in which exhaled breath is captured in a bag, sealed and is analyzed remotely at a later time (e.g., using SIEVERS® or CEIS®). NIOX MINO® uses an "on-line" method in which the exhaled air from a subject is measured directly in a machine in real time. In addition to NIOX MINO®, other machines are commercially available for use with the "on-line" method.

$FE_{NO}$ measurement can vary between different machines by about 1-10 or about 5-10 points (e.g., by parts per billion (ppb)). In one aspect, the $FE_{NO}$ measurement varies by plus or minus 1, 2, 3, 4, 5, 6, 7, 8, 9, or 10 points (e.g., by ppb). The $FE_{NO}$ measurement can vary between repeat tests on the same machine by about 1-10 or about 5-10 points (e.g., by parts ppb). In one aspect, the $FE_{NO}$ measurement between repeat tests varies by plus or minus 1, 2, 3, 4, 5, 6, 7, 8, 9, or 10 points (e.g., by ppb).

Non-limiting examples of factors that can influence the $FE_{NO}$ measurements include exercise, spirometry, steroid treatment, respiratory infections, smoking and consuming foods rich in nitrates. In one aspect, prior to the $FE_{NO}$ measurement, the $FE_{NO}$ test is completed prior to a spirometry (e.g., Vital capacity (VC), Forced vital capacity (FVC), Forced expiratory volume (FEV), Forced expiratory flow (FEF) and Maximal voluntary ventilation (MVV)) test if a spirometry test is to performed on the same day. In another aspect, subjects have not been treated with a systemic corticosteroid burst within 30 days of taking the $FE_{NO}$ measurement. In another aspect, subjects have not been treated with a systemic corticosteroid burst within 6 weeks of taking the $FE_{NO}$ measurement. In another aspect, subjects have consumed foods rich in nitrates prior to taking the $FE_{NO}$ measurement.

In another aspect, subjects do not have or are not recovering from a respiratory infection at the time of taking the $FE_{NO}$ measurement. In some aspects, subjects have recovered from a respiratory infection prior to testing. In some aspects, subjects have recovered from an acute respiratory infection prior to testing. In other aspects, subjects have recovered from any acute respiratory infections for at least one week, at least two weeks, at least three weeks, or at least four weeks prior to testing. In some aspects, subjects have refrained from ingesting caffeine and/or alcohol for several hours, or several days, or several weeks before testing.

Exercise and performing spirometry can potentially impact the $FE_{NO}$ measurement. Thus, in some aspects, subjects have not exercised or performed spirometry for about one hour, or about 2 hours, or about 3 hours, or about 4 hours, or about 5 hours, or about 6 hours, or about 7 hours, or about 8 hours, or about 9 hours, or about 10 hours, or about 11 hours, or about 12 hours prior to $FE_{NO}$ testing. In some aspects, the subject should not eat or drink for at least about 30 minutes, at least about 1 hour, at least about 2 hours, or at least about 3 hours prior to the $FE_{NO}$ measurement.

In some aspects, to perform the $FE_{NO}$ procedure, the subject is standing in order to inhale to total lung capacity through the $FE_{NO}$ machine. In some aspects, for "on-line" FENO machines the FENO result (in parts per billion) can be displayed and/or recorded. In some aspects, for "off-line" systems air samples can be stored as appropriate and analyzed at a later date.

In some aspects, after reaching total lung capacity, the subject exhales for 10 seconds at 50 mL/sec. In some aspects, the specifics of the $FE_{NO}$ measurement adhere to the 2005 ATS $FE_{NO}$ testing criteria.

In some aspects, $FE_{NO}$ is measured after asthma inhaled and oral medications particularly corticosteroids have been constant for at least 6 weeks prior to testing. In some aspects, $FE_{NO}$ is measured in subjects who have experienced an upper or lower respiratory infections or other infections requiring antibiotics or antivirals have blood drawn at least 6 weeks after the completion of drug therapy. In some aspects, $FE_{NO}$ and CBC with differential measurements are performed on the same day.

White Blood Cell Counts and Other Analytes in Predictors

The classification methods of the present disclosure can comprise one or more predictors. A predictor used in a method or system of the disclosure can comprise any one or any combination of the following non-limiting examples of blood analytes: whole cell count of white blood cells (WBC), eosinophils, neutrophils, lymphocytes, CD3+ T cells, CD4+ T cells, CD4+CD25+ T cells, CD45+RO+ T cells, monocytes, CD3–CD56+ NK cells, and eosinophil precursors, basophil precursors, and levels of IL-1, IL-2, IL-3, IL-4, IL-5, IL-6, IL-7, IL-8, IL-9, IL-10, IL-12, IL-13, IL-17, IL-18, IL-23, IL-25, IL-33, eotaxin-1, eotaxin-2, eotaxin-3, ECP (eosinophil cationic protein), EDN (eosinophil-derived neurotoxin), MBP2 (major basic protein homolog), MCP-1 (monocyte chemotactic protein 1), MIF (macrophage migration inhibitory factor), TARC (Chemokine (C—C motif) ligand 17), TSLP (thymic stromal lymphopoietin), lipoxin A4, cysteinyl leukotrienes, serum periostin, and TGF-beta. Blood analytes can be measured by any method known to one of skill in the art.

In one aspect, blood analytes to use in predictors are determined from a complete blood cell count (CBC) with differential. In one aspect, the level of eosinophil or basophil precursors is determined by flow cytometry. In one aspect, a predictor used in a method of the disclosure can comprise WBC, eosinophil count, neutrophil count, lymphocyte count, eosinophil precursor count, basophil precursor count, Eotaxin-2 level and any combination thereof. In another aspect, a predictor used in a method or system of the disclosure can comprise WBC, eosinophil count, neutrophil count, and lymphocyte count. In a further aspect, a predictor used in a method or system of the disclosure can comprise the blood eosinophil/WBC ratio, the blood eosinophil/blood lymphocyte ratio and the log of the blood eosinophil/blood neutrophil ratio.

A predictor used in a method or system of the disclosure can comprise any one or any combination of the following non-limiting examples of physiological markers: ΔFEV1 post-albuterol, ΔFEV1 post-tiotropium bromide, FEV1, FEV/FVC, Δ AM/PM PEF variation, and $FE_{NO}$. The physiological markers can be determined following standard medical protocols.

A predictor used in a method or system of the disclosure can also comprise any one or any combination of patient symptom markers, such as, but not limited to, ACQ score, AQLQ score, Berlin Questionnaire (sleep apnea screen), Borg Score (assessment of dyspnea), previous sinus surgery, history of atopy, history of intubation, history of aspirin sensitivity, history of corticosteroid bursts during past 3 or 12 months, history of ER visits during past 3 years.

A predictor used in a method or system of the disclosure can also comprise any one or any combination of the following parameters: gender, age, weight, race, height, or body mass index (BMI).

In some aspects, a predictor can comprise a value corresponding to the average of several measurements from multiple samples collected at different time intervals. Thus, in some aspects, multiple samples can be collected at different intervals, e.g., about 1 day, about 2 days, about 3 days, about 4 days, about 5 days, about 6 days, or about 7 days apart. In some aspects, the multiple samples can be collected about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks apart. In some aspects, multiple samples can be collected about 1 month, about 2 months, about 3 months, about 4 months, about 5 months, about 6 months, about 7 months, about 8 months, about 9 months, about 10 months, about 11 months, or about 12 months apart. In some aspects, multiple samples can be collected more than 12 months apart. In some cases, more than 2 samples are averaged, for examples, 3 samples, 4 samples, 5 samples, 6 samples, 7 samples, 8 samples, 9 samples, 10 samples, or more than same samples. In some aspects, samples are collected are regular intervals. In other aspects, samples are not collected at regular intervals. In some cases, samples are collected in response to an event, for example, exacerbation of symptoms.

Ratios in Predictors

A predictor used in a method of the disclosure can comprise at least one of the following ratios or a function (e.g., logarithm) of any one of the following ratios: blood eosinophil count/blood neutrophil count, blood eosinophil count/ blood lymphocyte, Eotaxin-1 level/blood eosinophil count, Eotaxin-2 level/blood eosinophil count, Eotaxin-3 level/ blood eosinophil count, IL-5 level/blood eosinophil count, IL-5 level/IL-10 level, IL-13 level/IL-5 level, IL-5 level/ IFN-γ level, IL-10 level/Vitamin D level, TGF-β level/IgE level, IL-5 level/TGF-β level, IL-5 level/IL-8 level, ECP level/blood eosinophil count, EDN level/blood eosinophil count, MBP2 level/blood eosinophil count, blood eosinophil count/m2 level, Blood eosinophil count/BMI, Blood eosinophil count/FVC, $FE_{NO}$/Blood eosinophil count, blood eosinophil progenitors/blood eosinophil count, blood basophil progenitors/blood eosinophil count, CD4+ T cell count/ CD8+ T cell count, Blood eosinophil count/CD4+CD25+ cell count, CD4+CD25+ cell count/CD4+CD25− count, Blood eosinophil count/CD3+ T cell count, Blood eosinophil count/ serum periostin, serum periostin/blood lymphocyte count, Blood eosinophil count/total total serum IgE, total serum IgE/lymphocyte count, serum periostin/lymphocyte counts, serum periostin/neutrophil counts, total serum IgE/lymphocyte counts, total serum IgE/neutrophil counts, eosinophil count/Surfactant D level, IL-5 level/Surfactant D level, Blood eosinophil count/CD45+RO+ cell count, Blood eosinophil count/CD3−CD56+ cell count, blood eosinophil count/Vitamin D level, IL-5 level/Vitamin D level, Blood eosinophil count/Homocysteine level, IL-5 level/Homocysteine level, Lipoxin A4 level/Cysteinyl Leukotrienes level, IL-5 level/IL-12 level, IL-5 level/IL-3 level, IL-5 level/GM-CSF level. In a specific aspect, a predictor used in a method of the disclosure can comprise any one of the blood eosinophil count/blood neutrophil count, blood eosinophil count/blood lymphocyte, Eotaxin-2 level/blood eosinophil count, IL-5 level/IL-10 level, IL-5 level/TGF-β level, blood eosinophil progenitors/ blood eosinophil count, blood basophil progenitors/blood eosinophil count, blood eosinophil count/Vitamin D level, and IL-5 level/IL-12 level ratio or a function (e.g., logarithm) thereof. In a further specific aspect, a predictor used in a method of the disclosure can comprise the blood eosinophil count/white blood cell count, blood eosinophil count/blood lymphocyte count or blood eosinophil/blood neutrophil count.

Computational Model Construction

The present disclosure provides methods and systems for diagnosing, monitoring, administering a therapy, or managing therapy in a subject having a pulmonary disease or disorder. These methods are in turn based on the application of classification methods (e.g., the ELEN Method Index, the ELEN plus $FE_{NO}$ cutoff, or the EL-$FE_{NO}$ Index methods) based on the application of objective, probabilistic, multivariate statistical models. These models comprise one or more than one predictors for class prediction; wherein at least one predictor comprises a ratio of two cellular components from a white cell blood, for example a CBC with differential, wherein the model does not use sputum eosinophil count as a predictor.

Any suitable objective, probabilistic, multivariate statistical model known to one of skill in the art can be used to practice the methods and systems of the present disclosure. Non-limiting examples of the models that can be used to practice the methods of the present invention encompass supervised classification methods and include Fisher's Linear Discriminant Analysis, Logistic Regression, Naëve Bayesian, K-nearest neighbor classifier, Artificial neural networks, and Classification trees. In a specific embodiment, a method of the present invention utilizes Fisher's Linear Discriminant Analysis.

Machine learning methods suitable to practice white blood cell ratio-based methods applied to pulmonary diseases and disorders can include, for example, supervised learning methods (e.g., analytical learning, artificial neural networks, casebased reasoning, decision tree learning, inductive logic programming Gaussian process regression, gene expression programming, kernel estimators, support vector machines, random forests, ensembles of classifiers, etc.), unsupervised learning methods (e.g., neural networks with the self-organizing map (SOM) and adaptive resonance theory (ART)), semi-supervised learning method (e.g., constrained clustering, PU learning), reinforced learning methods (e.g., Monte Carlo methods), transductive inference methods (e.g., transductive support vector machines, Bayesian Committee machines), or multi-task learning methods (e.g., clustered multi-task learning).

Method of Use of Disclosed Methods and Systems

The methods and systems of the present disclosure can be applied to treating a patient or determining whether a patient will benefit from administration of a therapeutically effective dose of a therapeutic agent that is capable of treating a pulmonary disease or disorder, for example, reducing tissue eosinophil levels or tissue eosinophil activity. The methods and systems disclosed herein can be also used to monitor individuals who will develop a particular pulmonary disease. The application of the methods of systems disclosed herein can indicate increased and/or decreased likelihood that individuals susceptible to a pulmonary disease or disorder will develop symptoms associated with such pulmonary disease or disorder, such as eosinophilic asthma. This information is extremely valuable as it can be used, for example, to initiate preventive measures at an early stage, perform regular exams to monitor the progress and/or severity of the symptoms, and/or schedule exams at regular intervals to identify and monitor the pulmonary disease or disorder in question, so as to be able to apply treatment at an early stage.

The diagnosis and monitoring methods and systems disclosed herein can also be applied in determining a prognosis of a subject experiencing symptoms associated with, or a subject diagnoses with a pulmonary disease or disorder, for example, eosinophilic asthma. The prognosis predicted by the methods and systems of the present disclosure can be any type of prognosis relating to the progression of the pulmonary disease or disorder, and/or relating to the chance of recovering from the pulmonary disease or disorder. The prognosis can, for instance, relate to the severity of the pulmonary disease or disorder, or how the condition will respond to therapy.

In a further aspect, the methods and systems disclosed herein can be used to increase the power and effectiveness of clinical trials. Thus, individuals determined to have a particular pulmonary disease or disorder, are more likely to respond to a particular treatment modality. In a particular aspect, the methods and systems disclosed herein can be used to select subjects most likely to be responders to a particular treatment modality. In another aspect, the methods and systems disclosed herein can be used to select subjects most likely to be non-responders to a particular treatment modality.

The methods and systems disclosed herein can be used as part of suite of tools that a healthcare provider or healthcare benefits provider can apply depending, for example, on availability of samples and/or equipment, or particular preferences of doctors and/or patients. As a non-limiting example, the methods and system in the present disclosure that do not include the use of $FE_{NO}$ measurements, e.g., the ELEN Index method can be used to identify eosinophilic asthmatics if $FE_{NO}$ machines are not available. The ELEN Index method yields good overall diagnostic accuracy and is biased toward a positive predictive value (PPV). In some cases, patients do not want to be stuck with a needle to draw blood, and in such situations, a $FE_{NO}$ machine with 50 ppb as a cutoff can help to identify a small subset of eosinophilic asthmatics with high PPV. However, a $FE_{NO}$ 50 ppb cutoff has a very large false negative rate resulting in low negative predictive value (NPV). Thus for patients who are deemed negative by a $FE_{NO}$ 50 ppb cutoff, the ELEN Index method can be used as an "or" criterion. Thus, patients could be classified as positive for eosinophilic phenotype if they test positive either by a $FE_{NO}$ 50 ppb cutoff or by the ELEN Index method. In some cases, both drawing of blood for a CBC with differential and $FE_{NO}$ machines could be available to a physician and also acceptable to a patient. In this scenario, the disclosed method combining CBC with differential and $FE_{NO}$ measurements (which has a higher overall diagnostic accuracy than either of the alternatives discussed above and it is more balanced in relation to PPV and NPV) could be used to classify patients as either eosinophilic or non-eosinophilic.

Furthermore, the methods and systems provided herein can be used for classification, diagnosis, therapy, etc. beyond asthma. The ELEN Index method can be used in a positive fashion to identify patients suffering from an eosinophilic disease or disorder and, for example commence therapy to treat that eosinophilic disease or disorder. In the alternative, the ELEN Index method can be used is a negative fashion to confirm that a patient does not suffer from an eosinophilic disease or disorder. If such patient is currently receiving therapy which would be appropriate to treat an eosinophilic disease or disorder but inadequate to treat the pulmonary disease that the patient has, such therapy could be discontinued. By using a method such as the ELEN Index method in this later mode, the method can be used a tool to reach the correct diagnoses in any pulmonary disease or disorder and to prescribe the correct treatment.

The methods and systems provided herein can also classify with accuracy other inflammatory phenotypes of asthma, e.g., neutrophilic asthma. In addition, the disclosed methods can have an impact on future treatment guidelines for pulmonary diseases or disorder. For example, when a mild asthmatic requires a step-up in asthma therapy due to inadequate control of symptoms, the choice can be to increase the dose in inhaled corticosteroids or add a long-acting beta agonist. Currently, the best pathway to select is unclear. By identifying eosinophilic asthmatics which tend to be responsive to inhaled corticosteroids, this clinical decision can be answered accurately on an individual basis fostering the advancement of personalized medicine in the field of asthma. Furthermore, eosinophilic asthmatics are prime candidates to receive antibody therapeutics capable to achieve long term depletion of tissue eosinophils (e.g. anti-IL-5R antibody) without the side effect of long term corticosteroid therapy.

The disclosed methods and systems also have utility in other pulmonary diseases or disorders, such as chronic obstructive pulmonary disease (COPD) and infections of the lower respiratory track which can have symptoms similar to asthma. Accurate, non-invasive estimations of the levels of eosinophils and neutrophils in the lower airways in these diseases will help to provide precise, objective assessments that could result in better medical decisions and clinical outcomes.

Computer-Implemented Methods and Computer-Readable Media

The methods disclosed herein can be implemented, in all or in part, as computer executable instructions on known computer-readable media. For example, the methods described herein can be implemented in hardware. Alternatively, the methods can be implemented in software stored in, for example, one or more memories or other computer readable medium and implemented on one or more processors. The processors can be associated with one or more controllers, calculation units and/or other units in a computer system, or implanted in firmware as desired.

When implemented in software, the software can be stored in any computer readable memory such as in RAM, ROM, flash memory, a magnetic disk, a laser disk, or other storage medium, as is also known. Likewise, this software can be delivered to a user or computer device via any known delivery method including, for example, over a communication channel such as a telephone line, the internet, a wireless connection, etc., or via a transportable medium, such as a computer readable disk, flash drive, etc.

The steps of the disclosed methods and systems are operational with numerous general or special purpose computer system environments or configurations. Examples of well-known computing systems, environments, and/or configuration that can be suitable for use with methods or systems disclosed herein include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. The methods and systems can also be practiced in distributed computing environments where tasks are performed by remote processing devices that are linked through a communications network.

Computer-readable media can be any available media that can be accessed by computer and includes both volatile and nonvolatile media, removable and nonremovable media. By way of example, and not limitation, computer readable media can comprise computer storage media and communication media. Computer storage media includes both volatile and nonvolatile, removable and nonremovable media implemented in any method or technology for storage of information such as computer readable instructions, data structures, program modules or other data. Computer storage media includes, but it is not limited to, RAM, ROM, EEPROM, flash memory or other memory technology, CD-ROM, DVD or other optical disk storage, magnetic cassettes, magnetic tape, magnetic disk storage or other magnetic storage devices, or any other medium which can be used to store the desired information and which can be accessed by computer.

The computer implemented methods and computer-readable media disclosed herein can be used by patients and/or healthcare providers and/or healthcare benefit provider as a stand-alone tool or via a server, for example, a web server. The tool can include computer-readable components, an input/output system, and one or more processing units. The input/output system can be any suitable interface between user and computer system, for input and output of data and other information, and for operable interaction with the one or more processing units. In one aspect, data to be inputted into the tool can be derived from one source, for example, a doctor or a clinical laboratory. In one aspect, data to be inputted into the tool can be derived from more than one source, for example, a doctor and a clinical laboratory. In some aspects, the input/output system can provide direct input from measuring equipment. The input/output system preferably provides an interface for a standalone computer or integrated multi-component computer system having a data processor, a memory, and a display. Data can be entered numerically, as a mathematical expression, or as a graph. In some aspects, data can be automatically or manually entered from an electronic medical record.

In some aspects, data is electronically inputted into the tool from an electronic medical record or from a clinical laboratory, healthcare provider, or healthcare benefits provider data server. In some aspects, data is outputted from the tool and electronically sent, e.g., via secure and encrypted email, to a clinical laboratory, healthcare provider, healthcare benefits provider, or patient.

In some aspects, the present disclosure provides a computer-readable medium containing instructions for:
(a) identifying a patient as a candidate for a therapy to treat a pulmonary disease or disorder; and/or
(b) identifying a candidate therapy to treat a pulmonary disease or disorder; and/or,
(c) diagnosing a pulmonary disease or disorder in a patient to provide a therapy to said patient; and/or,
(d) managing the administration of a therapy to treat a pulmonary disease or disorder by a healthcare provider; and/or,
(e) managing the administration of a therapy of a pulmonary disease or disorder by a healthcare benefits provider;

wherein execution of the program instructions by one or more processors of a computer system causes the one or more processors to carry out the steps of:
(a) processing inputted data obtained from a white blood cell count obtained from a sample obtained from the patient; and,
(b) calculating a diagnostic score from a white blood cell ratio obtained from the processed inputted data;
wherein the diagnostic score:
(a) identifies the patient as a candidate for a therapy to treat the pulmonary disease or disorder; and/or,
(b) identifies the candidate therapy to treat the pulmonary disease or disorder; and/or,
(c) diagnoses the pulmonary disease or disorder in the patient; and/or,
(d) is used by the healthcare provider for managing the treatment of the pulmonary disease or disorder; and/or,
(e) is used by the healthcare benefits provider for managing the treatment of the pulmonary disease or disorder.

In some aspects, the pulmonary disease is a chronic pulmonary disease, for example asthma or chronic pulmonary disease (COPD). The pulmonary disease can be a pulmonary eosinophilic disease, for example, eosinophilic asthma.

In some aspects, the computer readable medium comprises instructions to calculate two scores, for example, a Score 1 and a Score 2, wherein Score 1 is calculated according to the formula:

$$\text{Score 1} = a + [b \times \text{blood eosinophil/blood lymphocyte}] - [c \times \text{natural log(blood eosinophil/blood neutrophil)}];$$

and Score 2 is calculated according to the formula:

$$\text{Score 2} = d + [e \times \text{blood eosinophil/blood lymphocyte}] - [f \times \text{natural log(blood eosinophil/blood neutrophil)}],$$

wherein:
(a) a is between about −74 and about −6;
(b) b is between about 45 and about 412;
(c) c is between about −38 and about −2;
(d) d is between about −95 and about −10;
(e) e is between about 65 and about 473; and,
(f) f is between about −39 and about −2,
wherein a Score 1≤Score 2 indicates that the patient has an eosinophilic disease or disorder.

In some aspects, a is about −10, b is about 70, c is about 4, d is about −15, e is about 101, and f is about 4, in the equations described above to calculate Score 1 and Score 2. In some aspects, a is −9.5243233, b is 70.0974823, c is 3.7789926, d is −14.5853365, e is 101.2197561, and f is 3.9567050, in the equations described above to calculate Score 1 and Score 2.

In some aspects, the inputted data comprises $FE_{NO}$ measurements, BMI measurements, or measurements corresponding to other analytes.

In other aspects, the computer readable medium comprises instructions to calculate two scores, for example, a Score 1' and a Score 2', wherein Score 1' is calculated according to the formula:

$$\text{Score } 1'=a'+(b'\times FE_{NO}\text{ ppb})-[c'\times \text{natural log(blood eosinophil/blood lymphocyte)}]$$

and Score 2 is calculated according to the formula:

$$\text{Score } 2'=d'+(e'\times FE_{NO}\text{ ppb})-[f\times \text{natural logarithm (blood eosinophil/blood lymphocyte)}]$$

wherein:
(a) a' is between about −14 and about −4.0;
(b) b' is between about 0.01 and about 0.17;
(c) c' is between about −10 and about −2;
(d) d' is between about −10.2 and about −3.3;
(e) e' is between about 0.03 and about 0.18; and,
(f) f' is between about −8 and about −1.4,
wherein a Score 1'≤Score 2' indicates that the patient has an eosinophilic disease or disorder.

In some aspects, a' is about −5, b' is about 0.03, c' is about 2.5, d' is about −3.5, e' is about 0.05, and f' is about 2, in the equations described above to calculate Score 1' and Score 2'. In some aspects, a' is −4.6368456, b' is 0.0300382, c' is 2.5409793, d' is −3.6017103, e' is 0.0559650, and f' is 1.7349461, in the equations described above to calculate Score 1' and Score 2'.

In some aspects, the instructions for execution in the computer-readable medium are executed iteratively using measurements from samples collected at least one week apart. In other aspects, the instructions for execution in the computer-readable medium are executed iteratively using measurements from samples collected at least two weeks apart. In yet other aspects, the instructions for execution in the computer-readable medium are executed iteratively using measurements from samples collected at intervals disclosed elsewhere in the present disclosure.

Any methods of the present disclosure and all their variants (e.g., using different mathematical approaches to computational model construction, using different type and number of analytes, using different type and number of predictors, applications to different types of therapy and therapeutic agents, applications to different types of pulmonary diseases or disorders, etc.) can be implemented in computer-readable media and in computer systems comprising the disclosed computer-readable media and/or computer-implementations of the disclosed methods.

Therapeutic Agents for Treatment of Pulmonary Diseases and Disorders

In one aspect of the disclosed methods and systems, the therapeutic agent is a small molecule drug. In a specific aspect, the agent is a corticosteroid. In another aspect, the agent can be a leukotriene modifier such as montelukast, zafirlukast or zileuton. In a further aspect, the therapeutic agent can be a methylxanthine (e.g., theophylline) or a cromone (e.g., sodium cromolyn and nedocromil). In another aspect, the therapeutic agent can be a long-acting beta-2 agonist such as salmeterol, fomoterol, or indacaterol. In a further aspect, the agent can be methotrexate or cyclosporin.

In certain aspects, the therapeutic agent can be an agent used for preventing, treating, managing, or ameliorating asthma. Non-limiting examples of therapies for asthma include anti-cholinergics (e.g., ipratropium bromide and oxitropium bromide), beta-2 antagonists (e.g., albuterol (PROVENTIL® or VENTOLIN®), bitolterol (TOMA-LATE®), fenoterol, formoterol, isoetharine, metaproterenol, pibuterol (MAXAIR®), salbutamol, salbutamol terbutaline, and salmeterol, terbutlaine (BRETHAIRE®)), corticosteroids (e.g., prednisone, beclomethasone dipropionate (VAN-CERIL® or BECLOVENT®), triamcinolone acetonide (AZMACORF®), flunisolide (AEROBID®), and fluticasone propionate (FLOVENT®)), leukotriene antagonists (e.g., montelukast, zafirlukast, and zileuton), theophylline (THEO-DUR®, UNIDUR® tablets, and SLO-BID® Gyrocaps), and salmeterol (SEREVENT®), cromolyn, and nedorchromil (INTAL® and TILADE®)), IgE antagonists, IL-4 antagonists (including antibodies), IL-5 antagonists (including antibodies), PDE4 inhibitors, NF-Kappa-B inhibitors, IL-13 antagonists (including antibodies), CpG, CD23 antagonists, selectin antagonist (e.g., TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine), C2a receptor antagonists (including antibodies), and supportive respiratory therapy, such as supplemental and mechanical ventilation.

In certain aspects, an effective amount of one or more IL-9 antagonists are administered in combination of one or more supportive measures to a subject to prevent, treat, manage, or ameliorate asthma or one or more symptoms thereof. Non-limiting examples of supportive measures include humidification of air by ultrasonic nebulizer, aerosolized racemic epinephrine, oral dexamethasone, intravenous fluids, intubation, fever reducers (e.g., ibuprofen and acetametaphine), and antibiotic, anti-viral, or anti-fungal therapy (i.e., to prevent or treat secondary respiratory infections).

In another aspect, the therapeutic agent is a biologic. In certain aspects, the biological is any substance made by a living organism or its products, a substance made using recombinant DNA technology, a nucleotide, a nucleotide analogue, an oligonucleotide, an oligonucleotide analogue, a peptide, or a peptide analogue produced by any means. In specific aspects, a biologic can be an antibody or antibody fragment, an antibody mimetic, a soluble receptor polypeptide, a soluble receptor fusion polypeptide, interleukin, interleukin fusion polypeptide, antisense molecule, siRNA or miRNA.

In one aspect, the therapeutic agent used according to methods of the invention described herein is an antibody. The term "antibody" as referred to herein encompasses whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1 CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The variable regions of the heavy and light chains contain a binding domain that interacts with an antigen. The constant regions of the antibodies can mediate the binding of the immunoglobulin to host tissues or factors, including various cells of the immune system (for example, but not limited to, effector cells) and the first component (C1q) of the classical complement system. Antibodies can be derived from any mammal, including, but not limited to, humans, monkeys, pigs, horses, rabbits, dogs, cats, mice, etc. The term "antibody" refers to monoclonal antibodies, multispecific antibodies, human antibodies, humanized antibodies, camelized antibodies, chimeric antibodies, single-chain Fvs (scFv), single chain antibodies, single domain antibodies, Fab fragments, F(ab') fragments, disulfide-linked Fvs (sdFv), and anti-idiotypic (anti-Id) antibodies (including, for example, but not limited to, anti-Id antibodies to antibodies of the disclosure), intrabodies, and epitope-binding fragments of any of the above. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., IL-5R). It has been shown that the antigen-binding function of an antibody can be performed by fragments of a full-length antibody. Examples of binding fragments encompassed within the term "antigen-binding portion" of an antibody include, but are not limited to, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (for example, but not limited to, mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

In a specific aspect, the therapeutic agent is an antibody or biologically active fragment or derivative thereof. Antibodies or biologically active fragment or derivative thereof that can be used according to the methods of the disclosure include, but are not limited to, anti-human IL-5 antibodies and anti-human IL-5 receptor alpha antibodies.

In one aspect, the therapeutic agent can be an anti-IL-5 or anti-IL5 receptor antibody. In one aspect, the therapeutic agent can be a human, humanized or chimeric antibody. In one aspect, the therapeutic agent can be an antibody with increased effector function. In one aspect, the therapeutic agent can be an antibody with increased ADCC activity. In one aspect, the therapeutic agent can be an afucosylated antibody. In one aspect, the therapeutic agent can be an antibody comprising complex N-glycoside-linked sugar chains bound to the Fc region in which fucose is not bound to N-acetylglucosamine in the reducing end in the sugar chain. In one aspect, the therapeutic agent can be an antibody with increased in vivo half-life.

Without being bound by a particular theory, the therapeutic agent used according to the methods described herein can be an IL-5 or IL-5 receptor ("IL-5R") antagonist. As used herein, the term "antagonist" refer to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of another molecule.

IL-5 or IL-5 receptor antagonists that can be utilized in accordance with the present disclosure include, but are not limited to, proteinaceous agents (e.g., proteins, polypeptides, peptides, fusion proteins, antibodies, and antibody fragments), nucleic acid molecules (e.g., IL-5 or IL-5R targeting antisense nucleic acid molecules, triple helices, double-stranded RNA, or DNA encoding double-stranded RNA that mediates RNAi, or nucleic acid molecules encoding proteinaceous agents), organic molecules, inorganic molecules, small organic molecules, drugs, and small inorganic molecules that block, inhibit, reduce or neutralize a pathologic cellular or humoral phenotype associated with or resulting from IL-5 or IL-5R expression and/or activity (e.g., eosinophil proliferation or survival, binding of IL-5 to the IL-5 receptor).

In a specific aspect, an IL-5 or IL-5 receptor antagonist is an antibody or fragment thereof that immunospecifically binds to an IL-5 polypeptide. In another aspect, an IL-5 or IL-5 receptor antagonist is an antibody or fragment thereof that immunospecifically binds to an IL-5R or a subunit thereof.

In one aspect, the therapeutic agent can be an anti-IL-5 or anti-IL5R antibody capable of preventing the signaling of IL-5 through the IL-5 receptor. Non-limiting examples of anti-human IL-5 antibodies are reslizumab, and mepolizumab. Non-limiting examples of anti-human IL-5 receptor alpha antibodies of the disclosure can be found in U.S. Pat. Nos. 7,179,464, 6,538,111, 6,018,032, and U.S. Patent Application Publication Nos. 2004/0136996A1, 2005/0226867A1. In one aspect, the therapeutic agent can be an antibody directed against IL-5, e.g., reslizumab, mepolizumab, and any combination thereof.

Without being bound by a particular theory, the therapeutic agent used according to the methods and systems described herein can be an anti-IL-5 receptor antibody capable to mediate the in vivo depletion of eosinophils. In one aspect, the in vivo depletion can be mediated by ADCC, CDC or antibody mediated phagocytosis. In a specific aspect, the therapeutic agent can be an anti-IL-5R antibody having ADCC activity.

In one aspect, the therapeutic agent can be an anti-cytokine antibody. In other aspects, the antibody can be an anticytokine receptor antibody.

In another specific aspect, the therapeutic agent can be an anti-IL-5R antibody having increased ADCC activity. A non-limiting example for an anti-IL-5R antibody with increased ADCC activity is benralizumab (also referred to herein as "MEDI-563" as described in WO 2008/143878). Benralizumab is an immunoglobulin G1 antibody comprising humanized mouse monoclonal MEDI-523 γ1 heavy chain (224-214')-disulfide with humanized mouse monoclonal MEDI-523 κ light chain, dimer (230-230":233-233")-bisdisulfide.

In a specific aspect, the therapeutic agent can be benralizumab (see, WO 2008/143878). In another aspect, the anti-IL-5R (CD125) antibody comprises the same three variable heavy complementarity determining regions (VHCDR) as shown in SEQ ID NO: 3 or 4 and the same three variable light complementarity determining regions (VLCDR) as shown in SEQ ID NO: 1 or 2. In certain aspects, the anti-IL-5R antibody comprises the variable heavy sequence as shown in SEQ ID NO: 3 or 4 and the variable light sequence as shown in SEQ ID NO: 1 or 2. In another specific aspect, the therapeutic agent can be an anti-IL-5 receptor antibody that binds the same epitope as benralizumab. The benralizumab epitope is described in WO 2008/143878, the disclosure of which is hereby incorporated by reference for all purposes.

In another aspect, the therapeutic agent can be an antibody directed against IL-13/IL-4α. In a specific embodiment, the therapeutic agent can be Aerovant™ (Aerovance), GSK-679586 (GSK), IMA-026 (Wyeth), or MILR1444A (Genentech).

In a further aspect, the therapeutic agent can be an antibody directed against the IL-2 receptor. In a specific embodiment, the therapeutic agent can be daclizumab (Zenapax). Daclizumab is a therapeutic humanized monoclonal antibody to the alpha subunit of the IL-2 receptor of T cells In another aspect, the therapeutic agent can be an anti-IgE antibody. In a specific embodiment, the therapeutic agent can be omalizumab (Xolair®). Omalizumab is a recombinant DNA-derived humanized IgG1k monoclonal antibody that selectively binds to human immunoglobulin E (IgE). Omalizumab is FDA-approved to treat moderate to severe allergic asthmatics. It has not been specifically approved for treatment of eosinophilic asthma though some studies have demonstrated it decreases airway eosinophil numbers.

In another aspect, the therapeutic agent can be a recombinantly-produced cytokine. In a specific embodiment, the therapeutic agent can be interferon-alpha. Non-limiting examples of interferon-alpha therapeutics include PEGASYS® (PEGinterferon alfa-2a) and Albuferon®/Zalbin™ (albinterferon alfa-2b).

In one aspect, the glycosylation of antibodies or antigen-binding fragment thereof utilized in accordance with the disclosure is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies can be produced in bacterial cells which lack the necessary glycosylation machinery.

An antibody or antigen-binding fragment thereof can also be made that has an altered type of glycosylation, such as a hypofucosylated antibody having reduced amounts of fucosyl residues or an antibody having increased bisecting GlcNAc structures. In one embodiment, an antibody or antigen-binding fragment thereof used in accordance with the methods and systems described herein has complex N-glycoside-linked sugar chains bound to the Fc region in which fucose is not bound to N-acetylglucosamine in the reducing end in the sugar chain. Such altered glycosylation patterns have been demonstrated to increase the ADCC ability of antibodies. Such carbohydrate modifications can be accomplished by, for example, expressing the antibody in a host cell with altered glycosylation machinery.

Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as, U.S. Pat. No. 6,946,292; European Patent No: EP 1,176,195; PCT Publications WO 03/035835; WO 99/54342 each of which is incorporated herein by reference in its entirety.

An antibody or fragment thereof to use according to the methods and systems of the present disclosure can be modified with respect to effector function, so as to enhance the effectiveness of the antibody in treating pulmonary diseases, for example, eosinophilic diseases. For example, cysteine residue(s) can be introduced in the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, Caron et al., *J. Exp Med.*, 176:1191-1195 (1992) and Shopes, B., *J. Immunol.*, 148:2918-2922 (1992). Homodimeric antibodies with enhanced activity can also be prepared using heterobifunctional cross-linkers as described in Wolff et al., *Cancer Research*, 53:2560-2565 (1993). An antibody can also be engineered which has dual Fc regions and can thereby have enhanced complement lysis and ADCC capabilities. See, Stevenson et al., *Anti-Cancer Drug Design*, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication Nos. WO 2004/063351, to Stavenhagen et al., the disclosure of which is incorporated herein in its entirety).

In certain aspects, the half-life of an antibody or antigen-binding fragment thereof used according to the methods and systems of the present disclosure is at least about 4 to 7 days. In certain aspects, the mean half-life of an antibody used according to the methods and systems of the present disclosure is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other aspects, the mean half-life of an antibody used according to the methods and systems of the present disclosure is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days.

In still further aspects, the half-life of an antibody or antigen-binding fragment thereof used according to the methods and systems of the present disclosure can be up to about 50 days. In certain aspects, the half-lives of antibodies used according to the methods and systems of the disclosure can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/3461.

The serum circulation of antibodies or antigen-binding fragment thereof in vivo can also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography.

PEG-derivatized antibodies or antigen-binding fragments thereof can be tested for binding activity as well as for in vivo efficacy using methods known to those of skill in the art, for example, by immunoassays described herein. Further, antibodies or antigen-binding fragment thereof can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413,622, all of which are incorporated herein by reference in their entireties.

In some aspects, the prophylactic or therapeutic agent can be any polypeptide (e.g., an antibody, small peptide, fusion protein or conjugate), polynucleotide, small molecule drug, or combination thereof that can be administered to treat or prevent a pulmonary disease or disorder, e.g., an eosinophilic disease or disorder such as eosinophilic asthma.

The amount of a prophylactic or therapeutic agent or a composition which will be effective in the treatment, management, prevention, or amelioration of a pulmonary disease or disorder, e.g., an eosinophilic disease or disorder, or one or more symptoms thereof can be determined by standard clinical methods. The frequency and dosage will vary according to factors specific for each patient depending on the specific therapy or therapies (e.g., the specific therapeutic or prophylactic agent or agents) administered, the severity of the disorder, disease, or condition, the route of administration, as well as age, body, weight, response, and the past medical history of the patient. For example, the dosage of a prophylactic or therapeutic agent or a composition which will be effective in the treatment, prevention, management, or amelioration of a pulmonary condition, e.g., an eosinophilic disease or disorder, or one or more symptoms thereof can be determined by administering the composition to an animal model such as, e.g., the animal models disclosed herein or known to those skilled in the art. In addition, in vitro assays can optionally be employed to help identify optimal dosage ranges. Suitable regimens can be selected by one skilled in the art by considering such factors and by following, for example, dosages reported in the literature and recommended in the *Physician's Desk Reference* (57th ed., 2003).

In aspects of the disclosure wherein antibodies, proteins, polypeptides, peptides and fusion proteins are administered to treat, manage, prevent, or ameliorate an a pulmonary disease or disorder, e.g., an eosinophilic disease or disorder or one or more symptoms thereof, the dosage administered to a patient is 0.0001 mg/kg to 100 mg/kg of the patient's body weight. In specific aspects, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg, or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof can be reduced by enhancing uptake and tissue penetration of the antibodies by modifications such as, for example, lipidation.

In a specific aspect, the methods and systems of the present disclosure comprise the administration of an antibody in a dosage that is 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

In another aspect, the dosage of the antibody that is administered to prevent, treat, manage, or ameliorate a pulmonary disease or disorder, for example an eosinophilic disease or disorder, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 mg to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg. In another aspect, the dosage of the antibody that is administered to prevent, treat, manage, or ameliorate a pulmonary disease or disorder, for example an eosinophilic disease or disorder, or one or more symptoms thereof in a patient is a unit dose of about 10 mg, about 20 mg, about 30 mg, about 40 mg, about 50 mg, about 60 mg, about 70 mg, about 80 mg, about 90, about 100 mg, about 110 mg, about 120 mg, about 130 mg, about 140 mg, about 150 mg, about 160 mg, about 170 mg, about 180, about 190 about or about 200 mg. In another aspect, the dosage of the antibody that is administered to prevent, treat, manage, or ameliorate a pulmonary disease or disorder, for example an eosinophilic disease or disorder, or one or more symptoms thereof in a patient is a unit dose of at least about 10 mg, at least about 20 mg, at least about 30 mg, at least about 40 mg, at least about 50 mg, at least about 60 mg, at least about 70 mg, at least about 80, at least about 90, at least about 100, at least about 110, at least about 120, at least about 130, at least about 140, at least about 150, at least about 160, at least about 170, at least about 180, at least about 190, or at least about 200 mg.

All patents and publications referred to herein are expressly incorporated by reference in their entireties.

EXAMPLES

Example 1

A Predictive Statistical Model (ELEN Index) Using Peripheral Blood Cell Counts Successfully Categorizes Asthmatics into Sputum Eosinophilic and Non-Eosinophilic Phenotypes Materials and Methods To develop and validate a statistical model for predicting eosinophilic asthma, we used data from a clinical trial (CP-138) conducted by MedImmune for testing one of its proprietary compounds (MEDI-528), an anti-IL-9 antibody. We used a multivariate technique, Linear Discriminant Analysis (LDA), for developing a prediction algorithm (McLachlan, G. J., 1992; Huberty, C. J., 1994). The statistical software SYSTAT v. 11.0.0.1 was used for data analyses (SYSTAT, 2004).

Independent validation of the prediction model was carried out with a different dataset obtained from Astra Zeneca (AZ). from later time-points at which the study subjects were given different allergen challenges. Only data from subjects in the placebo arm were used for this validation in order to exclude any potential effects of Medi-528 treatment. This validation dataset (n=99; hereafter referred to as Cohort 1) was comprised of post-allergen challenges at 7 different time points;
(3) an independent dataset obtained from AZ (n=75; hereafter referred to as Cohort 2); and,
(4) after combining Cohorts 1 and 2 (n=174). We tested the robustness of our prediction algorithm using bootstrap-resampling (n=5000).

Results and Discussion

Although there have been numerous attempts to use peripheral blood eosinophil counts for predicting sputum eosinophilia, the correlation between the 2 types of eosinophil measurements was not strong. We have observed the correlations between the dependent variable (sputum EOS %) and selected CBC measures (potential predictors) to be relatively weak (TABLE 1).

Figure 1B:
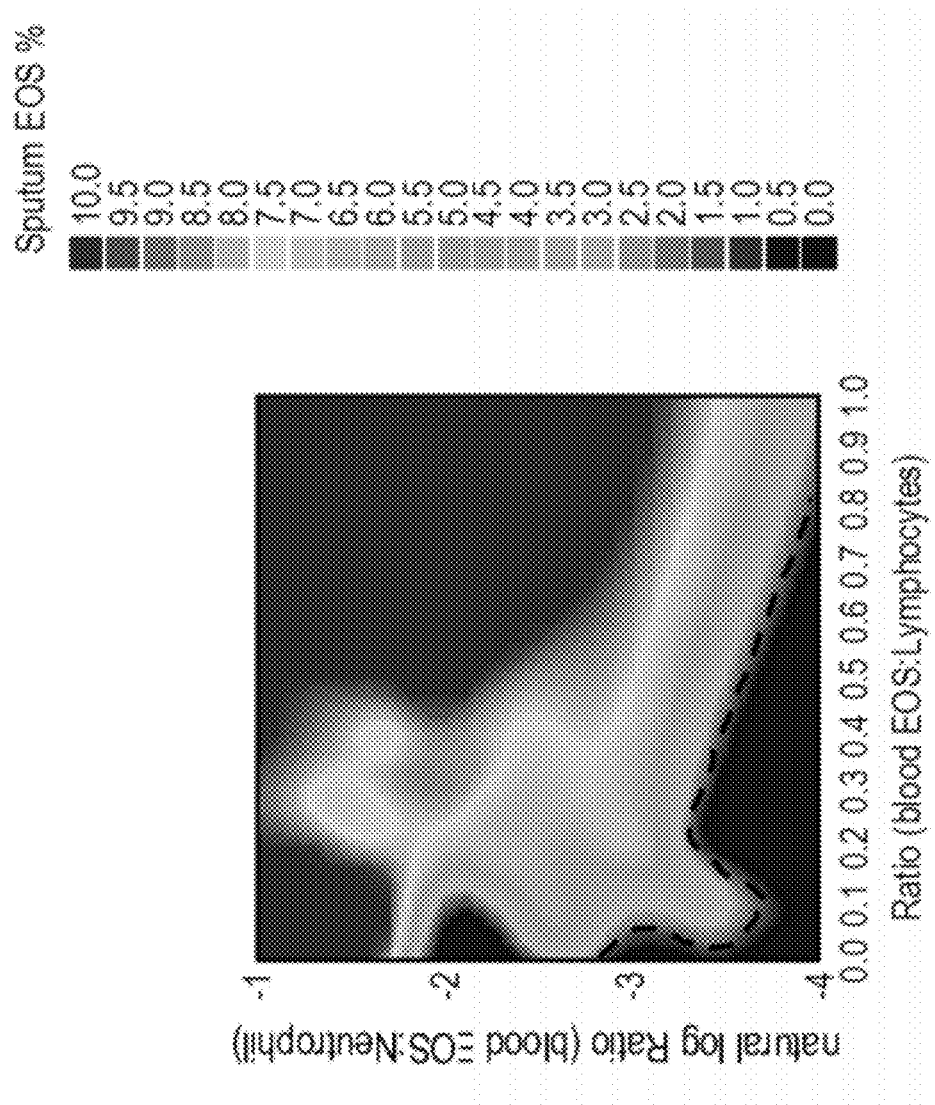
FIG. 1B shows a heatmap correlating the ratio between blood eosinophils and blood lymphocytes versus the natural logarithm of the ratio between blood eosinophils and blood neutrophils. The dashed line indicates separation between sputum eosinophilic and non-eosinophilic asthmatics.

The Pearson correlation coefficient for sputum EOS % and blood eosinophil counts in TABLE 1 was only 12%. The vertical striations on the different shades in FIG. 1A indicated poor correlation between blood eosinophil counts and Sputum EOS %, implying low predictive value for prediction on a continuous scale. On the other hand, FIG. 1B showed a diagonal shift in the shades, implying that ratios of blood eosinophil/lymphocyte and the natural logarithm of the ratio of blood eosinophil/neutrophil, when used jointly, had higher correlation with sputum EOS % and, therefore, higher predictive capability.

TABLE 1

Correlation of selected CBC measures among one another and with Sputum EOS %, the dependent variable (CP-138 Pre-AC data; n = 23).

(GROUP$ = 'Pre-AC')
Means

| SPU_EOS_PCNT | WBC | ABS_EOS | LNRATBLDEOSW | RAT_EOS_LYM | LNRAT_E_N |
|---|---|---|---|---|---|
| 3.6104348 | 5.7695652 | 0.2043478 | −4.0525393 | 0.1115597 | −3.4254858 |

Pearson correlation matrix

|  | SPU_EOS_PCNT | WBC | ABS_EOS | LNRATBLDEOSW | RAT_EOS_LYM | LNRAT_E_N |
|---|---|---|---|---|---|---|
| SPU_EOS_PCNT | 1.0000000 | | | | | |
| WBC | −0.2449369 | 1.0000000 | | | | |
| ABS_EOS | 0.1207729 | 0.3722584 | 1.0000000 | | | |
| LNRATBLDEOSW | 0.1490068 | −0.2813414 | 0.4429994 | 1.0000000 | | |
| RAT_EOS_LYM | 0.2290246 | 0.0618334 | 0.8753002 | 0.4701469 | 1.0000000 | |
| LNRAT_E_N | 0.1468377 | −0.2995628 | 0.4405196 | 0.9989932 | 0.4630925 | 1.0000000 |

The CP-138 clinical trial was conducted on 30 mild asthmatics all of whom underwent an allergen bronchial challenge and subsequently received the anti-IL-9 treatment. The 30 mild asthmatics were randomly divided into two groups: a placebo arm and a treatment arm. The prediction model was constructed using the pre-allergen challenge (pre-AC) data from both treatment arms (n=23; 7 cases were dropped due to missing values).

Figure 3:
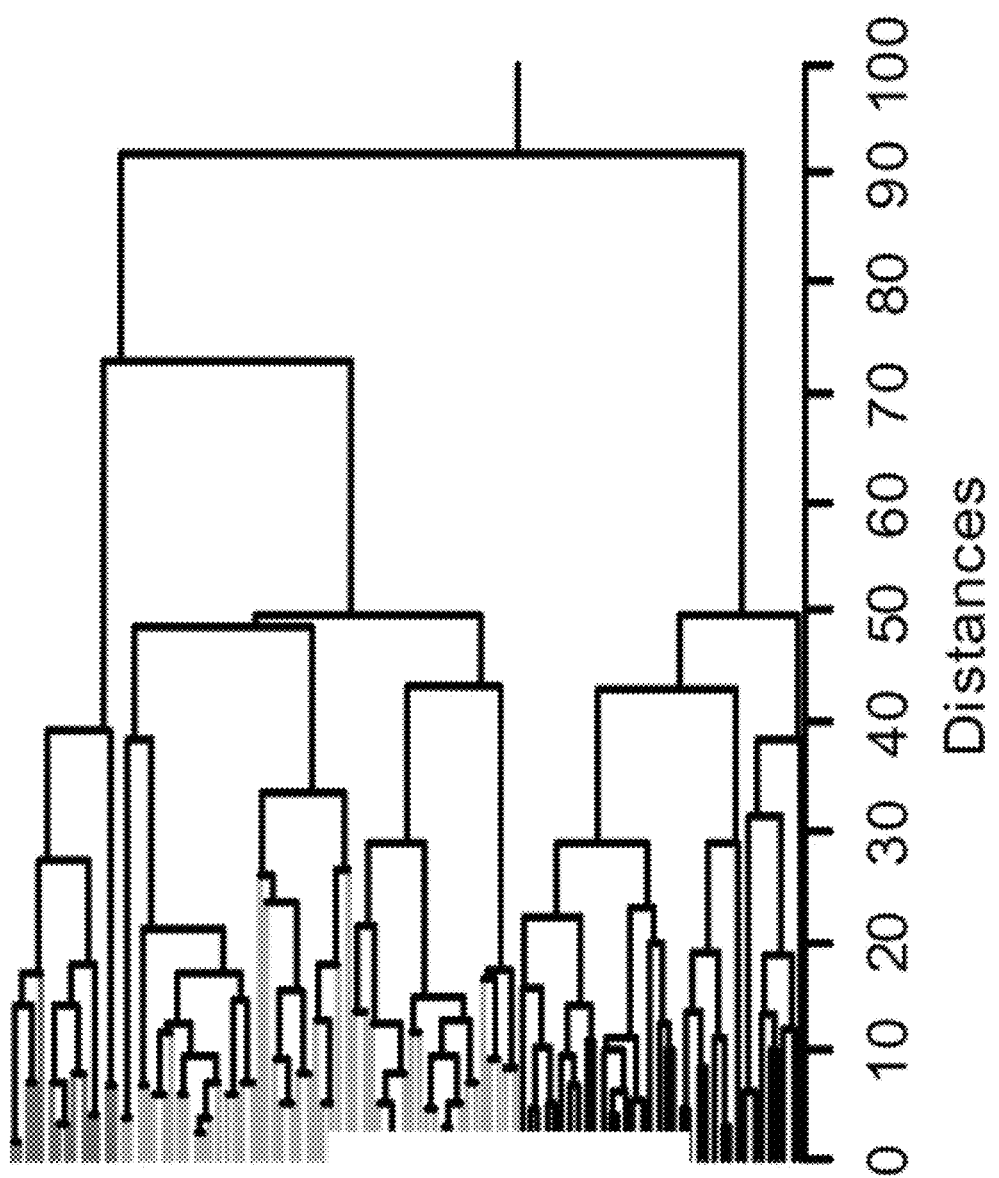
FIG. 3 shows an average-linkage hierarchical clustering of "variable X" and "variable Y" in the simulated dataset using Euclidean distances. Individual cases cluster into 2 main groups (gray: group A; black: group B).
Figure 4:
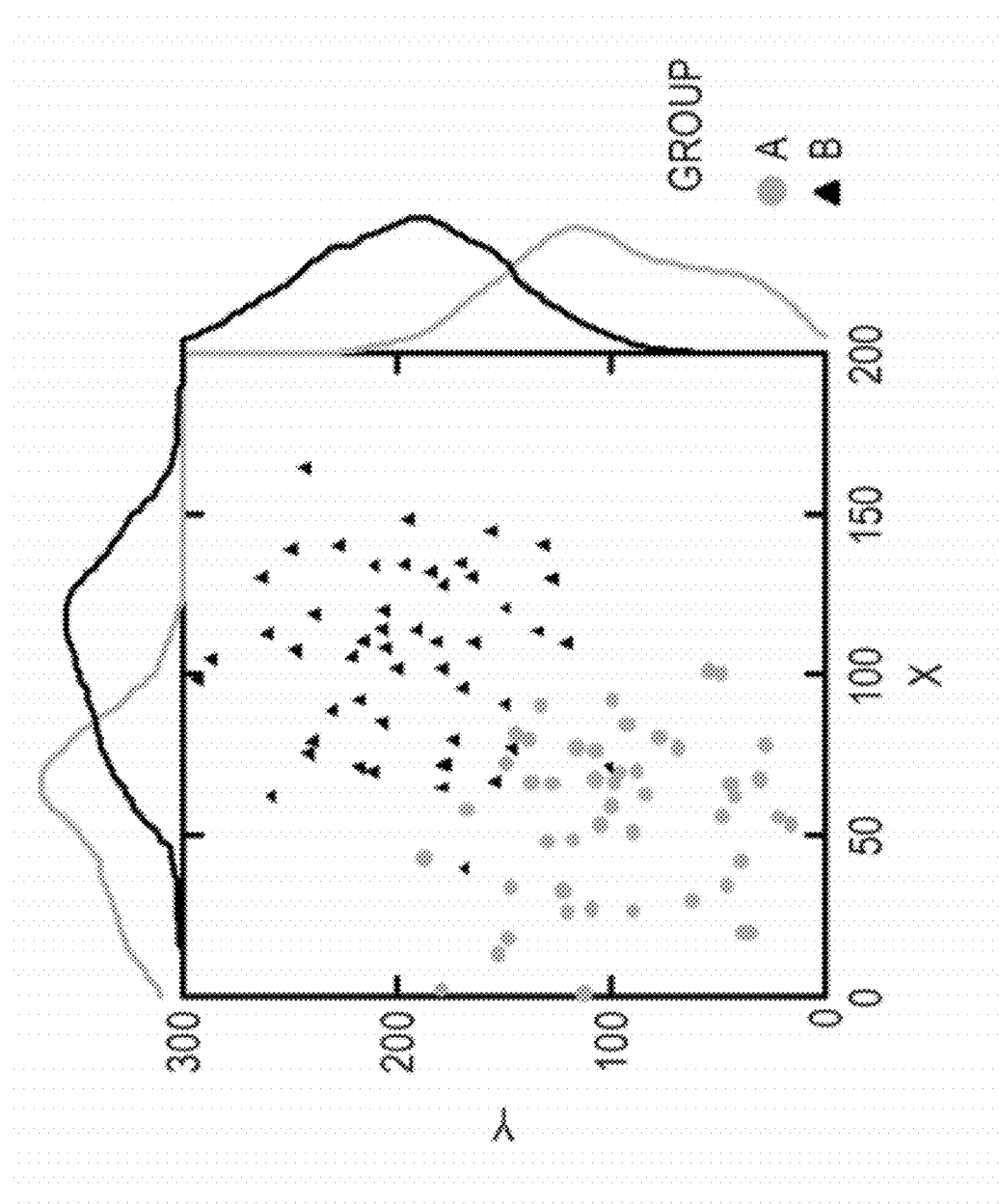
FIG. 4 shows a plot of "variable X" versus "variable Y" in the simulated data set, showing that data points segregate into two distinct subgroups (groups A and B) as identified by grey circles and black triangles.

Four different model validations were carried out to test the accuracy and predictive values of the algorithm:
(1) a leave-one-out (jackknife) cross-validation of the 23 cases used to develop the prediction model (n=23);
(2) a validation of the model on additional CP-138 data (i.e., data not used in building the model), which consisted of data We have found that that strong correlation between independent and a single dependent variable was not necessary for a class prediction to be successful. We demonstrated that strong correlation between a dependent and independent variable is not necessary to obtain high binary classification accuracy by artificially creating a simulated dataset using a Mersenne-Twister random number generator and normal distributions in SYSTAT. The simulated dataset comprised two variables, arbitrarily designated "variable Y" and "variable X," and two data point subgroups (n per each subgroup=50), designated "group A" and "group B." TABLES 2 and 3 and FIGS. 2, 3 and 4 show results from this simulation.

TABLE 2 shows the means of each variable (X=79.9, Y=144.7) and the Pearson correlation coefficient (r=0.47) of the two variables. A moderate level of linear correlation (47%) was observed (FIG. 2). Despite this moderate level of correlation, the average-linkage hierarchical clustering of "variable X" and "variable Y" in the simulated dataset using Euclidean distances (FIG. 3) showed that there were 2 major and distinct classes in the combined dataset, corresponding to "group A" and "group B." This segregation into two distinct groups became quite evident when the data was represented as a scatter chart in FIG. 4, which showed that the individual data points clustered in the lower left and upper right quadrants for "group A" and "group B," respectively.

TABLE 2

Correlation (Pearson's r) between the X and Y variables in the artificially created dataset.

|   | X | Y |
|---|---|---|
| Means | | |
|   | 79.9492360 | 144.7195262 |
| Pearson correlation matrix | | |
| X | 1.0000000 | |
| Y | 0.4742606 | 1.0000000 |

The data in TABLE 3 showed that despite only 47% linear correlation between "variable Y" and "variable X," "variable Y" successfully classified individual "variable X" measurements into either "group A" or "group B." The results of leave-one-out cross-validation showed the overall classification accuracy to be 87% with the following sub-accuracies: 84% specificity, 90% sensitivity, 89% negative predictive value (NPV), and 85% positive predictive value (PPV). This clearly demonstrated that high correlation between a response and a predictor variable was not necessary for successful binary classification, such as for use in medical screening or diagnostic tests.

TABLE 3

Classification of X into A and B groups using the Y measurements as a predictor variable

| Classification functions | | |
|---|---|---|
|   | A | B |
| CONSTANT | −2.7279186 | −9.8285086 |
| Y | 0.0438517 | 0.0929162 |

|   | A | B | % correct |
|---|---|---|---|
| 1. Prediction Model: Classification matrix (cases in row categories classified into columns) | | | |
| A | 43 | 7 | 86 |
| B | 5 | 45 | 90 |
| Total | 48 | 52 | 88 |
| 2. Cross-validation: Jackknifed classification matrix | | | |
| A | 42 | 8 | 84 |
| B | 5 | 45 | 90 |
| Total | 47 | 53 | 87 |

In our initial model, we identified 3 CBC-derived predictor variables for classifying eosinophilic and non-eosinophilic asthmatics, all of which were white blood cell ratios or functions thereof:

(i) blood eosinophil/blood lymphocyte;
(ii) blood eosinophil/blood leucocyte; and,
(iii) natural log(blood eosinophil/blood neutrophil).

Figure 5A:
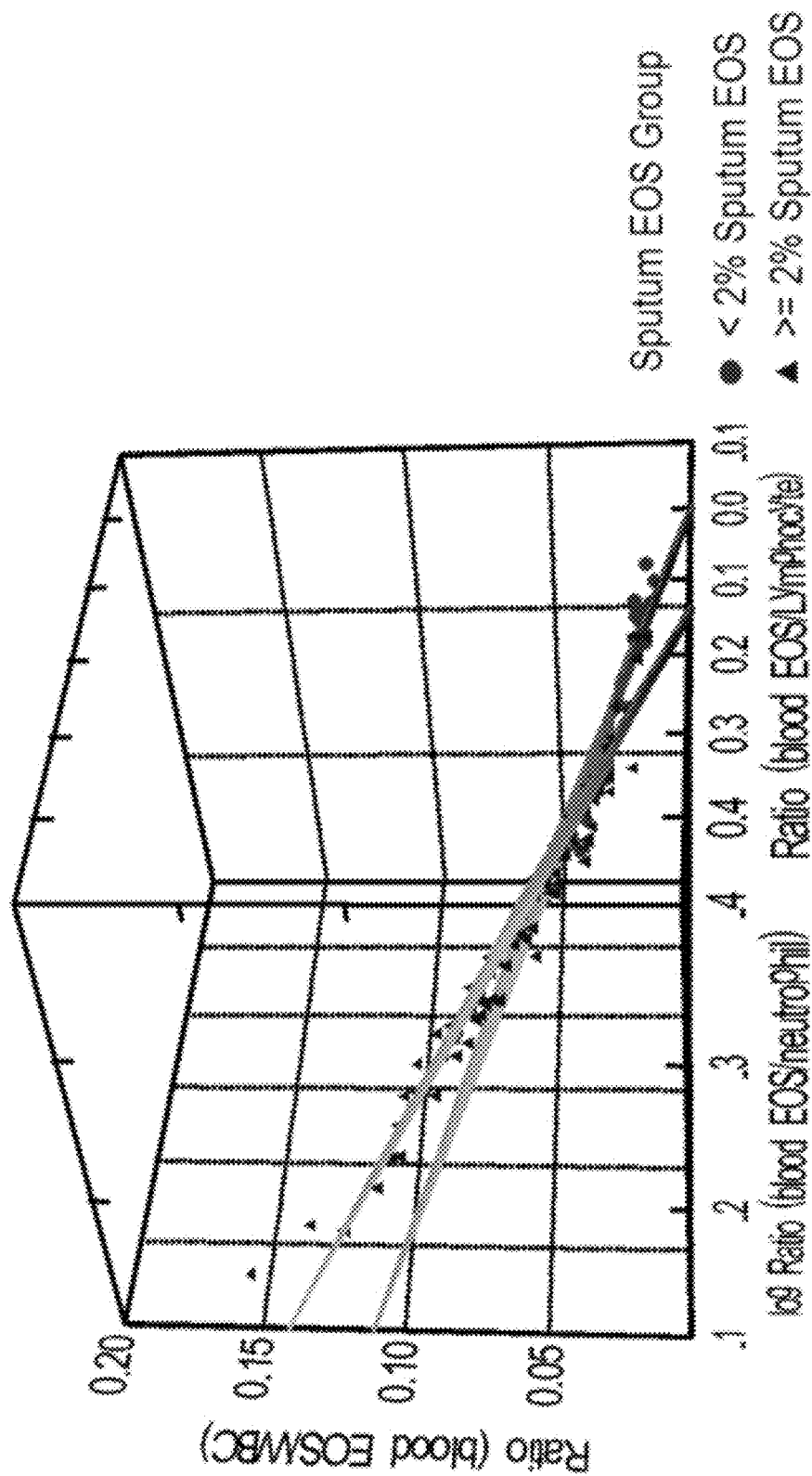
FIG. 5A and FIG. 5B show two different views of 3-dimensional surfaces showing separation of the eosinophilic and non-eosinophilic groups. The three axes are blood eosinophil/WBC ratio, logarithm of blood eosinophil/blood neutrophil and blood eosinophil/blood lymphocyte ratio.
Figure 5B:
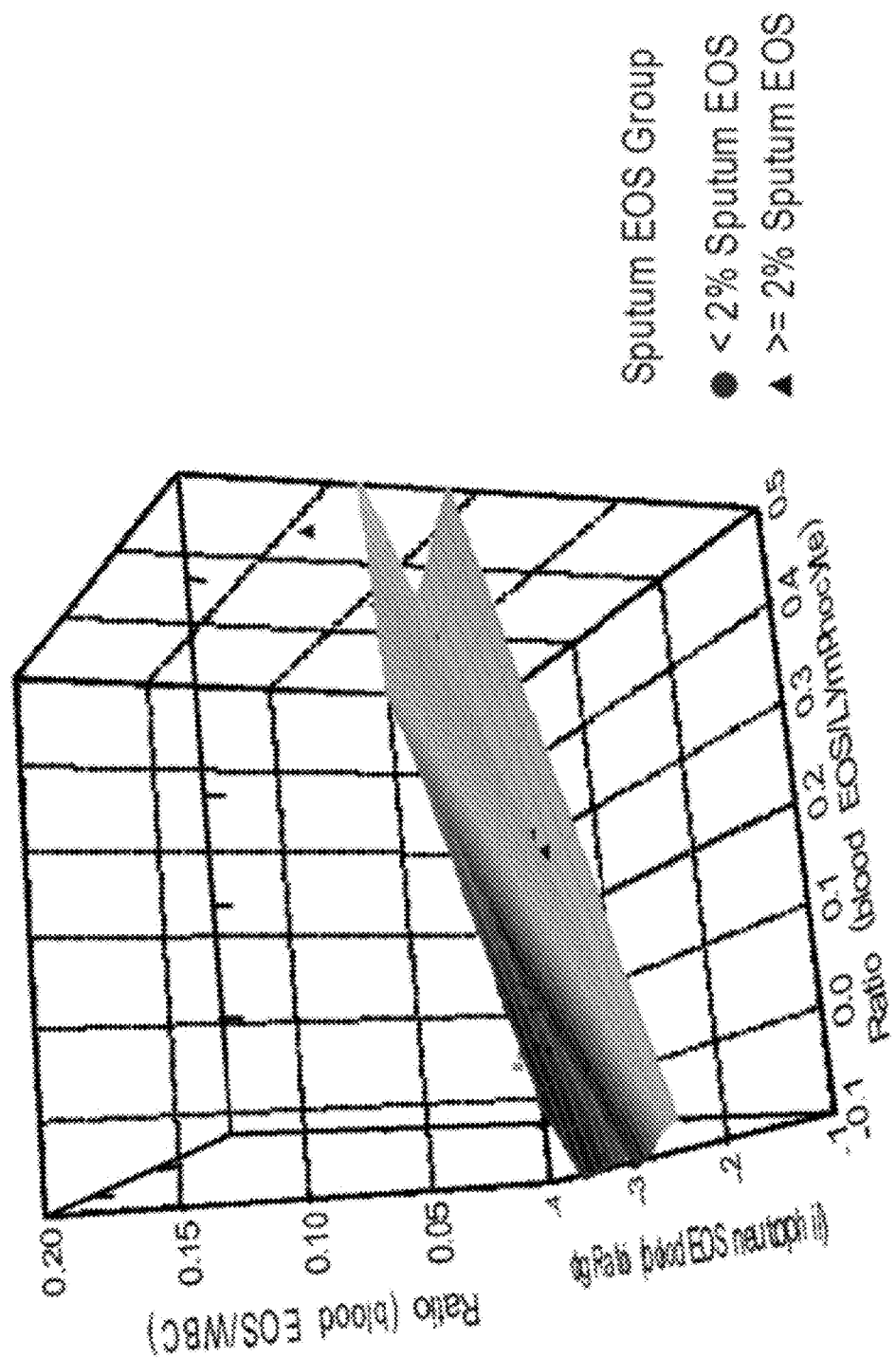
Figure 6A:
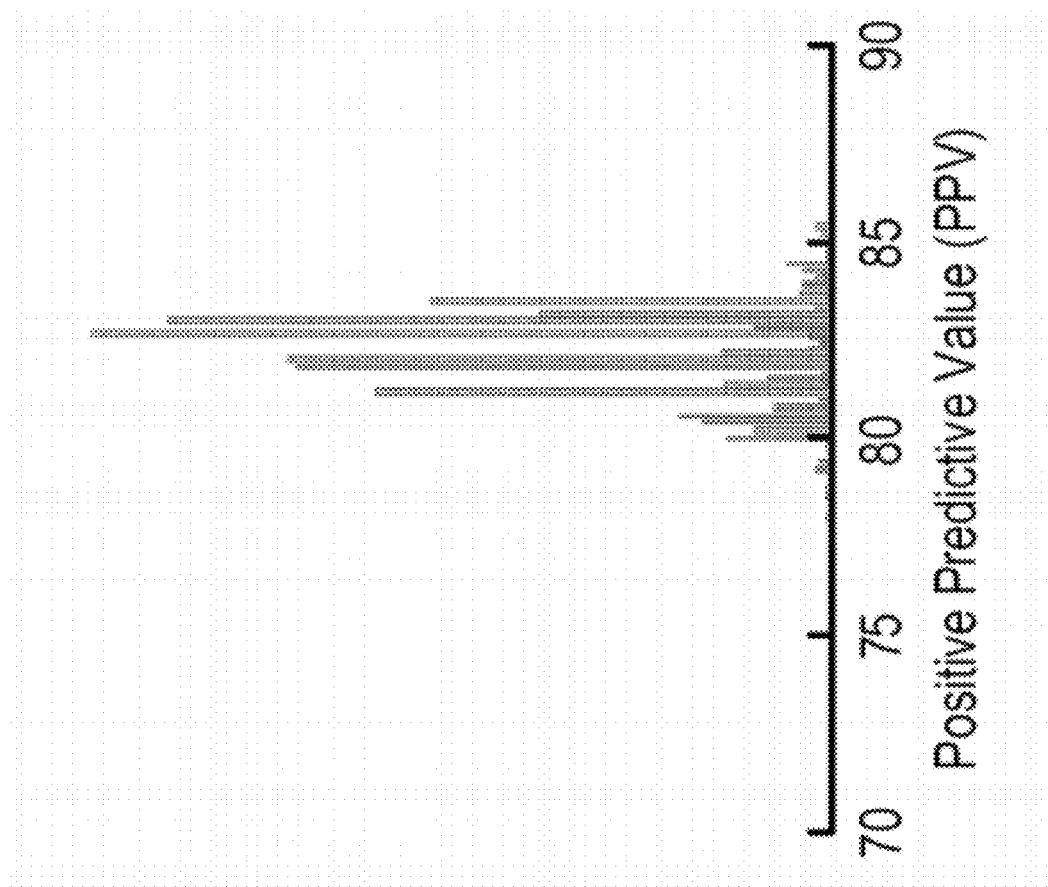
FIG. 6A shows the distribution of Positive Predictive Values (PPV) from bootstrap re-sampling applying a classifying method with three white blood cell-ratio derived predictors (blood eosinophil/blood lymphocyte; blood eosinophil/blood leucocyte; and, natural log(blood eosinophil/blood neutrophil) for classifying eosinophilic and non-eosinophilic asthmatics.
Figure 6B:
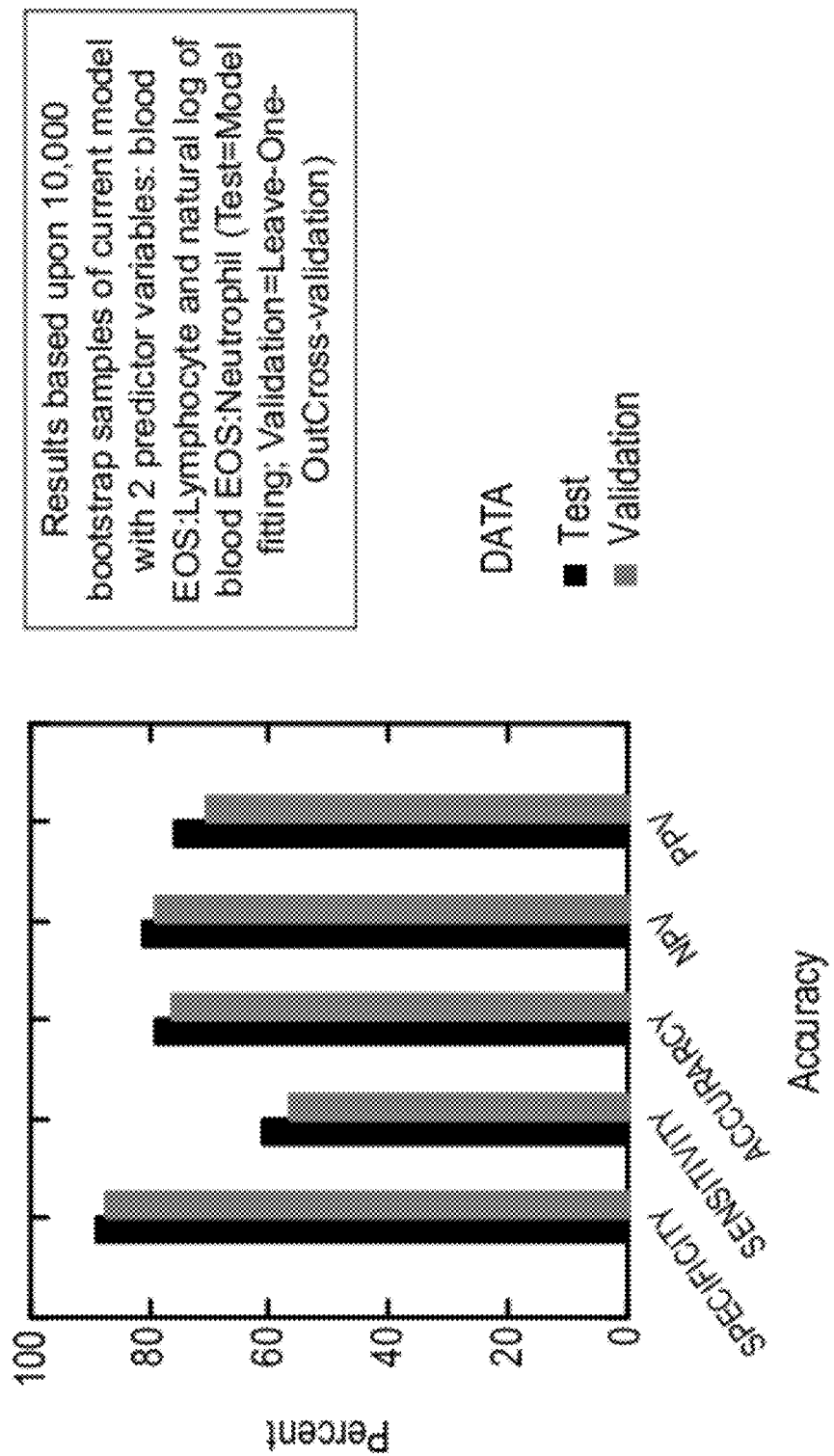
FIG. 6B shows the distribution of Specificity, Sensitivity, Accuracy, NPV and PPV values from bootstrap re-sampling applying a classifying method with three white blood cell-ratio derived predictors (blood eosinophil/blood lymphocyte; blood eosinophil/blood leucocyte; and, natural log(blood eosinophil/blood neutrophil) for classifying eosinophilic and non-eosinophilic asthmatics.

These 3 predictor variables yielded 83% PPV upon leave-one-out cross-validation. The data in FIGS. 5 (A and B) showed separation of the 2 groups according to 3-dimensional linear surfaces plotted using the 3 predictor variables. We further tested the robustness of the PPV using simulation (5,000 bootstrap samples). The simulations resulted in a PPV of 80% or greater at 98.8%, and a median PPV of 83% (FIGS. 6A and 6B). These observations confirmed the robustness of the model coefficients and estimates.

In the model depicted in FIG. 7, the ratio of blood eosinophils to blood leucocytes was discontinued as a predictor variable because the remaining 2 predictor variables yielded equivalent classification accuracy. Using LDA, we developed rules (algorithms) to assign individual patients to either non-eosinophilic (sputum EOS %<2.0) or eosinophilic (sputum EOS %≥2.0) groups. Thus, group assignments were made depending upon which of the following 2 equations results in a higher discriminant score (our current best prediction model):

Score 1(for Sputum EOS %<2.0)=−9.5243233+ [70.0974823×Blood Eosinophil/Blood Lymphocyte]−[3.7789926×natural log(Blood EOS/Blood Neutrophil)]

Score 2(for Sputum EOS %≥2.0)=−14.5853365+ [101.2197561×Blood EOS/Blood Lymphocyte]− [3.9567050×natural log(Blood EOS/Blood Neutrophil)]

A patient is diagnosed as having an eosinophilic disease or disorder if Score 1≤Score 2.

The predictor variables used in the above 2 equations were ratios of blood eosinophil to lymphocyte and neutrophil, respectively. The model coefficients were based upon the following unit of measurement for all independent variable measures: (×10³/μL).

The two equations yielded results for prediction and model validation as shown in TABLE 4. In a typical moderate to severe asthma population, the expected prevalence rate of eosinophilic phenotype is ~55%. Thus, in the absence of a diagnostic test (or pre-screening tool) as described herein, only 55% patients would have been expected to benefit from treatment by a therapy that specifically targets eosinophilic phenotypes of asthma. Accordingly, in a clinical trial situation, the targeted patient population could be severely diluted and result in trial failure of a potentially beneficial therapy. Similarly, in a clinical setting, there would be a 55% chance that a patient selected by a physician for eosinophil-targeted treatment may be correct. Accordingly, about 45% of non-responders would likely be prescribed an inappropriate treatment. Based upon validation 3 of our prediction model (which had a prevalence rate of 56%, a value close to the expected rate of 55% in the moderate to severe asthma patient population) the positive predictive value (PPV) was ~84%, which was 53% higher and a significant improvement from a non-screened ~55% prevalence rate.

TABLE 4

Prediction and validation accuracy for discrimination of asthma patients into eosinophilic and non-eosinophilic phenotypes.

| Data | Prediction (Pre-AC data from CP 138) | Validation 1 Jackknife (leave-one-out) cross-validation | Validation 2 Cohort 1 | Validation 3 Cohort 2 | Validation 4 Combined data (cohorts 1 and 2) |
|---|---|---|---|---|---|
| Sample size (n) | 23 | 23 | 99 | 75 | 174 |
| Specificity % | 93 | 93 | 79 | 84.8 | 83 |
| Sensitivity % | 63 | 63 | 74 | 64.3 | 70.5 |
| Overall accuracy % | 83 | 83 | 74.7 | 73.3 | 74 |
| Negative Predictive Value (NPV) % | 82.4 | 82.4 | 42 | 65 | 54.4 |
| Positive Predictive Value (PPV) % | 83.3 | 83.3 | 94 | 84.4 | 90.5 |
| Prevalence % (Eosinophilic proportion defined by Sputum EOS % ≥ 2.0) | 35 | 35 | 81 | 56 | 70 |

The model presented herein was shown to be robust and the PPV obtained in the prediction model was either maintained or improved upon in the different validations shown in TABLE 4. As expected, the PPV increased with prevalence rates. Based upon the current state of knowledge, we expected the moderate to severe asthma population to be ~55% eosinophilic, which corresponded with the Validation 3 column in TABLE 4. Thus, we expected our model to be approximately 64% sensitive, 85% specific, and have a PPV of approximately 84% when applied as a screening or clinical diagnostic tool.

TABLE 5 shows how the model performed when compared against using blood EOS cutoffs at various levels as observed in the current scientific literature (Lieberman, 2007; Nadif et al., 2009). Our model was shown to be superior in overall accuracy, NPV, and PPV on all comparisons. Our model displayed consistently higher sensitivity and specificity and was marginally lower in these two criteria only when compared against the lowest and highest blood EOS cutoffs, respectively.

TABLE 6 shows how the model combined with $FE_{NO}$ performed when compared against using blood EOS cutoffs in combination with $FE_{NO}$. The model presented herein combined with $FE_{NO}$ was proven to be superior in overall accuracy, NPV, and PPV. In addition, our model in combination with $FE_{NO}$ had higher sensitivity and specificity compared to using a blood EOS cutoff in combination with $FE_{NO}$.

TABLE 6

Comparison of predictive accuracy between our model in combination with $FE_{NO}$ and using a blood EOS cutoff in combination with $FE_{NO}$ for discriminating asthma patients into sputum eosinophilic and non-eosinophilic phenotypes.

| Accuracy Measure | Blood EOS > 300 or $FE_{NO}$ > 50 ppb | Positive ELEN Index or $FE_{NO}$ > 50 ppb |
|---|---|---|
| N (sample size) | 48 | 48 |
| Prevalence | 60% (29/48) | 60% (29/48) |
| Overall Accuracy | 77% (37/48) | 81.3% (39/48) |

TABLE 5

Comparison of predictive accuracy between our model and using different cutoffs of blood eosinophil counts as currently proposed in various publications for discriminating asthma patients into sputum eosinophilic and non-eosinophilic phenotypes.

| Data | Our Current Model Cohort 2 | Cutoff (Blood EOS ≥ 200) Cohort 2 | Cutoff (Blood EOS ≥ 300) Cohort 2 | Cutoff (Blood EOS ≥ 400) Cohort 2 |
|---|---|---|---|---|
| Sample size (n) | 75 | 75 | 75 | 75 |
| Specificity % | 84.8 | 61 | 76 | 88 |
| Sensitivity % | 64.3 | 71 | 57 | 38 |
| Overall accuracy % | 73.3 | 67 | 65 | 60 |
| Negative Predictive Value (NPV) % | 65 | 63 | 58 | 53 |
| Positive Predictive Value (PPV) % | 84.4 | 70 | 75 | 80 |
| Prevalence % (Eosinophilic proportion defined by Sputum EOS % ≥ 2.0) | 56 | 56 | 56 | 56 |

TABLE 6-continued

Comparison of predictive accuracy between our model in combination with $FE_{NO}$ and using a blood EOS cutoff in combination with $FE_{NO}$ for discriminating asthma patients into sputum eosinophilic and non-eosinophilic phenotypes.

| Accuracy Measure | Blood EOS > 300 or $FE_{NO}$ > 50 ppb | Positive ELEN Index or $FE_{NO}$ > 50 ppb |
|---|---|---|
| Specificity | 73.7% (14/19) | 79% (15/19) |
| Sensitivity | 79.3% (23/29) | 82.8% (24/29) |
| Negative Predictive Value (NPV) | 70% (14/20) | 75% (15/20) |
| Positive Predictive Value (PPV) | 82% (23/28) | 85.7% (24/28) |

Summary and Conclusions

Accurate classification of eosinophilic asthmatics is currently not possible because of the lack of a reliable and valid diagnostic tool. Such accurate classification is necessary for both screening and diagnostic purposes. Accurate screening of patients in clinical trials can enrich the trial samples by screening in study subjects who represent the pathological phenotypic populations of interest, and who are expected to benefit from a novel, targeted treatment. Similarly, accurate diagnosis in the clinic can allow practicing physicians to correctly identify patients who are likely to respond to such targeted therapies.

The disclosed predictive model can correctly identify and classify eosinophilic asthmatics. The model has, for example, application in clinical trials as well as in clinical practice. The disclosed model is easy to implement and only requires data from routinely collected CBC with differentials. The model resulted in a high PPV of 84% upon cross-validation on an independent dataset, which is a 53% improvement over correct classification by random chance alone based upon expected prevalence.

In addition, the sensitivity of the test was further increased when the model was used in combination with $FE_{NO}$ wherein a positive result from either the ELEN Index or $FE_{NO}$ indicated that the subject was an eosinophilic asthmatic.

Example 2

Treatment of Eosinophilic-Positive or Eosinophilic-Negative Subjects Predicted by Using a Statistical Model (ELEN Index) and $FE_{NO}$ Measurement Methodology A Phase 2b, randomized, double-blind, placebo-controlled, dose-ranging, multicenter study is conducted to evaluate the efficacy and safety of multiple-dose administration of an anti-IL-5R monoclonal antibody (benralizumab) in adult subjects with uncontrolled asthma requiring medium-dose or high-dose inhaled corticosteroid (ICS) plus long-acting β2 agonists (LABA) and having a history of ≥2 but ≤6 documented asthma exacerbations in the 12 months prior to screening that required use of a systemic corticosteroid burst. In this study, subjects are classified and stratified according to eosinophilic phenotype (eosinophilic-positive or eosinophilic-negative) as determined by the "ELEN Index" described in Example 1 above and by $FE_{NO}$ measurement.

Figure 8:
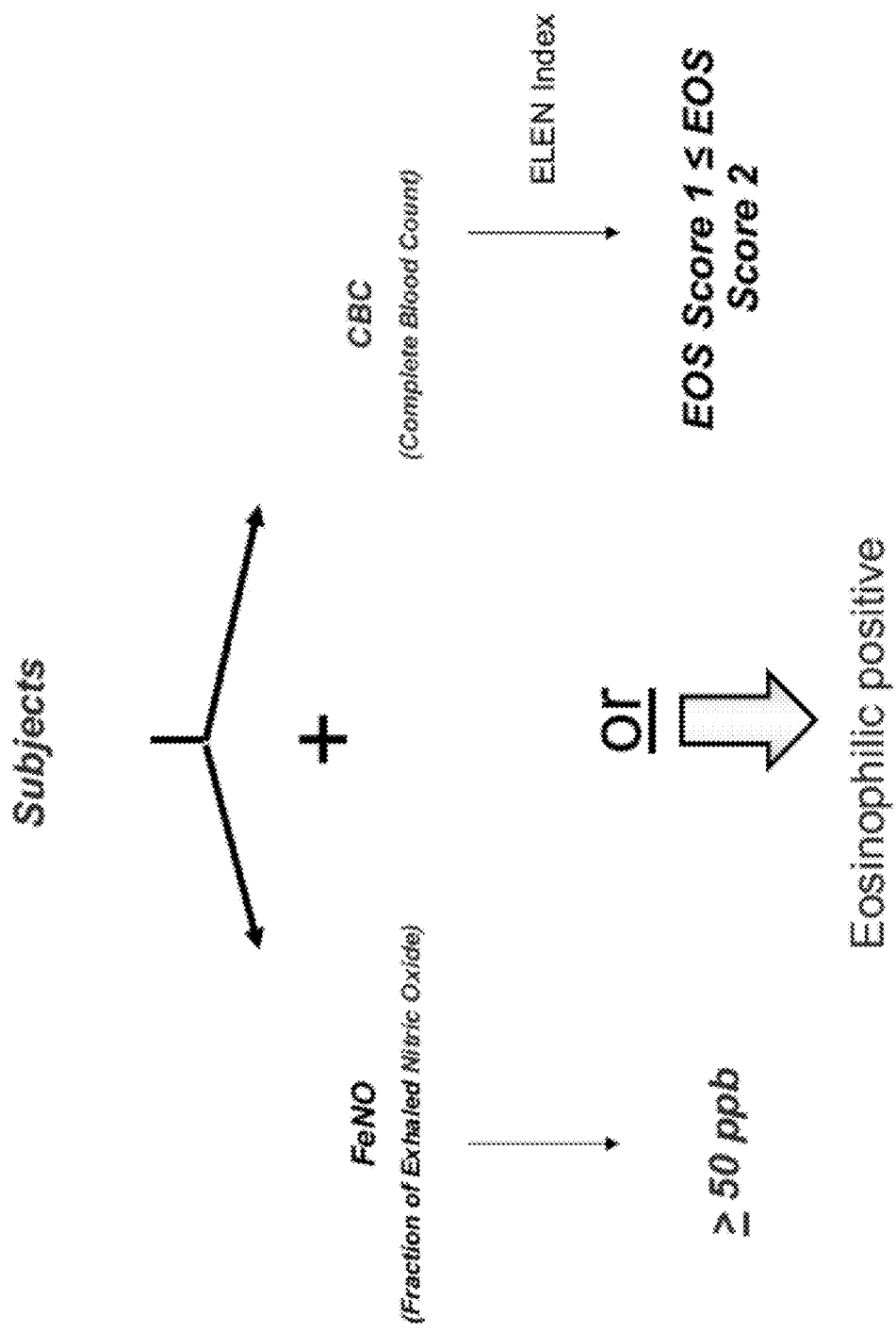
FIG. 8 shows a flowchart of the method used in a Phase 2b clinical trial to identify eosinophilic positive subjects.

In particular, a subject is considered to be eosinophilic positive if the ELEN Index is positive or if $FE_{NO}$ is greater than 50 ppb (as measured by NIOX MINO® or comparable on-line or off-line method) indicating that the subject is likely have a sputum eosinophil percentage of 2% or greater (see FIG. 8). In this study, eosinophilic-positive subjects are defined as those whose asthma is likely to be eosinophilic, and eosinophilic-negative subjects are defined as those whose asthma is unlikely to be eosinophilic. Subjects are also stratified based on baseline inhaled corticosteroid (ICS) use (approximately 60% of subjects on medium-dose vs. at least 40% of subjects on high-dose).

In some aspects, the samples to calculate ELEN Index are collected in the morning as the diurnal variation of blood eosinophil counts peaks around 1 AM and afternoon values tend to be higher than morning values. In some aspects, the samples are collected in the afternoon to have the maximum (awake-time eosinophil count). In some aspects, samples are collected at the same of day. In some aspects, subjects have not been treated with corticosteroid within 30 days of taking the $FE_{NO}$ measurement. Preferably, subjects have not been treated with corticosteroid within 6 weeks of the CBC and subjects on inhaled steroids should have been on a stable dose for 30 days prior to the test.

For the $FE_{NO}$ determination, airway inflammation is evaluated using a standardized single-breath $FE_{NO}$ test. (ATS/ERS, 2005). Since spirometry (e.g., Vital capacity (VC), Forced vital capacity (FVC), Forced expiratory volume (FEV), Forced expiratory flow (FEF) and Maximal voluntary ventilation (MVV)) can potentially impact the nitric oxide measurement, the $FE_{NO}$ test is preferably to be completed prior to any spirometry tests. In some aspects, subjects have not been treated with corticosteroid within 30 days of taking the $FE_{NO}$ measurement. Preferably, subjects have not been treated with corticosteroid within 6 weeks of taking the $FE_{NO}$ measurement. In addition, subjects should not eat or drink 1 hour prior to having the $FE_{NO}$, as this can also affect the results. While standing, subjects are to inhale to total lung capacity through the NIOX MINO® Airway Inflammation Monitor (Aerocrine, New Providence, N.J.) and then exhale for 10 seconds at 50 mL/sec (assisted by visual and auditory cues). The value obtained is recorded and the process repeated twice more for a total of 3 measurements. The three (3) $FE_{NO}$ values are averaged. A subject is considered to be eosinophilic positive if the ELEN Index is positive or if $FE_{NO}$ is equal to or greater than 50 ppb.

Approximately 100-150 study sites around the world are expected to participate in the study, and 482 subjects comprising 240 eosinophilic-positive subjects and 242 eosinophilic-negative subjects are to be randomized in the study. Eosinophilic-positive subjects are randomized in a 1:1:1:1 ratio to receive specified doses of the benralizumab or placebo; eosinophilic-negative subjects are randomized in a 1:1 ratio to receive one specified dose of benralizumab or placebo.

Benralizumab or placebo is administered according to a specified protocol for 40 weeks. After Week 40, subjects are monitored for an additional 12 weeks (through Week 52) for assessment of acute exacerbations. After Week 52, subjects are monitored for an additional 14 weeks (through Week 66) for safety including recovery of peripheral eosinophil count. If on the Week 66 visit, a subject's peripheral blood eosinophil count has not returned to 50 cells/μL or 20% of the Day 1 value, then the subject returns to the study site every 8-9 weeks until the subject's peripheral blood eosinophil count returns to 50 cells/μL or 20% of the Day 1 value or until Week 92, whichever occurs first.

A 3-week screening/run-in period precedes administration of benralizumab or placebo. During the 3-week screening/run-in period, subjects continue the same dose (medium-dose or high-dose) ICS/LABA combination product as prior to participation in the study (doses of ICS/LABA must be stable for 30 days prior to the Week-3 screening visit).

Subjects using individual ICS and LABA inhalers prior to participation in the study switch to an ICS/LABA combination product of their choice (either fluticasone/salmeterol or budesonide/formoterol) at an equivalent dose of ICS. Subjects remain on the same dose of ICS/LABA through the Week 52 visit.

At the end of the study, the assessed primary endpoint is the annual exacerbation rate, where annual asthma exacerbation rate is defined as the number of asthma exacerbations from Week 1 (Day 1) to Week 52. The secondary endpoints are safety and tolerability, dose selection, PK and IM, and other assessments of clinical activity (i.e., asthma control, pulmonary function, and health-related quality of life).

The primary and secondary analyses are conducted for eosinophilic-positive subjects. The same analyses are conducted for eosinophilic-negative subjects but as exploratory analyses. The primary analysis is based on a modified Intent to Treat (mITT) population. The primary comparisons are as follows: eosinophilic-positive/benralizumab dose 1 versus eosinophilic-positive/placebo; eosinophilic-positive/benralizumab dose 2 versus eosinophilic-positive/placebo; and eosinophilic-positive/benralizumab dose 3 versus eosinophilic-positive/placebo.

The results are analyzed to determine if the subjects in the benralizumab groups demonstrate a reduction in asthma exacerbations over the 12-month treatment period compared to subjects in the placebo group. See, e.g., the analysis for a 12-month study by Haldar et al. (2009), which compared mepolizumab, an anti-IL5 Mab, against placebo.

Example 3

A Predictive Statistical Model Combining a Peripheral Blood Cell Counts and $FE_{NO}$ Measurements ($EL$-$FE_{NO}$ Index)

A $FE_{NO}$ cutoff at 50 ppb has high specificity for identifying eosinophilic asthmatics, but its sensitivity is very low. There have been attempts to adjust the appropriate cutoffs for $FE_{NO}$ based upon patient's height, age, smoking status, and atopy (defined as the presence of specific IgE), which have resulted in publication of reference equations; but such reference equations only account for 9 to 11% of the variation (Olin et al., 2007). According to Olin et al. (2007), the most important information that could be extracted from the study is that the upper limits of $FE_{NO}$ range from 24.0 to 54.0 parts per billion, depending upon age and height. Thus, applying a $FE_{NO}$ cutoff of 50 ppb for all subjects (irrespective of their other biophysical attributes) in the absence of other classifiers is at best an inefficient diagnostics criterion that misses many eosinophilic patients.

Accordingly, we developed a second set of algorithms based on the white blood cell ratio approach used to develop the ELEN Index method. This new set of algorithms combined CBC with differential and $FE_{NO}$ measurements in a unified model to classify patients as either eosinophilic or non-eosinophilic. This method is especially useful if both drawing of blood for CBC and $FE_{NO}$ machines are available to a physician and are also acceptable to a patient.

This second set of equations has higher overall diagnostic accuracy than either the ELEN Index method or the ELEN Index combined with a FENO>50 ppb cutoff discussed above, and it is more balanced in relation to PPV and NPV. This new set of equations for classifying sputum eosinophilic asthmatics and the accompanying decision rule were also based on Fisher's Linear Discriminant Analysis (LDA).

Scores were calculated in this method according to the following equations:

Score 1(for Sputum EOS %<2.0)=−4.6368456+ (0.0300382×$FE_{NO}$ ppb)−[2.5409793×natural logarithm(Blood Eosinophil/Blood Lymphocyte)]; and, Score 2(for Sputum EOS %≥2.0)=−3.6017103+ (0.0559650×$FE_{NO}$ ppb)−[1.7349461×natural logarithm(Blood Eosinophil/Blood Lymphocyte)].

As in the previous set of equations, a patient was diagnosed as having an eosinophilic phenotype if Score 1≤Score 2. If Score 1>Score 2, the patient was diagnosed as having a sputum non-eosinophilic phenotype.

Our second set of equations, which utilized CBC and $FE_{NO}$ measurements, was initially developed and tested (leave-one-out cross-validation) on data from an Astra Zeneca asthma study corresponding to 48 cases with data on sputum, blood, and $FE_{NO}$ measurements. Classification accuracy on the test data set and the leave-one-out cross-validation showed a PPV of 85% and a NPV of 71% with an overall diagnostic accuracy of 79%, as presented in TABLE 7. There was no difference in classification accuracies in the test data and in the cross-validation, which proved the robustness of the second set of equations.

The CBC for utilization in this new set of equations can be measured in any units as long as the measurements are consistent because the predictor variable Eosinophil/Lymphocyte is a ratio. The $FE_{NO}$ measurements in ppb should preferably be captured at an exhalation flow rate of 50 mL/s, in conformance with the official ATS clinical practice guidelines (Dweik et al., 2011).

TABLE 7

Prediction and validation accuracy of equations combining both CBC and $FE_{NO}$ measurements for discrimination of asthma patients into eosinophilic and non-eosinophilic phenotypes.

| Measure | Prediction | Validation (leave-one-out cross-validation) |
|---|---|---|
| Sample size (n) | 48 | 48 |
| Specificity (%) | 79.0 | 79.0 |
| Sensitivity (%) | 79.3 | 79.3 |
| NPV (%) | 71.4 | 71.4 |
| PPV (%) | 85.2 | 85.2 |
| Accuracy (%) | 79.2 | 79.2 |
| Prevalence (Eosinophilic proportion defined by Sputum Eos % >= 2.0) | 60.4 | 60.4 |

Independent Validation on a Biomarker Study Developed and Undertaken for the Specific Purpose of Prospective Validation of the Classification Accuracies We conducted a prospective biomarker study to test and validate our equations and classification methods with a planned sample size of 100 asthmatics in 18 sites in Canada and the United States (ClinicalTrials.gov Identifier: NCT01334853). A total of 197 subjects aged 18 to 75 years at screening requiring daily inhaled corticosteroids for persistent asthma were screened for the study of which 97 were enrolled and 91 completed the study (hereafter referred to as CP-223 for Clinical Protocol 223). The CP-223 study was specifically designed to test the accuracy and reliability of our pre-specified algorithms and diagnostic methods for classifying sputum eosinophilic asthmatics.

We collected data on two occasions, Day 1 and Day 8, to capture variability in measurements a week apart. The performance of our diagnostics algorithms and methods on the prospectively collected data for averaged values (average of Day 1 and Day 8) and for individual one-time data capture (Day 1 and Day 8) are presented in TABLES 8, 9, and 10.

with the CBC only algorithm (ELEN Index), shown in the top row, is a slight improvement over the CBC only algorithm. However, the data in the second row showed that utilization of the $FE_{NO}$ 50 ppb cutoff alone was clearly the weakest classification system because of very low sensitivity (21%). This low sensitivity in the method using the $FE_{NO}$ 50 ppb cutoff alone resulted in low NPV (54%) and low overall accuracy (57%).

TABLE 8

Diagnostic accuracy comparisons of CBC only Eosinophil Index, $FE_{NO}$ 50 ppb cutoff, Eosinophil Index or $FE_{NO}$ 50 ppb cutoff, and Eosinophil Index with CBC and $FE_{NO}$ measurements on averaged data in CP223 Study.

| Test | Reference | Specificity (%) | Sensitivity (%) | NPV (%) | PPV (%) | Accuracy (%) | Prevalence (%) | Sample size (n) |
|---|---|---|---|---|---|---|---|---|
| Eosinophil Index from Averaged CBC (Day 1 and Day 8) | Sputum Eosinophil Cutoff of >=2% from Averaged Measurements (Day 1 and Day 8) | 88.6 | 59.6 | 66.7 | 84.8 | 73.3 | 52.2 | 90 |
| FENO >= 50 ppb from Averaged Measurements (Day 1 and Day 8) | Sputum Eosinophil Cutoff of >=2% from Averaged Measurements (Day 1 and Day 8) | 95.7 | 20.8 | 53.7 | 83.3 | 57.4 | 51.1 | 94 |
| Positive for Eosinophil Index from Averaged CBC or FENO >= 50 ppb from Averaged Measurements (Day 1 and Day 8) | Sputum Eosinophil Cutoff of >=2% from Averaged Measurements (Day 1 and Day 8) | 84.1 | 63.8 | 68.5 | 81.1 | 73.6 | 51.6 | 91 |
| Positive for Index Utilizing Both CBC and FENO from Averaged Measurements (Day 1 and Day 8) | Sputum Eosinophil Cutoff of >=2% from Averaged Measurements (Day 1 and Day 8) | 72.1 | 78.7 | 75.6 | 75.5 | 75.6 | 52.2 | 90 |

The data presented in TABLE 8 showed the practical utility of the CBC only algorithm (top row) as well as the CBC and FENO algorithm (bottom row) as supported by high PPV and overall accuracy. The data presented in the third row of the table, which utilized $FE_{NO}$ 50 ppb cutoff as an "or" criterion The last row, corresponding to the new algorithm integrating both CBC and $FE_{NO}$ measurements in the equations, had the highest overall accuracy and a more balanced diagnostic performance as evidenced from all diagnostics measures with values above 75% (except specificity at 72%).

TABLE 9

Diagnostic accuracy comparisons of CBC only Eosinophil Index, $FE_{NO}$ 50 ppb cutoff, Eosinophil Index or $FE_{NO}$ 50 ppb cutoff, and Eosinophil Index with CBC and $FE_{NO}$ measurements on Day 1 data in CP-223 Study.

| Test | Reference | Specificity (%) | Sensitivity (%) | NPV (%) | PPV (%) | Accuracy (%) | Prevalence (%) | Sample size (n) |
|---|---|---|---|---|---|---|---|---|
| Eosinophil Index from CBC (Day 1) | Sputum Eosinophil Cutoff of >=2% (Day 1) | 82.5 | 60.0 | 70.2 | 75.0 | 72.0 | 46.7 | 75 |
| FENO >= 50 ppb (Day 1) | Sputum Eosinophil Cutoff of >=2% (Day 1) | 90.5 | 15.8 | 54.3 | 60.0 | 55.0 | 47.5 | 80 |
| Positive for Eosinophil Index from CBC (Day 1) or FENO >= 50 ppb (Day 1) | Sputum Eosinophil Cutoff of >=2% (Day 1) | 75.0 | 62.9 | 69.8 | 68.8 | 69.3 | 46.7 | 75 |
| Positive for Index Utilizing Both CBC and FENO Measurements (Day 1) | Sputum Eosinophil Cutoff of >=2% (Day 1) | 61.5 | 73.5 | 72.7 | 62.5 | 67.1 | 46.6 | 73 |

TABLE 10

Diagnostic accuracy comparisons of CBC only Eosinophil Index, $FE_{NO}$ 50 ppb cutoff, Eosinophil Index or $FE_{NO}$ 50 ppb cutoff, and Eosinophil Index with CBC and $FE_{NO}$ measurements on Day 8 data in CP-223 Study.

| Test | Reference | Specificity (%) | Sensitivity (%) | NPV (%) | PPV (%) | Accuracy (%) | Prevalence (%) | Sample size (n) |
|---|---|---|---|---|---|---|---|---|
| Eosinophil Index from CBC (Day 8) | Sputum Eosinophil Cutoff of >=2% (Day 8) | 86.1 | 58.3 | 67.4 | 80.8 | 72.2 | 50.0 | 72 |
| FENO >= 50 ppb (Day 8) | Sputum Eosinophil Cutoff of >=2% (Day 8) | 97.3 | 16.2 | 53.7 | 85.7 | 56.8 | 50.0 | 74 |
| Positive for Eosinophil Index from CBC (Day 8) or FENO >= 50 ppb (Day 8) | Sputum Eosinophil Cutoff of >=2% (Day 8) | 83.3 | 61.1 | 68.2 | 78.6 | 72.2 | 50.0 | 72 |
| Positive for Index Utilizing Both CBC and FENO Measurements (Day 8) | Sputum Eosinophil Cutoff of >=2% (Day 8) | 72.2 | 75.0 | 74.3 | 73.0 | 73.6 | 50.0 | 72 |

TABLE 9 and TABLE 10 show similar patterns and performance as in TABLE 8 but with a slight decline in overall accuracy because they each represented measurements on only a single day. Thus, all 3 tables support and prospectively validate our algorithms in consistency of classification accuracies for discriminating between sputum eosinophilic and non-eosinophilic asthmatics. These 3 tables also indicate that overall accuracy can be increased by measuring biological samples from at least two different time points and use the average values. This conclusion is further supported by results shown in TABLE 11.

TABLE 11

Percent agreement in classification accuracy between two time points (Day 1 and Day 8) and with the average of Day 1 and Day 8 for the various diagnostics.

| Measure/Pair | Agreement (%) | Sample Size (n) |
|---|---|---|
| Sputum (Gold Standard Reference) | | |
| Day 1 vs. Day 8 | 75.8 | 62 |
| Average vs. Day 1 | 90.2 | 82 |
| Average vs. Day 8 | 90.2 | 74 |
| Eosinophil Index (CBC only) | | |
| Day 1 vs. Day 8 | 83.0 | 88 |
| Average vs. Day 1 | 94.3 | 88 |
| Average vs. Day 8 | 89.0 | 91 |
| FENO >= 50 ppb Cutoff | | |
| Day 1 vs. Day 8 | 93.6 | 94 |
| Average vs. Day 1 | 98.9 | 94 |
| Average vs. Day 8 | 94.8 | 96 |
| Eosinophil Index (CBC) or FENO >= 50 ppb Cutoff | | |
| Day 1 vs. Day 8 | 84.1 | 88 |
| Average vs. Day 1 | 95.5 | 88 |
| Average vs. Day 8 | 89.1 | 92 |

TABLE 11-continued

Percent agreement in classification accuracy between two time points (Day 1 and Day 8) and with the average of Day 1 and Day 8 for the various diagnostics.

| Measure/Pair | Agreement (%) | Sample Size (n) |
|---|---|---|
| Eosinophil Index (CBC and FENO Measurements) | | |
| Day 1 vs. Day 8 | 87.2 | 86 |
| Average vs. Day 1 | 96.5 | 86 |
| Average vs. Day 8 | 91.2 | 91 |

Even the gold standard reference (classification based on EOS % cutoff at 2%) only agrees 76% of the time between Day 1 and Day 8 sampling. However, when this reference value was established to be the average of the two days, the agreement between Day 1 and the average, and Day 8 and the average were both increased to 90%. Similarly, the performances of the various diagnostics (algorithms/methods) followed the same pattern as the reference measure and showed higher agreement between an individual day and the average, than between individual days.

Figure 9:
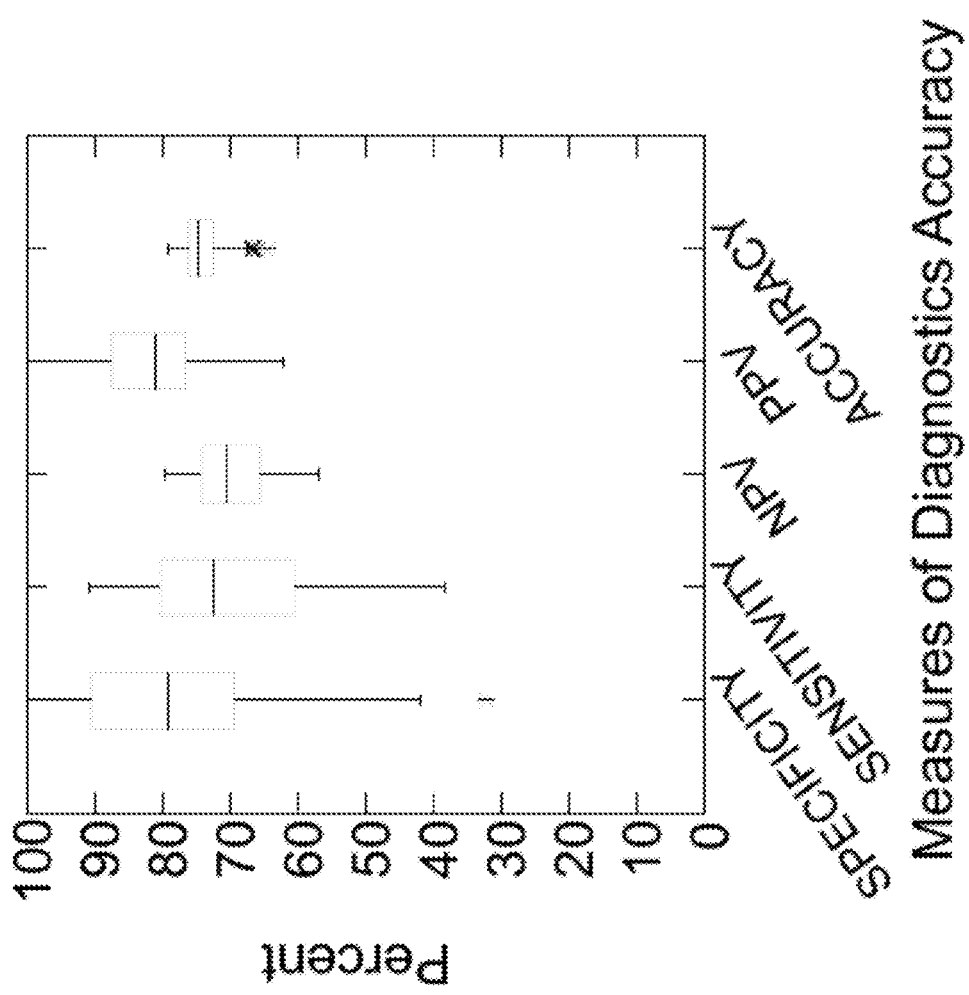
FIG. 9 show box plots of diagnostic accuracy measures observed using bootstrap re-sampling (n=2500 bootstrap samples drawn with replacement) on pooled data (n=138) from the Astra Zeneca clinical study (n=48) and the averaged values in the CP-223 clinical study (n=90) using the two predictor variables in the EL-$FE_{NO}$ Index classification method ($FE_{NO}$ and natural logarithm of blood eosinophil/blood lymphocyte).

In order to test the robustness of $EL-FE_{NO}$ Index method, and to better understand the statistical distribution and associated descriptive statistics of our prediction algorithm's coefficients and the two predictor variables ($FE_{NO}$ and natural logarithm of blood eosinophil/blood lymphocyte), a bootstrap re-sampling (n=2500 bootstrap samples drawn with replacement) was carried out on pooled data (n=138) from the Astra Zeneca study (n=48) and the averaged values in CP-223 (n=90). The LDA algorithm with the two predictor variables ($FE_{NO}$ and natural logarithm of blood eosinophil/blood lymphocyte) was run 2500 times on the bootstrap samples (prevalence=55%), and the diagnostic classification accuracies and the average values of the predictor variables were examined. The results are displayed in TABLES 12, 13 and 14 and in FIGS. 9, 10 and 11.

TABLE 12

Range of coefficients in EL-FE$_{NO}$ Index model along with the median, mean and values associated with the model yielding highest accuracy.
Generic Model
Score for Sputum EOS % < 2.0:
a + [b × FENO] + [c × natural log (Blood EOS/Blood Lymphocyte)]
Score for Sputum EOS % ≥ 2.0:
d + [e × FENO] + [f × natural log (Blood EOS/Blood Lymphocyte)]
Range of Model Coefficients

| Coefficient | Current Model | Mean | Median | Model Yielding Highest Accuracy | Minimum | Maximum |
| --- | --- | --- | --- | --- | --- | --- |
| a | −4.6368456 | −7.5257450 | −7.2538673 | −5.9797590 | −13.7614678 | −4.0353017 |
| b | 0.0300382 | 0.0527457 | 0.0494645 | 0.0471360 | 0.0113161 | 0.1606247 |
| c | −2.5409793 | −4.8115804 | −4.6156535 | −3.6534203 | −9.8400302 | −2.2132457 |
| d | −3.6017103 | −5.5136622 | −5.3604495 | −4.8723214 | −10.1869882 | −3.2140347 |
| e | 0.0559650 | 0.0713288 | 0.0679330 | 0.0660342 | 0.0350663 | 0.1749090 |
| f | −1.7349461 | −3.5649589 | −3.4006071 | −2.8021412 | −7.7410024 | −1.4804909 |

TABLE 13

Descriptive statistics of diagnostic accuracy measures observed in the 2500 bootstrap samples.

| Statistics | Specificity (%) | Sensitivity (%) | NPV (%) | PPV (%) | Accuracy (%) |
| --- | --- | --- | --- | --- | --- |
| n | 2500 | 2500 | 2500 | 2500 | 2500 |
| Minimum | 32.26 | 38.16 | 56.88 | 62.16 | 64.49 |
| Maximum | 100 | 90.79 | 79.59 | 100 | 78.99 |
| Median | 79.03 | 72.37 | 70.42 | 81.16 | 74.64 |
| Mean | 78.79 | 70.08 | 69.48 | 81.67 | 73.99 |
| SD | 11.79 | 11.96 | 5.72 | 6.25 | 2.66 |

TABLE 14

Descriptive statistics of the mean values of the two predictor variables observed in the 2500 bootstrap samples associated with each discriminated class.

| Statistics | Mean FENO (ppb) < 2% Sputum EOS Group | Mean FENO (ppb) >= 2% Sputum EOS Group | Mean Natural Log (Blood Eosinophil/Blood neutrophil) < 2% Sputum EOS | Mean Natural Log (Blood Eosinophil/Blood neutrophil) >= 2% Sputum EOS |
| --- | --- | --- | --- | --- |
| n | 2500 | 2500 | 2500 | 2500 |
| Minimum | 20.4 | 34.2 | −3.0477 | −2.0863 |
| Maximum | 29.7 | 69.8 | −2.2279 | −1.4639 |
| Median | 25.0 | 47.9 | −2.5698 | −1.7502 |
| Mean | 25.0 | 48.1 | −2.5747 | −1.7511 |
| SD | 1.3 | 4.7 | 0.1084 | 0.0860 |

The data in TABLE 12 showed the potentially useful range of the various model coefficients that can be used to accurately discriminate between eosinophilic and non-eosinophilic patients. The data in TABLE 13 also showed that these coefficients resulted in overall classification accuracy ranging from 65 to 79% with expected mean and median accuracy at 74 and 75%, respectively. The PPV was of clinical relevance, with mean and median PPV being 82 and 81%, respectively.

Figure 10:
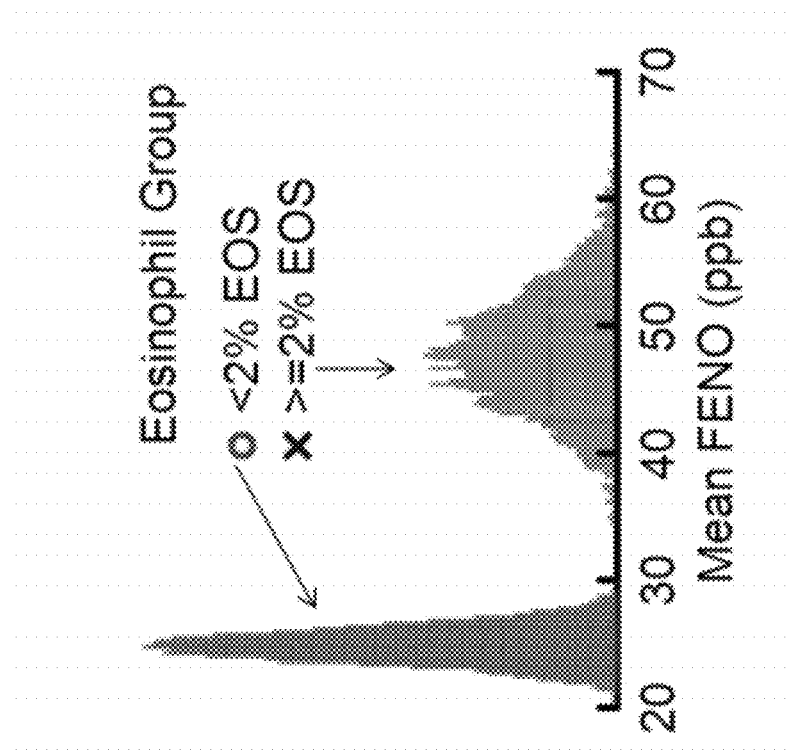
FIG. 10 shows the distribution of the dot density plots of the average values of the first predictor variable ($FE_{NO}$) in the 2500 bootstrap samples superimposed on the same graph.
Figure 11:
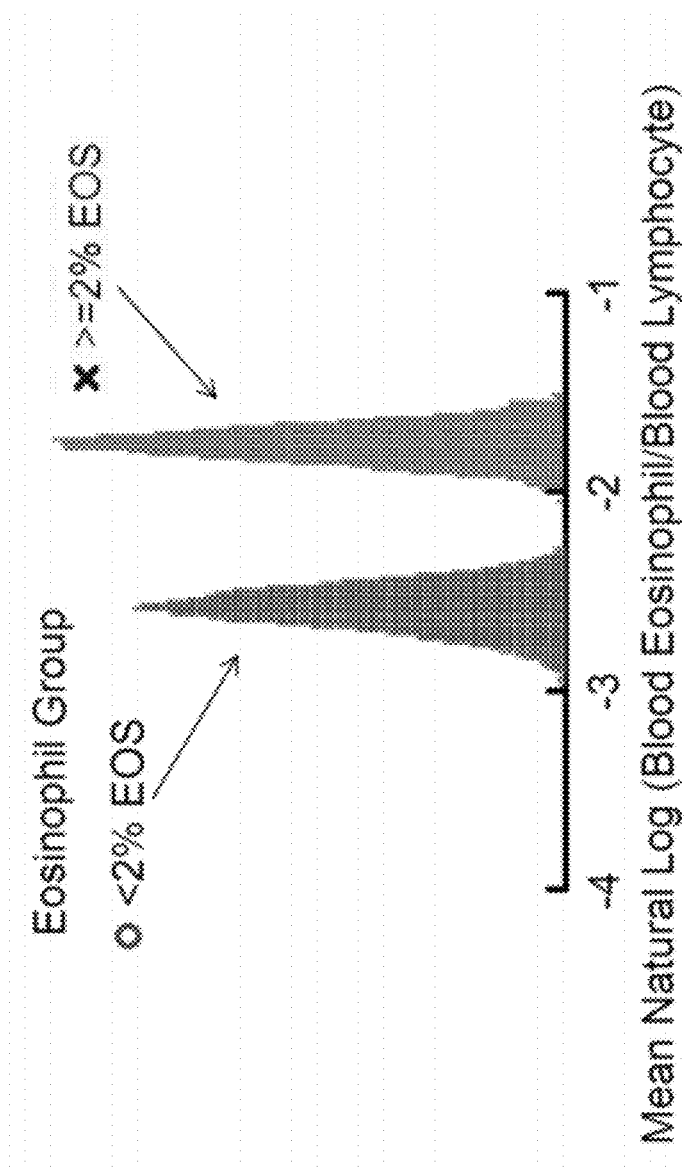
FIG. 11 shows the distribution of the dot density plots of the average values of the second predictor variable (natural log of blood eosinophil/blood lymphocyte) in the 2500 bootstrap samples superimposed on the same graph.

The data in TABLE 14 (and FIGS. 10 and 11) showed the expected mean values of the two predictor variables used in the algorithms and their distributions. The clear separation in expected mean distribution of these two predictor variables jointly contributed to the high diagnostic classification accuracy measures displayed in FIG. 9. FIG. 10 also showed that using a hard cut-off of 50 ppb in FE$_{NO}$ to discriminate between eosinophilic and non-eosinophilic patients was not a very accurate and efficient method because many eosinophilic patients could have FE$_{NO}$ values well below 50 ppb With the collected data from Study CP-223, we have demonstrated that our algorithms are superior to currently approved guideline of FE$_{NO}$ cutoff at 50 ppb. Our method and algorithms are simple and practical and correspond well with sputum measurement, which is considered as the gold standard method but impractical for clinical use to discriminate between eosinophilic and non-eosinophilic asthmatics. We have also demonstrated with the data that single time point measurements used in our algorithms can be sufficiently accurate for routine clinical use, but averaging multiple measurements at least a week apart will result in higher classification accuracies.

REFERENCES

ATS/ERS, Am. J. Respir. Crit. Care Med. 2005; 171:912-30.
ATS. Am. J. Respir. Crit. Care Med. 1995; 152:S77-S120.
ATS, Am. J. Respir. Crit. Care Med. 2011; 184:602-615.
Belda et al. Am. J. Respir. Crit. Care. Med. 2000; 161:475-478.
Belda et al., Can. Respir. J. 2006; 13:129-133.
Balzar et al., Eur. Respire. J. 2002; 20:254-259.
Barnes et al., Chest. 2010; 138:682-692.
Dweik et al., Am. J. Respir. Crit. Care Med. 2011; 184:602-615.
Gaga et al., Eur. Respir. Rev. 2009; 18:112, 58-65.

Gibson, Thorax 2009; 64:369-370.
Green et al., Lancet 2002; 360:1715-21.
Haldar et al., N. Engl. J. Med. 2009; 360:973-984.
Hill, LabMedicine 2009; 40:709-718.
Huberty. Applied Discriminant Analysis. Wiley Series in Probability and Mathematical Statistics. 1994. John Wiley & Sons, Inc. New York, 466 pages.
Jayaram et al., Eur. Respir. J. 2006; 27:483-94.
Kesten & Chapman, Chest. 1993; 104:254-258
Lieberman. Allergy Asthma Proc. 2007; 28:5, 510-513.
McLachlan. Discriminant Analysis and Statistical Pattern Recognition. Wiley Series in Probability and Mathematical Statistics. 1992. John Wiley & Sons, Inc. New York, 526 pages.
Molfino, Expert Opin. Biol. Ther. (Early Online, 2012) doi: 10.1517/14712598.2012.674938, Informa UK, Ltd. ISSN 1471-2598.
Nadif et al., Thorax 2009; 64:374-380.
Nair et al., N. Engl. J. Med. 2009; 360:985-993.
Olin et al., Chest 2007; 131; 1852-1856.
Pavord & Martin, Expert Rev. Resp. Med. 2009; 3:107-111.
Petsky et al., Thorax 2012; 67: 199-208.
Smith et al., Am J. Respir. Crit. Care Med. 2005; 172:453-459.
Stick, Am J. Respir. Crit. Care Med. 2009; 179:87-88.
SYSTAT 11. SYSTAT Software, Inc. 2004.
Szefler et al., J. Allergy Clin. Immunol. 2012; 129: S9-23.
Taylor et al., Thorax 2006; 61:817-827.
Travers et al., Am J. Respir. Crit. Care Med. 2007; 176:238-242.
Tsuburai et al., 2010, Arerugi 59:956-64
Turner, Mini-Rev. Med. Chem. 2007; 7:541-544.

The foregoing description of the specific aspects will so fully reveal the general nature of the disclosure that others can, by applying knowledge within the skill of the art, readily modify and/or adapt for various applications such specific aspects, without undue experimentation, without departing from the general concepts provided. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

---

What is claimed is:

1. A method of treating a patient having asthma comprising:
   (a) measuring a white blood cell count in a sample taken from a patient having eosinophilic asthma to calculate a white blood cell ratio, wherein the white blood cell count comprises an eosinophil count, a neutrophil count, a lymphocyte count, an eosinophil precursor count, a basophil precursor count, or any combination thereof and wherein the white blood cell ratio is a ratio between an eosinophil count and a second white blood cell type count;
   (b) calculating a diagnostic score from the white blood cell ratio, wherein the diagnostic score indicates whether the patient has eosinophilic asthma, and wherein the diagnostic score is the variance between two intermediate scores (Score 1 and Score 2), wherein Score 1 is calculated according to the formula:

Score 1=$a$+[$b$×blood eosinophil/blood lymphocyte]−[$c$×natural log(blood eosinophil/blood neutrophil)]

and Score 2 is calculated according to the formula:

Score 2=$d$+[$e$×blood eosinophil/blood lymphocyte]−[$f$×natural log(blood eosinophil/blood neutrophil)], wherein:
   (i) a is −9.5243233;
   (ii) b is 70.0974823;
   (iii) c is 3.7789926;
   (iv) d is −14.5853365;
   (v) e is 101.2197561; and,
   (vi) f is 3.9567050,
   wherein a Score 1≤Score 2 indicates that the patient has eosinophilic asthma; and,
   (c) administering an effective amount of an anti-IL5R antibody to the patient if the patient has eosinophilic asthma.

2. The method of claim 1, wherein the anti-IL-5R antibody is benralizumab.

3. The method of claim 1, wherein the anti-IL5R antibody binds the same epitope as benralizumab.

* * * * *

SEQUENCE LISTING

```
<160> NUMBER OF SEQ ID NOS: 4

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys
            100                 105

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45
```

Tyr His Thr Ser Arg Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 121
<212> TYPE: PRT
<213> ORGANISM: Homo sapiens

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
            35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
            115                 120

<210> SEQ ID NO 4
<211> LENGTH: 451
<212> TYPE: PRT
<213> ORGANISM: Homo sapiens

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

-continued

```
Val Ile His Trp Val Arg Gln Arg Pro Gly Gln Gly Leu Ala Trp Met
         35                  40                  45
Gly Tyr Ile Asn Pro Tyr Asn Asp Gly Thr Lys Tyr Asn Glu Arg Phe
     50                  55                  60
Lys Gly Lys Val Thr Ile Thr Ser Asp Arg Ser Thr Ser Thr Val Tyr
 65                  70                  75                  80
Met Glu Leu Ser Ser Leu Arg Ser Glu Asp Thr Ala Val Tyr Leu Cys
                 85                  90                  95
Gly Arg Glu Gly Ile Arg Tyr Tyr Gly Leu Leu Gly Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

```
Pro Gly Lys
    450
```